US 10,195,201 B2

(12) United States Patent
Shen et al.

(10) Patent No.: US 10,195,201 B2
(45) Date of Patent: Feb. 5, 2019

(54) HETEROARYL-PYRIMIDINONE COMPOUNDS AS PDE2 INHIBITORS

(71) Applicant: Merck Sharp & Dohme Corp., Rahway, NJ (US)

(72) Inventors: Dong-Ming Shen, Edision, NJ (US); Jonathan E. Wilson, Rahway, NJ (US); Troy McCracken, Berkeley Heights, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/571,192

(22) PCT Filed: May 2, 2016

(86) PCT No.: PCT/US2016/030342
§ 371 (c)(1),
(2) Date: Nov. 1, 2017

(87) PCT Pub. No.: WO2016/179059
PCT Pub. Date: Nov. 10, 2016

(65) Prior Publication Data
US 2018/0280390 A1   Oct. 4, 2018

Related U.S. Application Data

(60) Provisional application No. 62/157,232, filed on May 5, 2015.

(51) Int. Cl.
A61K 31/513   (2006.01)
C07D 239/36   (2006.01)
C07D 403/04   (2006.01)
A61P 25/06    (2006.01)
A61P 25/28    (2006.01)
A61P 25/18    (2006.01)
A61P 25/22    (2006.01)
A61P 25/16    (2006.01)

(52) U.S. Cl.
CPC ............ *A61K 31/513* (2013.01); *A61P 25/06* (2018.01); *A61P 25/16* (2018.01); *A61P 25/18* (2018.01); *A61P 25/22* (2018.01); *A61P 25/28* (2018.01)

(58) Field of Classification Search
None
See application file for complete search history.

(56) References Cited

U.S. PATENT DOCUMENTS

| 6,174,884 B1 | 1/2001 | Haning et al. |
| 6,573,263 B2 | 6/2003 | Niewohner et al. |
| 7,256,199 B1 | 8/2007 | Watanabe et al. |
| 8,569,294 B2 | 10/2013 | Fukunaga et al. |
| 8,598,155 B2 | 12/2013 | Helal et al. |
| 8,680,116 B2 | 3/2014 | DeLeon et al. |
| 2007/0135457 A1 | 6/2007 | Beyer et al. |
| 2012/0214791 A1 | 8/2012 | Helal et al. |
| 2014/0080806 A1 | 3/2014 | Helal et al. |

FOREIGN PATENT DOCUMENTS

| EP | 1097706 A1 | 5/2001 |
| EP | 1097707 A1 | 5/2001 |
| EP | 2231619 | 12/2008 |
| WO | WO2005061497 | 12/2003 |
| WO | WO2005041957 | 10/2004 |
| WO | WO2006024640 | 3/2006 |
| WO | WO200672615 | 7/2006 |
| WO | WO2009016498 | 2/2009 |
| WO | WO2009030998 | 3/2009 |
| WO | WO2010136493 | 12/2010 |
| WO | WO2012054366 | 4/2012 |
| WO | WO2012114222 | 8/2012 |
| WO | WO2013034758 | 9/2012 |
| WO | WO2013034761 | 9/2012 |
| WO | WO2012168817 | 12/2012 |
| WO | WO201300924 | 1/2013 |
| WO | WO2013034755 | 3/2013 |
| WO | WO2013098373 | 7/2013 |
| WO | 2013161913 | 10/2013 |
| WO | WO2014010732 | 1/2014 |
| WO | WO2014019979 | 2/2014 |
| WO | WO2014139983 | 9/2014 |
| WO | WO2015012328 | 1/2015 |
| WO | 2016145614 | 3/2015 |
| WO | WO2015096651 | 7/2015 |
| WO | 2016154081 | 3/2016 |
| WO | WO2005063723 | 7/2017 |

OTHER PUBLICATIONS

Ahlstrom et al., Inactivation of Atrial Natriuretic Factor-Stimulated, Biochemical Pharmacology, 2000, 1133-1139, 59.

(Continued)

*Primary Examiner* — Alicia L Otton
(74) *Attorney, Agent, or Firm* — Sylvia A. Ayler; John C. Todaro

(57) ABSTRACT

The present invention is directed to substituted pyrimidinone compounds of formula (I) which are useful as therapeutic agents for the treatment of central nervous system disorders associated with phosphodiesterase 2 (PDE2). The present invention also relates to the use of such compounds for treating neurological and psychiatric disorders, such as schizophrenia, psychosis, Parkinson's disease, Parkinson's disease dementia (PDD), or Huntington's disease, and those associated with striatal hypofunction or basal ganglia dysfunction.

19 Claims, No Drawings

(56) References Cited

OTHER PUBLICATIONS

Arulomozhi et al., Migraine: Current Therapeutic Targets and Future Avenues, Current Vascular Pharmacology, 2006, 117-128, 4.
Beavo et al., Cyclic GMP as Substrate and Regulator of Cyclic Nucleotide Phosphodiesterases (PDEs), Rev. Physio Biochem Pharm, 1999, 67-104, 135.
Bernard et al., PDE2 Is a Novel Target for Attenuating Tumor Formation in a Mouse Model of UVB-Induced Skin Carcinogenesis, Plos One, 2014, 1-8, 9.
Boess et al., Inhibition of phosphodiesterase 2 increases neuronal cGMP, synaptic plasticity and memory, Neuropharmacology, 2004, 1081-92, 47.
Brandon et al., Potential CNS Applications for, Annual Reports in Medicinal Chemistry, 2007, 3-11, 42.
Bubb et al., Inhibition of Phosphodiesterase 2 Augments cGMP and, Circulation, 2014, 496-507, 268.
Demaria et al., Highlights of the Year in JACC 2013, j. aMER. cOLL. cARD, 2014, 570-602, 63, (6).
Dickinson et al., Activation of cGMP-stimulated phosphodiesterase by nitroprusside limits, Biochem J., 1997, 371-377, 323.
Ding et al., Protective effects of phosphodiesterase 2 inhibitor on depression- and -Anxiety-Like Behaviors: Involvement of antioxidant and anti-apotoic Mechanisms, Behaviorual Brain Research, 2014, 150-158, 268.
Domek-Lopacinska et al., The Effect of Selective Inhibition of Cyclic GMP Hydrolyzing Phosphodiesterases 2 and 5 on Learning and Memory Processes and Nitric Oxide Synthase Activity, Brain Research, 2008, 68-77, 1216.
Ducrot et al., CoMFA and CoMSIA 3D-Quantitative Structure-Activity Relationship Model on Benzodiaepine Derivatives, Inhibitors of Phosphodiesterase IV, J. of Computer Aided Molecular Designs, 2001, 767-785, 15.
Duran et al., The NO cascade, eNOS Location, and Microvascular Permeability, Cardiovascular Research, 2010, 254-261, 87.
Favot et al., VEGF-Induced HUVEC Migration and Proliferation, Schattauer GmbH Stuttgart, 2003, 3443-343, 90.
Gallo, M, et al., Synthesis of 2'-modified nucleoties, Molecules, 2000, pp. 727-729, 5.
Gergega et al., Systematic Effect of Benzo-Annelation on Oxo-Hydroxy Tautomerism of Heterocyclic, J. Phys. Chem A., 2007, 4934-4943, 111.
Giuliano et al., Correction to Tautomerism in 4-Hydroxypyrimidine, S-Methyl-2-thiouracil, and 2-Thiouracil, The Journal of Physical Chemistry A, 2011, 8178-8179, 115.
Giuliano et al., Tautomerism in 4-Hydroxypyrimidine, S-Methyl-2-thiouracil, and 2-Thiouracil, J. Phys. Chem. A, 2010, 12725-12730, 114.
Haynes et al., Erythro-9-(2-Hydroxy-3-Nonyl) Adenine Inhibits Cyclic-3',5' Guanosine Monophosphate-Stimulated Phosphodiesterase to Reverse Hypoxic Pulmonary Vasoconstriction in the Perfused Rat Lung, The J. of Pharmacology, 1996, 752-757, 276.
Herring et al., NO-cGMP Pathway Increases the Hyperpolarisation-Activated Current ,I, and Heart Rate During Adrenergic Stimulation, Cardiovascular Research, 2001, 446-453, 52.
Hiramoto et al., Role of Phosphodiesterase 2 in Growth and Invasion of HUman Maligant Melanoma, Cellular Signaling, 2014, 1807-1817, 26.
Jorgensen et al., Selective Inhibitors of PDE2, PDE9, and PDE10: Modulators of Activity of the Central Nervous System, Annual Reports in Medicinal Chemistry, 2013, pp. 37-55, 48.
Keravis et al., Cyclic Nucleotide Hydrolysis in Bovine Aortic Endothelial Cells in Culture: Differential Regulation in Cobblestone and Spindle Phenotypes, J. Vasc. Res, 2000, 235-249, 37.

Kheifets et al., Structure and Amide-Amide Tautomerism of 4-Hydroxypyrimidines. Determination of the Tautomeric Composition by 13C NMR Spectroscopy, Russ. J. of Organic Chemistry, 2000, 1373-1387, 36, 9.
Lieberman et al., Effectiveness of Antipsychotic Drugs in Patients with Chronic Schizophrenia, New England J. of Medicine, Sep. 22, 2005, pp. 1209-1223, 353, US.
Lopez et al., Solution and solid state (CPMAS) NMR Studies of the Tautomerism of Six-Membered Heterocyclic Compounds Related to 2-Pyridones, Spectroscopy, 2000, pp. 121-126, 14.
Masood et al., Anxiolytic Effects of Phosphodiesterase-2 Inhibitors Associated with Increased cGMP Signaling, J. of Pharmacology, 2009, 690-699, 331.
Masood et al., Reversal of Oxidative Stress-Induced Anxiety by Inhibition of Phosphodiesterase-2 in Mice, J. of Pharmacology and Experimental Therapeutics, 2008, 369-379, 326.
Michie et al., Rapid Regulation of PDE-2 and PDE-4 Cyclic AMP Phosphodiesterase Activity Folloiwng Ligation of the T Cell Antigen Receptor on Thymocytes: Analysis Using theSelctive Inhibitors Erythro-9-(2-Hydroxy-3Nonyl)-Adenine (EHNA) and Rolipram, Cell Signal, 1996, 97-110, 8.
Morita et al., Characterization of Phosphodiesterase 2A in Human Malignant Melanoma PMP Cells, Oncology Reports, 2013, 1275-1284, 29.
Netherton et al., Vascular Endothelial Cell Cyclic Nucleotide phosphodiesterases and Regulated Cell Migration: IMplications in Angiogenesis, Molecular Pharmacology, 2005, 263-272, 67.
P. C. Tfelt-Hansen et al., One Hundred Years of Migraine Research: Major Clinical and, Headache, 2011, 752-778, 51.
Plummer et al., Discovery of Poten, Selective, Bioavailable Phosphodiesterase 2 (PDE2) Inhibitors Active in an Osteoarthritis Pain Model, Part I: Transformation of Selective Pyrazolodiazepinone Phosphodiesterase 4 (PDE4) Inhibitors into Selective PDE2 Inhibitors, Biorganic & Medicinal Chemistry Letters, 2013, 3438-3442, 23.
Plummer et al., Discovery of potent selective bioavailable phosphodiesterase, Bioorganic & Medicinal Chemistry Letters, 2013, 3443-3447, 23.
Reierson et al., Repeated antidepressant therapy increases cyclic GMP signaling, Neurosci Letter, 2009, 149-153, 466 (3).
Rivet-Bastide et al, cGMP-stimulated Cyclic Nucleotide Phosphodiesterase Regulates the Basal, J. Clin. Invest, 1997, 2710-2718, 99.
Sadhu et al., Differential Expression of the Cyclic GMP-Stimulated Phosphodiesterase PDE2A in HUman Venous and Capillary Endothelial Cells, J. of Histochemistry & Cytochemistry, 1999, 895-905, 47.
Sanchez et al., Gas-Phase Tautomeric Equilibrium of 4-Hydroxypyrimidine, J. Am. Chem Soc., 2007, 6287-6290, 129.
Savai et al., Targeting Cancer with Phosphodiesterase Inhibitors, Expert Opinion, 2010, 117-131, 19.
Surapisitchat et al., Differential Regulation of Endothelial Cell Permeability by cGMP via Phosphodiesterases 2 and 3, Circulation Research, 2007, 811-818, 101.
Suvrana et al., Hydrolysis of N-Methyl-D-aspartate Receptor-Stimulated cAMP, J. of Pharmacology, 2002, 249-256, 302.
Van Staveren et al., The effects of phosphodiesterase inhibition on cyclic GMP and cyclic, Brain Research, 2001, 275-286, 888.
Vandecasteele, Cyclic GMP regulation of the L-type Ca2+ channel current, J. of Physiology, 2001, 329-340, 533.
Velardez et al., Role of Phosphodiesterase and Protein Kinase G on Nitric Oxide-Induced Inhibition of Prolactin Relase from the Rat Anterior Pituitary, Europe J. of Endocrinology, 2000, 279-284, 143.
Wakabayashi et al., Involvement of Phosphodiesterase Isozymes in Osteoblastic, J. of Bone and Mineral Research, 2002, 249-253, 17.

HETEROARYL-PYRIMIDINONE COMPOUNDS AS PDE2 INHIBITORS

CROSS REFERENCE TO RELATED APPLICATIONS

This application is the National Stage of International Application No. PCT/US2016/030342 filed on May 2, 2016, which claims the benefit under U.S. Provisional application 62/157,232, filed May 5, 2015.

FIELD OF THE INVENTION

The invention relates generally to compounds which act as inhibitors of the phosphodiesterase (PDE) 2 enzyme, compositions and therapeutic uses thereof.

BACKGROUND OF THE INVENTION

Schizophrenia is a debilitating disorder affecting the psychic and motor functions of the brain. It is typically diagnosed in individuals in their early to mid-twenties and symptoms include hallucinations and delusions or at the other extreme, anhedonia or social withdrawal. Across the spectrum, the symptoms are indicative of cognitive impairment and functional disabilities. Notwithstanding improvements in antipsychotic treatments, current therapies, including typical (haloperidol) and atypical (clozapine or olanzapine) antipsychotics, have been less than acceptable and result in an extremely high rate of noncompliance or discontinuation of medication. Dissatisfaction with therapy is attributed to lack of efficacy or intolerable and unacceptable side effects. The side effects have been associated with significant metabolic, extrapyramidal, prolactic and cardiac adverse events. See, Lieberman et al., N. Engl. J. Med. (2005) 353:1209-1223.

While multiple pathways are believed to be involved with the pathogenesis of schizophrenia leading to psychosis and cognition deficits, much attention has focused on the role of glutamate/NMDA dysfunction associated with cyclic guanosine monophosphate (cGMP) levels and the dopaminergic receptors associated with cyclic adenosine monophosphate (cAMP). These ubiquitous secondary messengers are responsible for altering the function of many intracellular proteins. Cyclic AMP is thought to regulate the activity of cAMP-dependent protein kinase (PKA), which in turn phosphorylates and regulates many types of proteins including ion channels, enzymes and transcription factors. Similarly, cGMP is also responsible for downstream regulation of kinases and ion channels.

One pathway for affecting the levels of cyclic nucleotides, such as cAMP and cGMP, is to alter or regulate the enzymes that degrade these secondary messengers, known as 3', 5'-cyclic nucleotide specific phosphodiesterases (PDEs). The PDE superfamily includes twenty-one genes that encode for eleven families of PDEs. These families are further subdivided based on catalytic domain homology and substrate specificity and include the 1) cAMP specific, PDE4A-D, 7A and 7B, and 8A and 8B, 2) cGMP specific, PDE 5A, 6A-C, and 9A, and 3) those that are dual substrate, PDE 1A-C, 2A, 3A and 3B, 10A, and 11A. The homology between the families, ranging from 20% to 45%, suggests that it may be possible to develop selective inhibitors for each of these families.

PDE2 is highly expressed in the brain, but is also found in many other tissues as well, and therefore has a broad array of function and utility (J. A. Beavo, et al., Rev. Physio. Biochem. Pharm., 135, 67 (1999)). Amongst others, PDE2 has been shown to have therapeutic potential in neuronal development, learning, and memory (W. C. G. van Staveren, et al., Brain Res., 888, 275 (2001) and J. O'Donnell, et al., J. Pharm. Exp. Ther., 302, 249 (2002)); prolactin and aldosterone secretion (M. O. Velardez, et al., Eur. J. Endo., 143, 279 (2000) and N. Gallo-Payet, et al., Endo., 140, 3594 (1999)); bone cell differentiation, growth, and bone resorption (C. Allardt-Lamberg, et al., Biochem. Pharm., 59, 1133 (2000) and S. Wakabayashi, et al., J. Bone, Miner. Res., 17, 249 (2002); immunological response (M. D. Houslay, et al., Cell. Signal., 8, 97 (1996); vascular angiogenesis (T. Keravis, et al., J. Vasc. Res., 37, 235 (2000); inflammatory cell transit (S. L. Wolda, et al., J. Histochem. Cytochem., 47, 895 (1999); cardiac contraction (R. Fischmeister, et al., J. Clin. Invest., 99, 2710 (1997), P. Donzeau-Gouge, et al., J. Physiol., 533, 329 (2001), and D. J. Paterson, et al., Card. Res., 52, 446 (2001); platelet aggregation (R. J. Haslam, et al., Biochem. J., 323, 371 (1997); female sexual arousal disorder (C. P. Wayman, et al., EP Patent Publications EP10977707 and EP1097706); osteoarthritis pain (M. Plummer et. al., Bioorganic & Medicinal Chemistry Letters, 23(11), 3438-3442 and 3443-3447(2013)); malignant melanoma (H. Morita, et al., Oncology Reports, 29, 1275-1284, 2013; Hiramoto, et al., Cell. Signal., 26(9), 1807-1817, 2014; and J. J. Bernard, et al., PloS ONE 9(10): e109862, 2014); heart failure (A. N. DeMaria, et al., J. Amer. Coll. Card. 63 (6), 570-602, 2014); pulmonary hypertension (K. J, Bubb, et al., Circulation, 130, 496-508, 2014); depression and anxiety (L. Ding, et al., Behav. Brain Res. 268, 150-158, 2014); and hypoxic pulmonary vasoconstriction (J. Haynes, et. al., J. Pharm. Exp. Ther., 276, 752 (1996). See also US2007135457.

Inhibition of PDE2 (e.g., PDE2A) has been shown to enhance cognitive function across multiple preclinical models of cognitive performance that reflect improvements in recognition memory, social interactions and working memory, which are all deficient in schizophrenia (Boess et al., *Inhibition of Phosphodiesterase 2 Increases Neuronal cGMP, Synaptic Plasticity and Memory Performance*, Neuropharmacology, 47(7): 1081-92, 2004). PDE2A inhibition was also shown to improve cognitive deficits that develop in aging and Alzheimer's disease (Domek-Lopacinska and Strosznajder, *The Effect of Selective Inhibition of Cyclic GMP Hydrolyzing Phosphodiesterases 2 and 5 on Learning and Memory Processes and Nitric Oxide Synthetase Activity in Brain During Aging*, Brain Research, 1216:68-77, 2008). The role of PDE2 inhibition in cognitive disorders was also shown in Brandon et al., *Potential CNS Applications for Phosphodiesterase Enzyme Inhibitors*, Annual Reports in Medicinal Chemistry 42: 4-5, 2007 (compound BAY 60-7550 was reported to have significant potency at other PDE isoforms, had high clearance and limited brain penetration).

See also Jorgenson, et al, Annual Reports in Medicinal Chemistry 48: 37-55, 2013. "Selective Inhibitors of PDE2, PDE9, and PDE10: Modulators of Activity of the Central Nervous System". PDE2 inhibitors have also been shown to have efficacy in preclinical models of anxiety and depression (Masood et al., Anxiolytic Effects of Phosphodiesterase-2 Inhibitors Associated with Increased cGMP Signaling, JPET 331(2):690-699, 2009; Masood et al., Reversal of Oxidative Stress-Induced Anxiety by Inhibition of Phosphodiesterase-2 in Mice, JPET 326(2):369-379, 2008; Reierson et al., Repeated Antidepressant Therapy Increases Cyclic GMP Signaling in Rat Hippocampus, Neurosci. Lett., 466(3):149-53, 2009). See also Ducrot et al., CoMFA and CoMSIA 3D-quantitative structure-activity relationship model on benzodiazepine derivatives, inhibitors of phosphodieserase IV, J Computer-Aided Molecular Design, 15: 767785, 2001; US20120214791; WO2012168817; WO2013034755; WO2013034758; WO2013034761; WO2005041957; WO2005061497; WO2006024640; WO2013161913; WO2010136493; WO 2013098373; WO 2009016498; U.S. Pat. Nos. 6,573,263; 8,598,155; and 8,680,116; WO2015012328; WO2014139983; WO2014019979; WO2014010732; WO2013000924; WO2012114222; WO2006072615; WO2005063723; M. Plummer et al., Bioorg Med Chem Lett 23(11), 3438, 2013; and M. Plummer et al., Bioorg Med Chem Lett 23(11), 3443, 2013.

An increase in vascular permeability has been shown to be attributable to increased activity of PDE2. PDE2 and PDE3 in the endothelium can act as a sensor or switch to detect normal versus pathological concentrations of cGMP and thus regulate endothelial permeability accordingly with potential relevance to migraine. See Surapisitchat et al., *Differential Regulation of Endothelial Cell Permeability by cGMP via Phosphodieserase 2 and 3*, Circulation Research, 2007; 101, pgs.: 811-818 and Duran et al., *The NO Cascade, eNOS Location and Microvascular Permeability*, Cardiovascular Res. (2010) 87, 254-261. Cerebral vasodilation is considered a major cause of migraine. See P. C. Tfelt-Hansen and P. J. Koehler, *One hundred years of migraine research: major clinical and scientific observations from 1910 to 2010*, Headache, 2011. 51(5), 752-578 and D. K. Arulmozhi et al., *Migraine: current therapeutic targets and future avenues*, Current Vascular Pharmacology, 2006, 4(2), 117-128. Therefore, PDE2 inhibition may have utility as a treatment or prophylactic for migraine.

The need for new and improved PDE2 modulators believed to be useful for treating diseases or disorders associated with PDE2 such as Alzheimer's disease, cognitive impairment associated with schizophrenia, depression, migraines, Parkinson's disease, Parkinson's disease dementia (PDD) and the like continues to exist. Inhibitors of PDE2 are not only believed to be useful in treating schizophrenia but also a wide variety of conditions or disorders that would benefit from increasing levels of cAMP and/or cGMP within neurons, including a variety neurological, psychotic, anxiety and/or movement disorders. Accordingly, agents that inhibit PDE2 and PDE2A would be desirable as therapeutics for neurological and psychiatric disorders.

SUMMARY OF THE INVENTION

The present invention is directed to heteroaryl-pyrimidinone compounds which may be useful as therapeutic agents for the treatment of central nervous system and/or peripheral disorders associated with phosphodiesterase 2 (PDE2). The present invention also relates to the use of such compounds for treating neurological and psychiatric disorders, such as schizophrenia, psychosis, Alzheimer's, cognitive impairment, anxiety, depression, migraines, or Huntington's disease, Parkinson's disease, Parkinson's disease dementia (PDD), and other diseases associated with striatal hypofunction or basal ganglia dysfunction.

DETAILED DESCRIPTION OF THE INVENTION

The present invention is directed to heteroaryl pyrimidinone compounds of formula I:

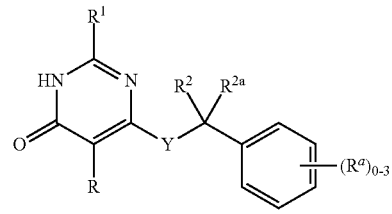

or a pharmaceutically acceptable salt thereof, wherein:
$R^1$ is selected from the group consisting of hydrogen, $C_{1-6}$alkyl, $C_{3-10}$cycloalkyl, and $(CH_2)_nC_{6-10}$aryl, said alkyl, cycloalkyl, and aryl optionally substituted with one to three groups of $R^a$;
$R^2$ and $R^{2a}$ are independently selected from the group consisting of hydrogen, $C_{1-6}$alkyl, $C_{2-6}$alkenyl, $(CH_2)_nOR$, $C(O)OR$, $N(R)_2C_{3-10}$ cycloalkyl, $(CH_2)_nC_{5-10}$heterocyclyl said alkyl, cycloalkyl, and heterocyclyloptionally substituted with one to three groups of $R^b$;
$R^2$ and $R^{2a}$ can combine with the carbon atom to which they are attached to form a $C_{2-6}$ alkenyl, $C_{3-6}$ cycloalkyl, or $C_{4-10}$ heterocyclyl, said alkenyl, cycloalkyl and heterocyclyl optionally substituted with one to three groups of $R^b$;
Y is $C_{5-10}$ heteroaryl selected from the group consisting of pyridyl, pyrimidinyl, pyrazinyl, pyridazinyl, oxazolyl, oxadiazolyl, thiazolyl, thiadiazolyl, and imidazolyl, said group optionally substituted with one to three groups of $R^b$;
R represents H, or $C_{1-6}$ alkyl,
$R^a$ is selected from the group consisting of halo, CN, $C_{1-6}$alkyl, $(CH_2)_nOR$, $(O)_pC_{1-4}$haloalkyl, $C(O)OR$, $-O(CH_2)_nN(R)_2$, $(CHR)_nN(R)_2$, $NO_2$, $SCF_3$, $S(O)_sCF_3$, $S(O)_sR$, $SF_5$, $C_{3-10}$cycloalkyl, $O-C_{3-10}$ cycloalkyl, $C_{5-10}$heterocyclyl, and $C_{6-10}$aryl, said alkyl, cycloalkyl, heterocyclyl and aryl optionally substituted with one to three groups of $R^b$;
$R^b$ is selected from the group consisting of halo, $C_{1-6}$alkyl, $(CH_2)_nOR$, and $(O)_pC_{1-4}$haloalkyl;
n represents 0, 1, 2, 3, or 4;
s represents 0, 1, or 2; and
p represents 0 or 1.

It should be understood that the heteroaryl of Y may be substituted with up to three groups of $R^b$ when it is chemically feasible to do so.

An embodiment of the invention of formula I is realized when Y is an optionally substituted six membered heterocycle selected from the group consisting of pyridyl, pyrimidinyl, pyrazinyl, and pyridazinyl. A subembodiment of the invention of formula I is realized when Y is an unsubstituted six membered heterocycle selected from the group consisting of pyridyl, pyrimidinyl, pyrazinyl, and pyridazinyl. A subembodiment of this aspect of the invention is realized when the optionally substituted pyridyl, pyrimidinyl, pyrazinyl, and pyridazinyl of Y are represented by structural formulas (a), (b), (c), (d), (e), (f), (g), (h), (i) and (j):

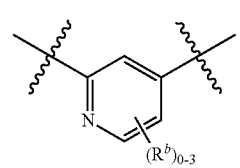

(a)

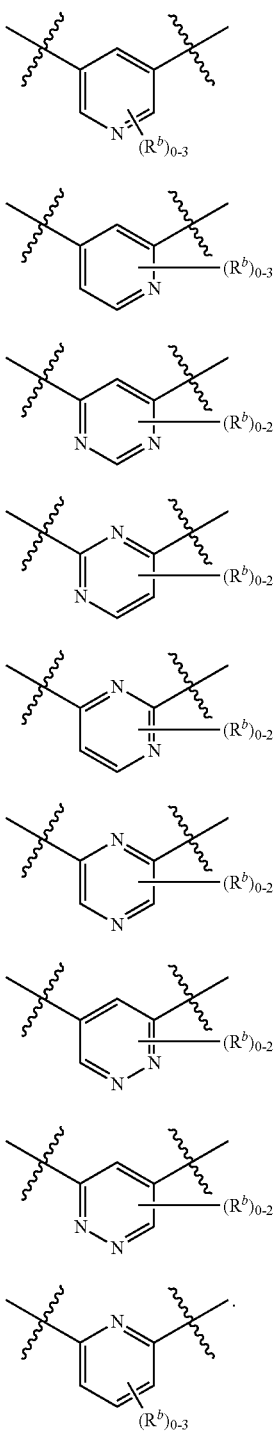

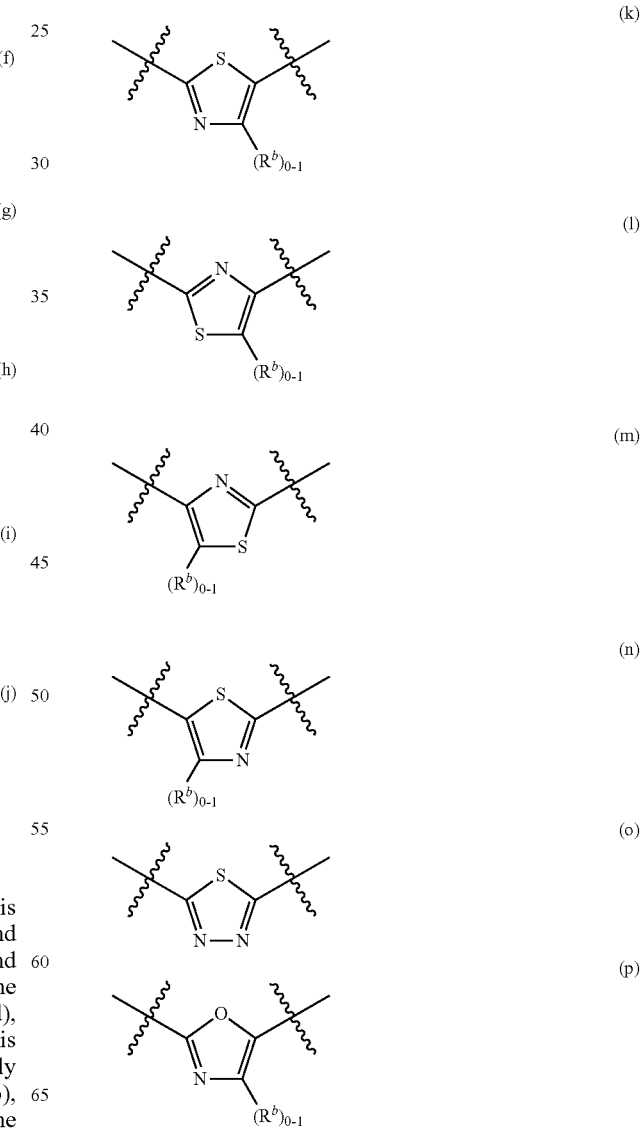

idinyl represented by structural formula (d), (e), or (f). Another subembodiment of this aspect of the invention is realized when Y is optionally substituted pyrazinyl represented by structural formula (g). Still another subembodiment of this aspect of the invention is realized when Y is optionally substituted pyridazinyl represented by structural formula (h) or (i).

Another embodiment of the invention of formula I is realized when Y is an optionally substituted five membered heterocycle selected from the group consisting of oxazolyl, oxadiazolyl, thiazolyl, thiadiazolyl, imidazolyl, isoxazolyl, and isothiazolyl. A subembodiment of the invention of formula I is realized when Y is an unsubstituted five membered heterocycle selected from the group consisting of oxazolyl, oxadiazolyl, thiazolyl, thiadiazolyl, and imidazolyl. A subembodiment of this aspect of the invention is realized when the optionally substituted oxazolyl, oxadiazolyl, thiazolyl, thiadiazolyl, and imidazolyl of Y are represented by structural formulas (k), (l), (m), (n), (o), (p), (q), (r), (s), (t), (u), (v), and (w):

Another subembodiment of this aspect of the invention is realized when $R^b$ in (a), (b), (c), (d), (e), (f), (g), (h), (i) and (j) is absent as represented by "0" in the term "$(R^b)$ 0-3" and "$(R^b)$ 0-2". Another subembodiment of this aspect of the invention is realized when there is one $R^b$ in (a), (b), (c), (d), (e), (f), (g), (h), (i), and (j). Another subembodiment of this aspect of the invention is realized when Y is optionally substituted pyridyl represented by structural formula (a), (b), (c), or (j). Another subembodiment of this aspect of the invention is realized when Y is optionally substituted pyrim-

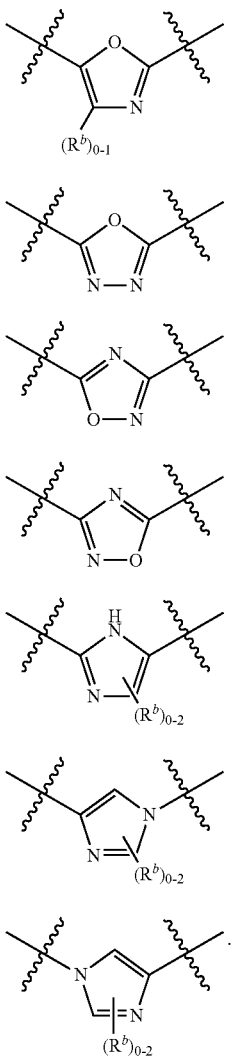

Another subembodiment of this aspect of the invention is realized when $R^b$ in (k), (1), (m), (n), (p), (q), (u), (v), and (w) is absent as represented by "0" in the term "$(R^b)_{0-1}$" and "$(R^b)_{0-2}$". Another subembodiment of this aspect of the invention is realized when there is one $R^b$ in (k), (1), (m), (n), (p), (q), (u), (v), and (w). Another subembodiment of this aspect of the invention is realized when Y is optionally substituted thiazolyl represented by structural formula (k), (l), (m), or (n). Another subembodiment of this aspect of the invention is realized when Y is thiadiazolyl represented by structural formula (o). Another subembodiment of this aspect of the invention is realized when Y is optionally substituted oxazolyl represented by structural formula (p) or (q). Still another subembodiment of this aspect of the invention is realized when Y is oxadiazolyl represented by structural formula (r), (s) or (t). Still another subembodiment of this aspect of the invention is realized when Y is optionally substituted imidazolyl represented by structural formula (u), (v) or (w).

Another embodiment of the invention is realized when R represents H.

Still another embodiment of the invention is realized when R represents optionally substituted $C_{1-6}$ alkyl.

Another embodiment of the invention is realized when $R^1$ is hydrogen.

Another embodiment of the invention is realized when $R^1$ is optionally substituted $C_{1-6}$ alkyl. An aspect of this embodiment of the invention is realized when $R^1$ is optionally substituted methyl, ethyl, isopropyl, propyl, butyl, isobutyl, pentyl and the like. Still another aspect of this embodiment of the invention is realized when $R^1$ is methyl.

Still another embodiment of the invention is realized when $R^1$ is $(CH_2)_n C_{3-10}$cycloalkyl. An aspect of this embodiment of the invention is realized when $R^1$ is cyclopropyl, cyclobutyl, cyclopentyl, cyclohexyl and the like.

Yet another embodiment of the invention is realized when $R^1$ is $(CH_2)_n C_{6-10}$ aryl. An aspect of this embodiment of the invention is realized when the aryl of $R^1$ is optionally substituted phenyl.

Another embodiment of the invention is realized when $R^2$ and $R^{2a}$ independently are selected from H, methyl, ethyl, propyl, isopropyl, butyl, isobutyl, pentyl, $(CH_2)_n OH$, OR, $C(O)OR$, $NHCH_3$, $NH_2$, $NHCH_2CH_3$, $(CH_2)_n OCH_3$, $O(CH_2)_n CH_3$, cyclopropyl, cyclobutyl, and tetrahydrofuranyl said methyl, ethyl, propyl, isopropyl, butyl, isobutyl, pentyl cyclopropyl, cyclobutyl, and tetrahydrofuranyl optionally substituted with one to three groups of $R^b$.

Another embodiment of the invention is realized when one of $R^2$ and $R^{2a}$ is hydrogen and the other is $(CH_2)_n CH_3$, $CH(CH_3)_2$, $(CH_2)_n OH$, $C(O)OCH_3$, $NHCH_3$, $(CH_2)_n(OCH_3)$, and optionally substituted cyclopropyl, cyclobutyl, and tetrahydrofuranyl. An aspect of this embodiment of the invention is realized when one of $R^2$ and $R^{2a}$ is hydrogen and the other is $(CH_2)_n CH_3$. A further aspect of this embodiment of the invention is realized when one of $R^2$ and $R^{2a}$ is hydrogen and the other is $CH_3$.

Another embodiment of the invention is realized when both $R^2$ and $R^{2a}$ are optionally substituted $C_{1-6}$alkyl. A subembodiment of this aspect of the invention is realized when both $R^2$ and $R^{2a}$ are optionally substituted methyl.

Still another embodiment of the invention is realized when $R^2$ and $R^{2a}$ together with the carbon atom to which they are attached are combined to form a group selected from $C_{3-6}$ cycloalkyl and $C_{3-10}$ heterocyclyl. Another aspect of this aspect of the invention is realized when $R^2$ and $R^{2a}$ together with the carbon atom to which they are attached form $C_{3-6}$ cycloalkyl, selected from the group consisting of cyclopropyl, cyclobutyl, cyclopentyl, cyclohexyl, and the like. Another aspect of this aspect of the invention is realized when $R^2$ and $R^{2a}$ together with the carbon atom to which they are attached form $C_{3-10}$ heterocyclyl such as tetrahydrofuranyl.

Another embodiment of the invention of formula I is realized when $R^a$ is selected from H, OH, halo, $(CH_2)_n CH_3$, $CH(CH_3)_2$, $C(CH_3)_3$, $C(O)OCH_3$, $(CH_2)_n OCH_3$, $OC(CH_3)_2$, $CF_2R$, $CH_2F$, $CHF_2$, $(CH_2)_n CF_3$, $OCHF_2$, $OCF_3$, $SCH_3$, $SCF_3$, $SF_5$, $SOCF_3$, $SO_2CF_3$, $SO_2CH_3$, $CH_2NH_2$, $(CH_2)_n N(CH_3)_2$, $NO_2$, CN, cyclobutyl, cyclopropyl, phenyl, naphthyl, pyrimidinyl, pyridyl, said groups, where appropriate, optionally substituted with one to three groups of $R^b$. Another embodiment of the invention of formula I is realized when $R^a$ is selected from OH, halo, $(CH_2)_n CH_3$, $CH(CH_3)_2$, $C(CH_3)_3$, $(CH_2)_n OCH_3$, $OC(CH_3)_2$, $CH_2F$, $CHF_2$, $CF_3$, $OCHF_2$, $OCF_3$, $SCH_3$, $SCF_3$, $SF_5$, $SOCF_3$, $SO_2CF_3$, $SO_2CH_3$, $CH_2NH_2$, $(CH_2)_n N(CH_3)_2$, $NO_2$, CN, cyclobutyl, cyclopropyl, and phenyl, said groups, where appropriate, optionally substituted with one to three groups of $R^b$.

Another embodiment of the invention of formula I is realized when the $R^a$ on the phenyl group of formula I is selected from the group consisting of halo, $(CH_2)_nCH_3$, $CH_2F$, $(CH_2)_nCF_3$, $OCHF_2$, $OCF_3$, and $SF_5$.

Another aspect of this embodiment of the invention is realized when the phenyl group of formula I is substituted with at least two $R^a$ groups. Still another aspect of this embodiment of the invention is realized when the phenyl group of formula I is substituted with at least two $R^a$ groups selected from $CF_3$ and halo. Still another aspect of this embodiment of the invention is realized when the phenyl group of formula I is substituted with one $R^a$ group which is $CF_3$.

Another embodiment of the invention of formula I is realized when n is 0. Another embodiment of the invention of formula I is realized when n is 1. Another embodiment of the invention of formula I is realized when n is 2. Another embodiment of the invention of formula I is realized when n is 3. Still another embodiment of the invention of formula I is realized when n of $R^a$ is 0-1, 0-2, or 0-3.

Another aspect of the invention of formula I is realized when R is hydrogen, Y is pyridyl (a), (b), or (c), the number of $R^b$ present on the pyridyl is zero, $R^1$ is optionally substituted methyl and one of $R^2$ and $R^{2a}$ is hydrogen and the other is $(CH_2)_nCH_3$.

Another aspect of the invention of formula I is realized when R is hydrogen, Y is pyrimidinyl (d), (e), or (f), the number of $R^b$ present on the pyrimidinyl is zero, $R^1$ is optionally substituted methyl and one of $R^2$ and $R^{2a}$ is hydrogen and the other is $(CH_2)_nCH_3$.

Another aspect of the invention of formula I is realized when R is hydrogen, Y is pyrazinyl (h) or (i) and the number of $R^b$ present on the pyrazinyl is zero, $R^1$ is optionally substituted methyl and one of $R^2$ and $R^{2a}$ is hydrogen and the other is $(CH_2)_nCH_3$.

Another aspect of the invention of formula I is realized when R is hydrogen, Y is pyridazinyl (g), the number of $R^b$ present on the pyridazinyl is zero, $R^1$ is optionally substituted methyl and one of $R^2$ and $R^{2a}$ is hydrogen and the other is $(CH_2)_nCH_3$.

Another aspect of the invention of formula I is realized when R is hydrogen, Y is thiazolyl (k), (l), (m) or (n), the number of $R^b$ present on the thiazolyl is zero, $R^1$ is optionally substituted methyl and one of $R^2$ and $R^{2a}$ is hydrogen and the other is $(CH_2)_nCH_3$.

Another aspect of the invention of formula I is realized when R is hydrogen, Y is thiadiazolyl (o), the number of $R^b$ present on the thiadiazolyl is zero, $R^1$ is optionally substituted methyl and one of $R^2$ and $R^{2a}$ is hydrogen and the other is $(CH_2)_nCH_3$.

Another aspect of the invention of formula I is realized when R is hydrogen, Y is oxazolyl (p) or (q), the number of $R^b$ present on the oxazolyl is zero, $R^1$ is optionally substituted methyl and one of $R^2$ and $R^{2a}$ is hydrogen and the other is $(CH_2)_nCH_3$.

Another aspect of the invention of formula I is realized when R is hydrogen, Y is oxadiazolyl (r), (s), or (t), the number of $R^b$ present on the oxadiazolyl is zero, $R^1$ is optionally substituted methyl and one of $R^2$ and $R^{2a}$ is hydrogen and the other is $(CH_2)_nCH_3$.

Another aspect of the invention of formula I is realized when R is hydrogen, Y is imidazolyl (u), (v) or (w), the number of $R^b$ present on the imidazolyl is zero, $R^1$ is optionally substituted methyl and one of $R^2$ and $R^{2a}$ is hydrogen and the other is $(CH_2)_nCH_3$.

The invention is also directed to a method for the treatment of central nervous system disorders associated with phosphodiesterase 2 (PDE2) using the compounds of Formula I. More specifically, the present invention relates to the use of such compounds for treating neurological and psychiatric disorders, such as schizophrenia, psychosis, Alzheimer's, cognitive impairment, anxiety, depression, migraines, or Huntington's disease, Parkinson's disease, Parkinson's disease dementia, and other diseases associated with striatal hypofunction or basal ganglia dysfunction using the compounds of formula I.

Examples of compounds of the invention can be found throughout the specification.

The invention also encompasses pharmaceutical compositions containing a compound of formula I and methods for treatment or prevention of phosphodiesterase mediated diseases using compounds of formula I.

Where a variable occurs more than once in any formula of the invention, or in a substituent thereof, the individual occurrences of that variable are independent of each other, unless otherwise specified. Also, combinations of substituents/or variables are permissible only if such combinations result in stable compounds and valency permits.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six atoms. Exemplary alkyl groups include methyl, ethyl, n-propyl, isopropyl, n-butyl, isobutyl, tert-butyl, pentyl, hexyl, and the like. $C_0$ alkyl means a bond.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, spirocycles, and bridged and fused ring carbocycles.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantyl and norbornyl. Exemplary fused cycloalkyl groups include decahydronaphthalene.

As used herein, the term "aryl," by itself or as part of another substituent, means an aromatic cyclic hydrocarbon radical. Preferred aryl groups have from six to ten carbons atoms. The term "aryl" includes multiple ring systems as well as single ring systems. Preferred aryl groups for use in the invention include phenyl and naphthyl.

The term "aryl" also includes fused cyclic hydrocarbon rings which are partially aromatic (i.e., one of the fused rings is aromatic and the other is non-aromatic). An exemplary aryl group which is partially aromatic is indanyl.

The term heterocyclyl, heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocyclyl, heterocycle or heterocyclic includes heteroaryl moieties. Examples of such heterocyclic elements include, but are not limited to, azepinyl, benzodioxolyl, benzimidazolyl, benzisoxazolyl, benzofurazanyl, benzopyranyl, benzothiopyranyl, benzofuryl, benzothiazolyl, benzothienyl, benzotriazolyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyrazolopyridinyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl, and triazolyl. The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure.

When a heterocyclyl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

As used herein, the term "halo" or "halogen" includes fluoro, chloro, bromo and iodo. The term "haloalkyl" means an alkyl, as defined above, wherein one or more of the bonding positions on the alkyl moiety typically occupied by hydrogen atoms are instead occupied by a halo group, perhaloalkyl (or "fully halogenated" alkyl) means that all bonding positions not participating in bonding the alkyl substituent to a substrate are occupied by a halogen, for example, where the alkyl is selected to be methyl, the term perfluoroalkyl means —$CF_3$.

The compounds of the invention may have one or more asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of the invention. The present invention includes all stereoisomers of formulae (I) and pharmaceutically acceptable salts thereof.

It should be appreciated by any one skilled in the art that the compounds of this invention can exist in several tautomeric forms as shown below:

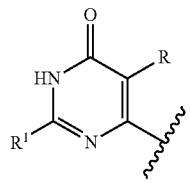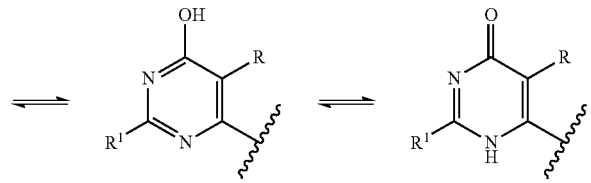

Previous researchers have studied similar compounds and found that one of these tautomers can exist as the predominant form depending on structures and conditions. See B. M. Giuliano, et al. J. Phys. Chem. A, 114, 12725-12730, 2010; B. M. Giuliano, et al. J. Phys. Chem. A, 115, 8178-8179, 2011; A. Gerega, et al. J. Phys. Chem. A, 111, 4934-4943, 2007; R. Sanchez, et al., J. Amer. Chem. Soc., 129(19), 6287-6290, 2007; C. Lopez, et al., Spectroscopy 14, 121-126, 2000; and G. M. Kheifets, et al., Russ. J. Org. Chem., 36(9), 1373-1387, 2000. For brevity and simplicity, we have represented the compounds of the present invention using Formula I and they are intended to represent all possible tautomeric forms for these compounds without regard to what actually is the predominant tautomeric form in existence for a particular compound.

One or more compounds of the invention may exist in unsolvated as well as solvated forms with pharmaceutically acceptable solvents such as water, ethanol, and the like, and it is intended that the invention embrace both both solvated and unsolvated forms. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates and the like. "Hydrate" is a solvate wherein the solvent molecule is $H_2O$.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of the compound bound to PDE2 enzyme, of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

In the compounds of the invention the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic formula I and Ia. For example, different isotopic forms of hydrogen (H) include protium (1H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically enriched compounds within generic formula I and Ia can be prepared without undue experimentation by conventional techniques well known to those skilled in the art or by processes analogous to those described in the Schemes and Examples herein using appropriate isotopically enriched reagents and/or intermediates.

The term "substantially pure" means that the isolated material is at least 90% pure, and preferably 95% pure, and even more preferably 99% pure as assayed by analytical techniques known in the art.

For purposes of this specification, the following abbreviations have the indicated meanings:

Ac=acetyl
ACN=acetonitrile
AcO=acetate
BOC=t-butyloxycarbonyl
CBZ=carbobenzoxy
CDI=carbonyldiimidazole
DBU=1,8-Diazabicycloundec-7-ene
DCC=1,3-dicyclohexylcarbodiimide
DCE=1,2-dichloroethane
(dF(CF$_3$)ppy)=2-(2,4-difluorophenyl)-5-trifluoromethylpyridine
DI=de-ionized
DIAD=Diisopropyl azodicarboxylate
DIBAL=diisobutyl aluminum hydride
DIPEA or DIEA=N,N-diisoproylethylamine, also known as Hunig's base
DMA=dimethylacetamide
DMAP=4-(dimethylamino)pyridine
DMF=dimethylformamide
DMP=Dess-Martin periodinane
DPPA=Diphenylphosphoryl azide
DPPP=1,3-bis(diphenylphosphino)propane
Dtbbpy=4,4'-di-tert-butyl-2,2'-dipyridyl
EDC or EDCI=1-(3-dimethylaminopropyl)-3-ethylcarbodiimide hydrochloride
EDTA=ethylenediaminetetraacetic acid, tetrasodium salt
EtOAc=ethyl acetate
FAB=fast atom bombardment
FMOC=9-fluorenylmethoxycarbonyl
HMPA=hexamethylphosphoramide
HATU=O-(7-Azabenzotriazol-1-yl)-N,N,N',N'-tetramethyluronium hexafluorophosphate
HOAt=1-Hydroxy-7-azabenzotriazole or 3H-[1,2,3]triazolo[4,5-b]pyridin-3-ol
HOBt=1-hydroxybenzotriazole
HRMS=high resolution mass spectrometry
IBCF=isobutyl chloroformate
KHMDS=potassium hexamethyldisilazane
LC-MS=Liquid chromatography-mass spectrometry
LDA=lithium diisopropylamide
LiHMDS=lithium hexamethyldisilazane
MCPBA=metachloroperbenzoic acid
MMPP=magnesium monoperoxyphthlate hexahydrate
Ms=methanesulfonyl=mesyl
MsO=methanefulfonate=mesylate
MTBE=Methyl t-butyl ether
NBS=N-bromosuccinimide
NMM=4-methylmorpholine
NMP=N-methylpyrrolidinone
NMR=Nuclear magnetic resonance
PCC=pyridinium chlorochromate
PDC=pyridinium dichromate
Ph=phenyl
PPTS=pyridinium p-toluene sulfonate
pTSA=p-toluene sulfonic acid
PyH.Br$_3$=pyridine hydrobromide perbromide
r.t./RT=room temperature
rac.=racemic
T3P=2,4,6-Tripropyl-1,3,5,2,4,6-trioxatriphosphinane 2,4,6-trioxide
TEA=triethylamine
TFA=trifluoroacetic acid
TfO=trifluoromethanesulfonate=triflate
THF=tetrahydrofuran
TLC=thin layer chromatography
TMSCl=trimethylsilyl chloride The compounds of the present invention may contain one or more stereogenic centers and can thus occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

All patents, patent applications and publications cited herein, whether supra or infra, are hereby incorporated by reference in their entirety and are deemed representative of the prevailing state of the art.

It will be understood that, as used herein, references to the compounds of present invention are meant to also include the pharmaceutically acceptable salts, and also salts that are not pharmaceutically acceptable when they are used as precursors to the free compounds or in other synthetic manipulations. The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, cupric, cuprous, ferric, ferrous, lithium, magnesium, manganic, manganous, potassium, sodium, zinc and the like salts. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments are citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

Exemplifying the invention are the specific compounds disclosed in the Examples and herein. The subject compounds may be useful in a method of treating a neurological or psychiatric disorder associated with PDE2 dysfunction in a patient such as a mammal in need of such inhibition comprising the administration of an effective amount of the compound. In addition to primates, especially humans, a variety of other mammals can be treated according to the method of the present invention. The subject compounds may be useful in a method of inhibiting PDE2 activity in a patient such as a mammal in need of such inhibition comprising the administration of an effective amount of the compound. The subject compounds also may be useful for treating a neurological or psychiatric disorder associated with striatal hypofunction or basal ganglia dysfunction in a mammalian patient in need thereof. In addition to primates, especially humans, a variety of other mammals can be treated according to the method of the present invention.

The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for treating a neurological or psychiatric disorder associated with PDE2 function in a mammalian patient in need thereof. The present invention is further directed to a use of a compound of the present invention or a pharmaceutically acceptable salt thereof for the manufacture of a medicament for treating a neurological or psychiatric disorder associated with striatal hypofunction or basal ganglia dysfunction in a mammalian patient in need thereof.

"Treating" or "treatment of" a disease state includes: 1) inhibiting the disease state, i.e., arresting the development of the disease state or its clinical symptoms; 2) or relieving the disease state, i.e., causing temporary or permanent regression of the disease state or its clinical symptoms.

The subject treated in the present methods is generally a mammal, in particular, a human being, male or female, in whom therapy is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention.

Applicants propose that inhibitors of PDE2, including PDE2A, will provide therapeutic benefit to those individuals suffering from psychiatric and cognitive disorders. The unique and exclusive distribution of PDE2A in the medium spiny projection neurons of the striatum, which form the principle site for cortical and dopaminergic input within basal ganglia, suggests that it may be possible and desirable to identify inhibitors of PDE2 to enhance cellular signaling. Without wishing to be bound by any theory, applicants believe that inhibition of PDE2A in the striatum will result in increased cAMP/cGMP signaling and striatal output, which has the potential to restore behavioral inhibition that is impaired in cognitive disease such as schizophrenia. Regulation and integration of glutamatergic and dopaminergic inputs will enhance cognitive behavior, while suppressing or reducing unwanted behavior. Thus, in one embodiment, compounds of the invention provide a method for treating or ameliorating diseases or conditions in which striatal hypofunction is a prominent feature or ones in which basal ganglia dysfunction plays a role, such as, Parkinson's disease, Parkinson's disease dementia (PDD), Huntington's disease, schizophrenia, obsessive-compulsive disorders, addiction and psychosis. Other conditions for which the inhibitors described herein may have a desirable and useful effect include those requiring a reduction in activity and reduced response to psychomotor stimulants or where it would be desirable to reduce conditional avoidance responses, which is often predictive of clinical antipsychotic activity.

In another embodiment the compounds of this invention there is provided a method for treating or ameliorating diseases or conditions in neuronal development, learning, and memory, prolactin and aldosterone secretion, bone cell differentiation, growth, and bone resorption, immunological response, vascular angiogenesis, inflammatory cell transit, cardiac contraction, platelet aggregation, female sexual arousal disorder, and hypoxic pulmonary vasoconstriction.

As used herein, the term "selective PDE2 inhibitor" refers to an organic molecule that effectively inhibits an enzyme from the PDE2 family to a greater extent than enzymes from the PDE 1, and 3-11 families. In one embodiment, a selective PDE2 inhibitor is an organic molecule having a Ki for inhibition of PDE2 that is less than or about one-tenth that for a substance that is an inhibitor for another PDE enzyme. In other words, the organic molecule inhibits PDE2 activity to the same degree at a concentration of about one-tenth or less than the concentration required for any other PDE enzyme. Preferably, a selective PDE2 inhibitor is an organic molecule, having a Ki for inhibition of PDE2 that is less than or about one-hundredth that for a substance that is an inhibitor for another PDE enzyme. In other words, the organic molecule inhibits PDE2 activity to the same degree at a concentration of about one-hundredth or less than the concentration required for any other PDE enzyme. Preferably, a selective PDE2 inhibitor is an organic molecule, having a Ki for inhibition of PDE2 that is less than or about five-hundredth that for a substance that is an inhibitor for another PDE enzyme. In other words, the organic molecule inhibits PDE2 activity to the same degree at a concentration of about five-hundredth or less than the concentration required for any other PDE enzyme. A "selective PDE2 inhibitor" can be identified, for example, by comparing the ability of an organic molecule to inhibit PDE2 activity to its ability to inhibit PDE enzymes from the other PDE families. For example, an organic molecule may be assayed for its ability to inhibit PDE2 activity, as well as PDE1A, PDE1B, PDE1C, PDE3A, PDE3B, PDE4A, PDE4B, PDE4C, PDE4D, PDE5A, PDE6A, PDE6B, PDE6C, PDE7A, PDE7B, PDE8A, PDE8B, PDE9A, PDE10 and/or PDE11A.

Phosphodiesterase enzymes including PDE2 have been implicated in a wide range of biological functions. This has suggested a potential role for these enzymes in a variety of disease processes in humans or other species. The compounds of the present invention may have utility in treating a variety of neurological and psychiatric disorders.

In a specific embodiment, compounds of the present invention provide a method for treating schizophrenia or psychosis comprising administering to a patient in need thereof an effective amount of a compound of the present invention. The Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, *cannabis*, cocaine, hallucinogens, inhalants, opioids, phencyclidine, ketamine and other dissociative anaesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, the compounds of the present invention provide a method for treating cognitive disorders comprising administering to a patient in need thereof an effective amount of a compound of the present invention. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Parkinson's disease dementia (PDD), Huntington's disease, Pick's disease, Creutzfeldt Jacob disease, perinatal hypoxia, other general medical conditions or substance abuse), Alzheimer's disease, multi-infarct dementia, AIDS-related dementia, and Fronto temporal dementia, delirium, amnestic disorders or age related cognitive decline.

In another specific embodiment, compounds of the present invention provide a method for treating anxiety disorders comprising administering to a patient in need thereof an effective amount of a compound of the present invention. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another specific embodiment, compounds of the present invention provide a method for treating substance-related disorders and addictive behaviors comprising administering to a patient in need thereof an effective amount of a compound of the present invention. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, *cannabis*, cocaine, hallucinogens, inhalants, nicotine, opioids, phencyclidine, sedatives, hypnotics or anxiolytics.

In another specific embodiment, compounds of the present invention provide a method for treating obesity or eating disorders associated with excessive food intake, and complications associated therewith, comprising administering to a patient in need thereof an effective amount of a compound of the present invention. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-2 and DSM-IV-TR and the term is intended to include similar disorders described in other sources. Disorders and conditions encompassed herein include, but are not limited to, obesity, bulimia nervosa and compulsive eating disorders.

In another specific embodiment, compounds of the present invention provide a method for treating mood and depressive disorders comprising administering to a patient in need thereof an effective amount of a compound of the present invention. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with post-partum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder, mood disorders due to a general medical condition, and substance-induced mood disorders.

In another specific embodiment, compounds of the present invention provide a method for treating pain comprising administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In other specific embodiments, compounds of the invention provide methods for treating other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with cerebral trauma, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, Parkinson's disease dementia (PDD), drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemiballism), myoclonus (including, generalised myoclonus and focal myoclonus), tics (including, simple tics, complex tics and symptomatic tics), dystonia (including, generalised, iodiopathic, drug-induced, symptomatic, paroxymal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy.

Of the disorders above, the treatment of schizophrenia, bipolar disorder, depression, including unipolar depression, seasonal depression and post-partum depression, premenstrual syndrome (PMS) and premenstrual dysphoric disorder, learning disorders, pervasive developmental disorders, including autistic disorder, attention disorders including Attention-Deficit/Hyperactivity Disorder, autism, tic disorders including Tourette's disorder, anxiety disorders including phobia and post-traumatic stress disorder, cognitive disorders associated with dementia, AIDS dementia, Alzheimer's, Parkinson's disease, Parkinson's disease dementia, Huntington's disease, spasticity, myoclonus, muscle spasm, tinnitus and hearing impairment and loss are of particular importance.

Angiogenesis is the physiological process through which new blood vessels form, and agents that inhibit this process have been shown to be effective treatments for some cancers. As initiation of angiogenesis involves migration and proliferation of vascular endothelial cells, and agents that elevate cAMP inhibit these processes, PDE2 inhibition may have utility as a treatment for cancer. See Savai, et al, *Targeting cancer with phosphodiesterase inhibitors*, Expert Opin. Investig. Drugs (2010) 19(1):117-131. PDE2 has been shown to be expressed in human vascular endothelial cells (VECs) and inhibition of PDE2 by treatment with selective inhibitors inhibited VEGF promoted migration of VECs. See Netherton and Maurice, *Vascular Endothelial Cell Cyclic Nucleotide Phosphodiesterases and Regulated Cell Migration: Implications in Angiogenesis*, Mol Pharmacol (2005) 67:263-272 and Favot, et al, *VEGF-induced HUVEC migration and proliferation are decreased by PDE2 and PDE4 inhibitors*. Thromb Haemost (2003) 90:334-343. Reduction of PDE2 activity with either small molecule inhibitors or PDE2A siRNA suppressed cell growth and invasion in a human malignant melanoma PMP cell line. See Hiramoto, et al, *Role of phosphodiesterase 2 in growth and invasion of human malignant melanoma cells*, Cellular Signalling (2014), 26:1807-1817. Reduction of PDE2 activity with a small molecule inhibitor attenuated tumor formation in a mouse model of ultraviolet light B-induced tumorigenesis. See Bernard, et al, *PDE2 is a Novel Target for Attenuating Tumor Formation in a Mouse Model of UVB-Induced Skin Carcinogenesis*, PLoS ONE (2014), 9(10):e109862. Thus, in another specific embodiment, compounds of the invention provide methods for treating, preventing, controlling, and/or reducing, attenuating cancers, such as malignant melanomas, skin cancer, and the like.

The subject compounds may be further useful in a method for the prevention, treatment, control, amelioration, or reduction of risk of the diseases, disorders and conditions noted herein. The subject compounds are further useful in a method for the prevention, treatment, control, amelioration, or reduction of risk of the aforementioned diseases, disorders and conditions in combination with other agents. The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention may be desirable. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, AChEis (such as Aricept (donepezil) and Exelon (rivastigmine)) and NMDA blocker Namenda (memantine), beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, atypical antipsychotics, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MAO-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-$HT_{1A}$ agonists or antagonists, especially 5-$HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

The compounds of the present invention may be administered by oral, parenteral (e.g., intramuscular, intraperitoneal, intravenous, ICV, intracistemal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The terms "administration of" and or "administering a" compound should be understood to mean providing a compound of the invention or a prodrug of a compound of the invention to the individual in need of treatment.

The term "composition" as used herein is intended to encompass a product comprising specified ingredients in predetermined amounts or proportions, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by mixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art. By "pharmaceutically acceptable" it is meant the carrier, diluent or excipient must be compatible with the other ingredients of the formulation and not deleterious to the recipient thereof.

The subject compounds are further useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.001 to 10 mg/kg of body weight daily are administered to the patient, e.g., humans and elderly humans. The dosage range will generally be about 0.5 mg to 1.0 g per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Several methods, schemes, and examples for preparing representative compounds of this invention are illustrated below. Starting materials and the requisite intermediates are in some cases commercially available, or can be prepared according to literature procedures or as illustrated herein. The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing conditions as shown in the schemes and examples herein, as well as using other standard manipulations such as ester hydrolysis, cleavage of protecting groups, etc., as may be known in the literature or exemplified in the experimental procedures. Starting materials are made according to procedures known in the art or as illustrated herein.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood.

The representative examples of the compounds of the invention are illustrated in the following non-limiting schemes and Examples.

GENERAL

Starting materials used were obtained from commercial sources or prepared in other examples, unless otherwise noted.

The progress of reactions was often monitored by TLC or LC-MS. The LC-MS was recorded using one of the following methods.

Method A XBridge Shield RP18: 2.5×50 mm, 3.5 um, 1.0 uL injection, 1.00 mL/min flow rate, 90-900 amu scan range, 190-400 nm UV range, 10-95% (over 2.2 min) gradient with MeCN and water (0.04% aq. $NH_3$), hold 1 min; 3.6 minute total run time.

Method B: Supelco Ascentis Express C18, 3×50 mm, 2.7 um column. 2.0 uL injection, 1.25 ml/min flow rate, 170-900 amu scan range, 200-400 nm UV range, 10-99% (over 2.0 min) gradient with MeCN (0.05% TFA) and water (0.05%); 3 minute total run time.

Method C: Supelco Ascentis Express C18, 3×100 mm, 2.7 um column. 2.0 uL injection, 1.00 ml/min flow rate, 170-900 amu scan range, 200-400 nm UV range, 10-99% (over 4.0 min) gradient with MeCN (0.05% TFA) and water (0.05%); 5 minute total run time.

Method D: Waters Acquity UPLC, HSS C18 1.8 um, 2.1×50 mm, MeCN and water with 0.1% trifluoroacetic acid, 1 mL/min flow rate, gradient 5%-100% MeCN over 1.4 min.

Method E: Waters Acquity UPLC, HSS C18 1.8 um, 2.1×50 mm, MeCN and water with 0.1% formic acid, 1 mL/min flow rate, gradient 5%-100% MeCN over 1.4 min.

Method F: Shimadzu: 3.0×50 mm, 2.2 um, 1.0 uL injection, 1.00 mL/min flow rate, 90-900 amu scan range, 190-400 nm UV range, 5-100% (over 2.2 min) gradient with MeCN (0.05% TFA) and water (0.05% TFA), hold 1 min; 3.6 minute total run time.

Method G: Titan C18: 2.1×50 mm, 1.9 um, 1.0 uL injection, 0.80 mL/min flow rate, 90-900 amu scan range, 190-400 nm UV range, 5-100% (over 2.1 min) gradient with MeCN (0.05% TFA) and water (0.05% TFA), hold 0.5 min; 3.0 minute total run time.

Method H: ZORBAX Eclipse Plus C18: 3.0×50 mm, 1.8 um, 1.0 uL injection, 1.00 mL/min flow rate, 90-900 amu scan range, 190-400 nm UV range, 5-100% (over 2.1 min) gradient with MeCN (0.1% FA) and water (0.1% FA), hold 0.5 min; 3.0 minute total run time.

Method I: XBridge C18: 4.6×50 mm, 3.5 um, 1.0 uL injection, 1.50 mL/min flow rate, 90-900 amu scan range, 190-400 nm UV range, 10-95% (over 2.2 min) gradient with MeCN and water (5 μM $NH_4HCO_3$), hold 1 min; 3.6 minute total run time. NMR was recorded at room temperature unless noted otherwise on Varian Inova 400 or 500 MHz spectrometers with the solvent peak used as the reference or on Bruker 300 or 400 MHz spectrometers with the TMS peak used as internal reference.

The methods used for the preparation of the compounds of this invention are illustrated by the following schemes. Unless specified otherwise, all starting materials used are commercially available.

Scheme 1

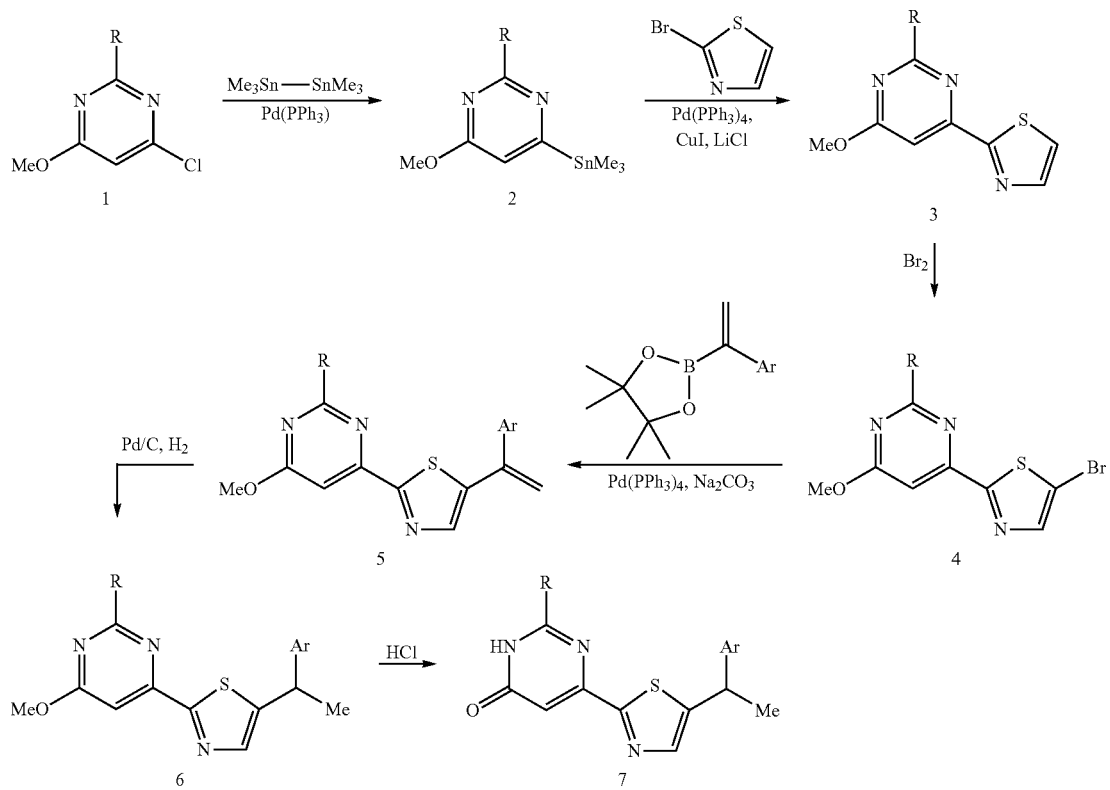

Scheme 1 illustrates a synthetic procedure for the synthesis of thiazolylpyrimidinones such as 7 from pyrimidine precursors such as 1. Palladium catalyzed stannylation of 1 furnishes intermediate 2, which is converted to thiazolylpyrimidine 3 via a Suzuki coupling reaction. Bromination of 3 provides compound 4, which can be converted to a 2-pyrimidinyl-5-vinyl-thiazole such as 5 via a Suzuki coupling reaction. Reduction of 5 followed by deprotection under acidic conditions provides thiazolylpyrimidinones such as 7.

Scheme 2.

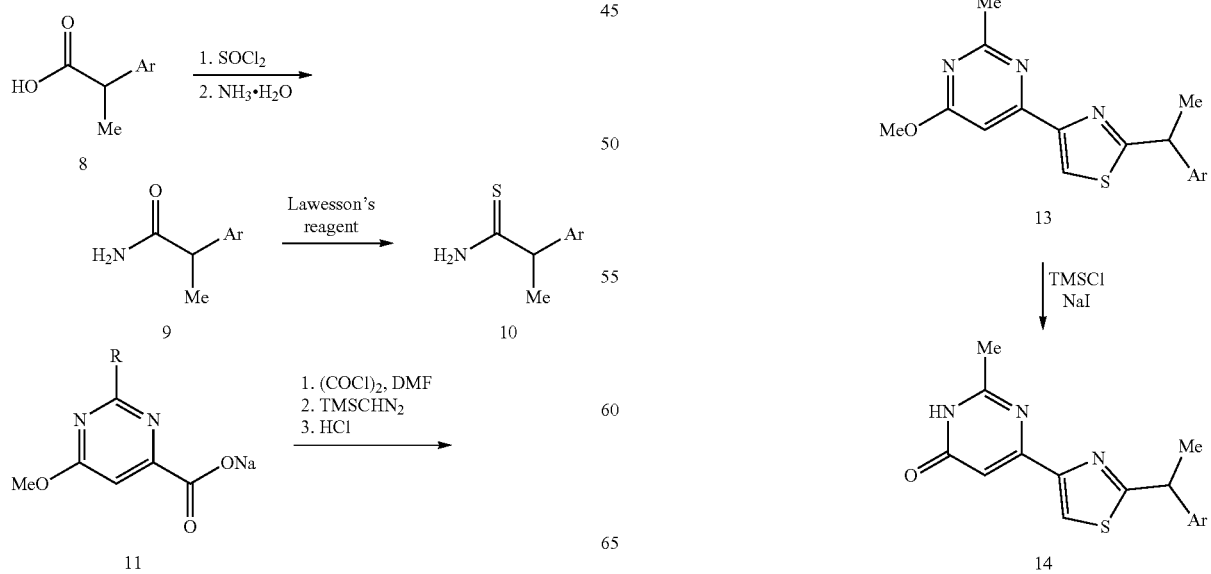

-continued

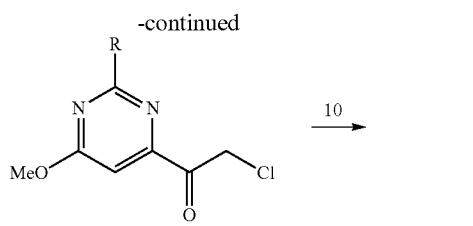

Scheme 2 illustrates a synthetic sequence for the preparation of thiazolylpyrimidinones such as 14 from thioamides such as 10 and α-chloroketones such as 12. Thioamides such as 10 may be prepared with Lawesson's reagent from amides such as 9, which in turn may be prepared from carboxylic acids such as 8. Chloroketone 12 may be prepared in 3 steps from carboxylate 11. Thioamide such as 10 and chloroketones such as 12 may be condensed to furnish thiazolylpyrimidines such as 13, which may be deprotect with sodium iodide and trimethylsilyl chloride to provide derivatives such as 14.

Scheme 3.

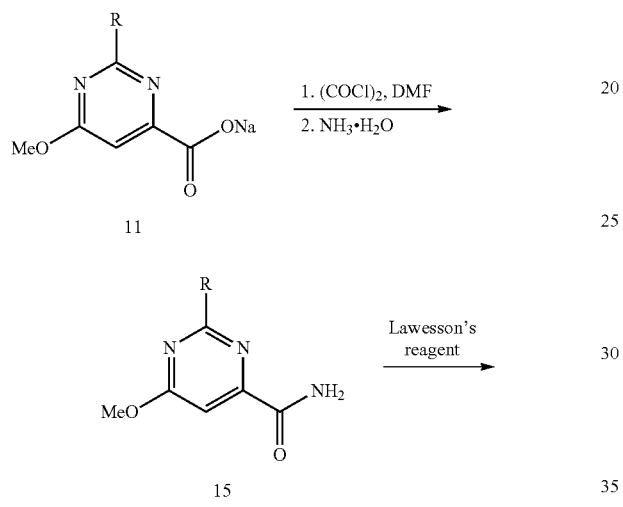

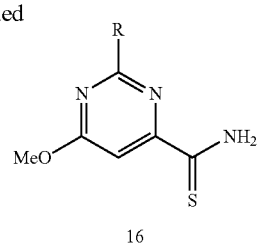

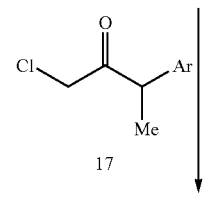

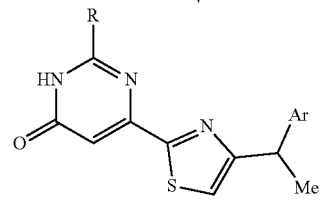

Scheme 3 illustrates a synthetic sequence for the preparation of thiazolyl pyrimidinones such as 18 from carboxylates such as 11. Compound 11 may be converted to amide 15 via activation with oxalyl chloride followed by quenching with ammonia. Amide 15 is converted to thioamide 16 by treatment with Lawesson's reagent. Thermal condensation of 16 with a chloroketone such as 17 provides thiazolyl pyrimidinone derivatives such as 18.

Scheme 4

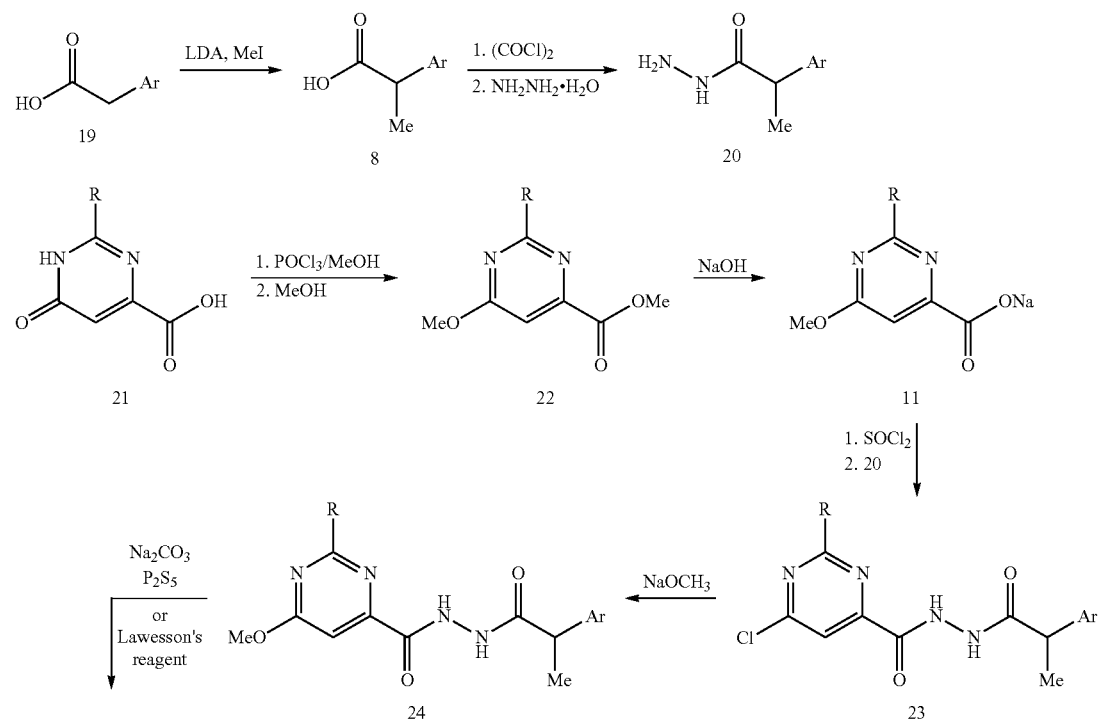

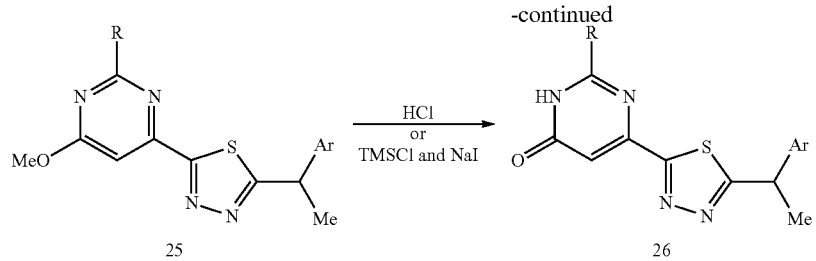

Scheme 4 illustrates a synthetic sequence for the preparation of thiadiazolyl pyrimidinones such as 26 from carboxylates such as 11 and hydrazides such as 20. Hydrazide 20 may be prepared by alkylation of a carboxylic acid such as 19 followed by activation with oxalyl chloride and quenching with hydrazine. Carboxylate 11 may be prepared from pyrimidinone carboxylic acids such as 21 via a three step sequence comprised of activation with phosphorous oxychloride, quenching with methanol, and saponification with sodium hydroxide. Intermediate 23 is prepared by coupling of the acid chloride derived from 11 and hydrazide 20. Intermediate 23 is then converted to the alkoxypyrimidine 24 with sodium methoxide. Treatment of 24 with phosphorous pentasulfide yields thiadiazolyl pyrimidine 25, which may be converted to thiadiazolyl pyrimidinone 26 under acidic conditions or via treatment with trimethylsilylchloride and sodium iodide.

Scheme 5 illustrates a synthetic sequence for the preparation of oxazolylpyrimidinones such as 32 from aminoketones such as 28 and acid chlorides such as 29. Aminoketone 28 can be prepared from azidoketone 27 via reduction. Azidoketone 27 is prepared by treatment of 17 with sodium azide. Chloroketone 17 can be prepared from carboxylic acids such as 8 via a three step process consisting of acid chloride formation, treatment with trimethylsilyldiazomethane, and quenching with hydrochloric acid. Intermediate 30 is prepared from coupling of 28 and 29. Compound 31 is prepared by cyclization of intermediate 30 with phosphorous oxychloride. An S<sub>N</sub>Ar reaction of 31 with sodium hydroxide provides oxazolylpyrimidinone 32.

Scheme 5

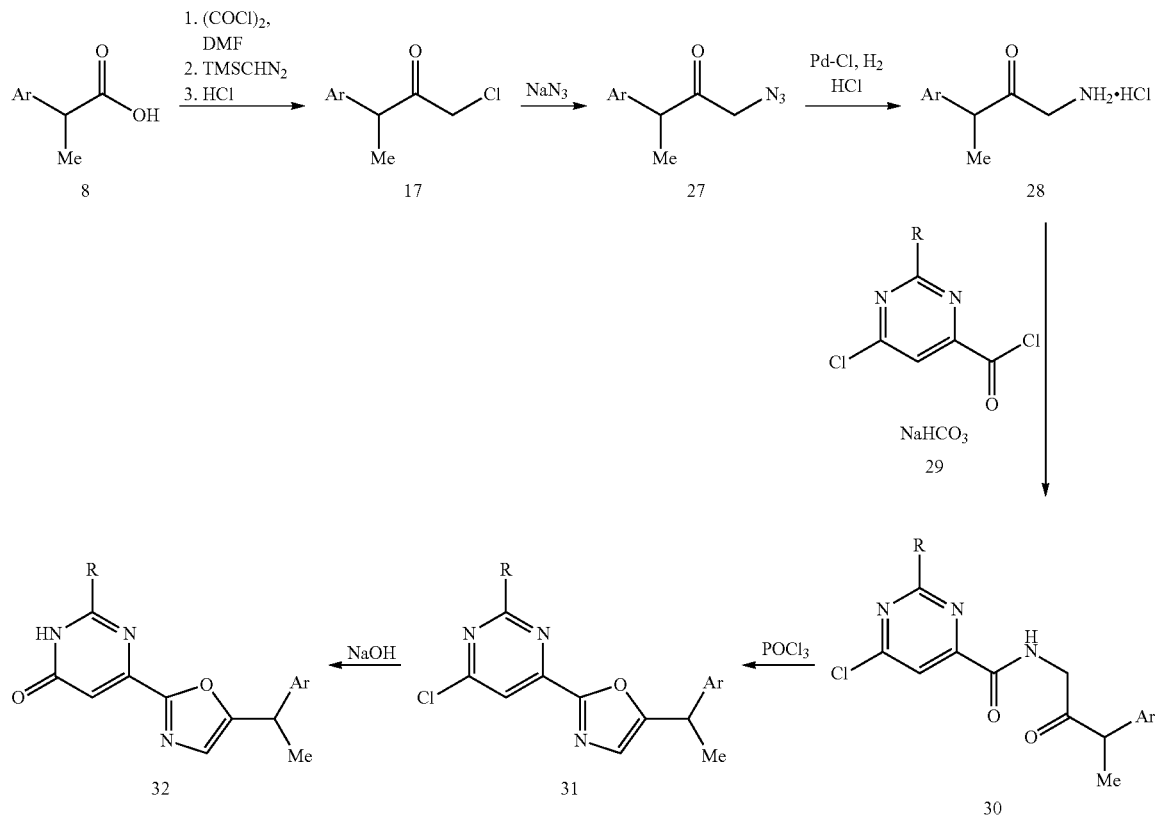

Scheme 6.

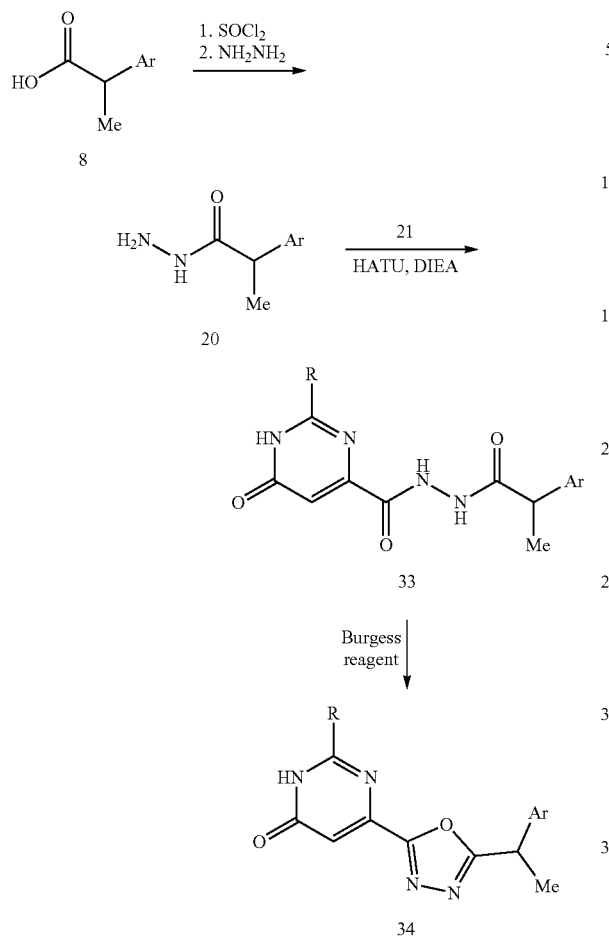

Scheme 6 illustrates a synthetic sequence for the preparation of oxadiazolyl pyrimdinones such as 34 from carboxylic acids such as 8. Compound 8 is transformed to hydrazide 20 via activation with thionyl chloride followed by quenching with hydrazine. Coupling of 20 with acid 21 provides intermediate 33 which can be converted to oxadiazolylpyrimidinone 34 using the Burgess reagent.

Scheme 7.

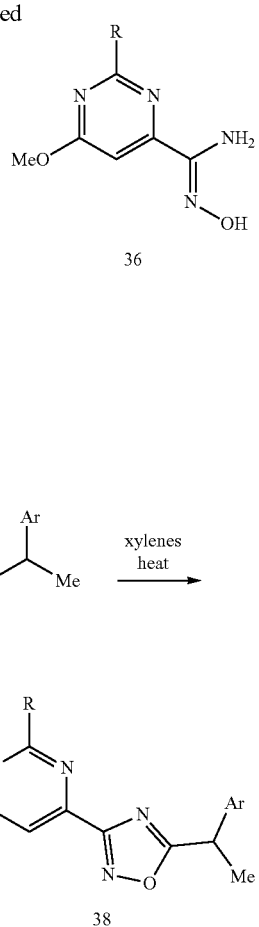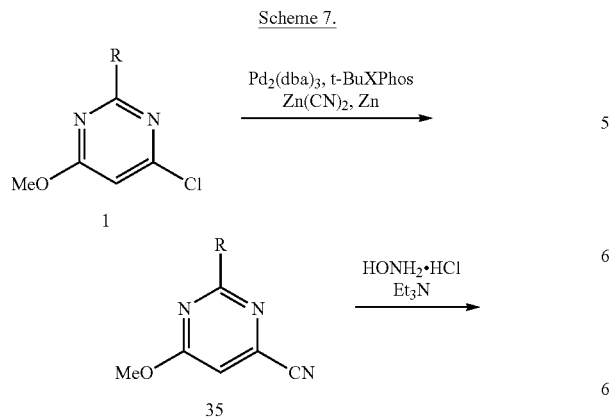

Scheme 7 illustrates a synthetic sequence for the preparation of oxadiazolyl pyrimidinones such as 38 from hydroxyamidines such as 36 and carboxylic acid derivatives such as 8. Compounds such as 36 may be prepared from pyrimidines such as 1 in a two step sequence consisting of a palladium catalyzed cyanation reaction followed by treatment with hydroxylamine under basic conditions. Compound 36 may be coupled to the acid chloride of 8 to provide the penultimate intermediate 37, which can be converted to oxadiazolylpyrimdinone 38 under thermal conditions.

Scheme 8.

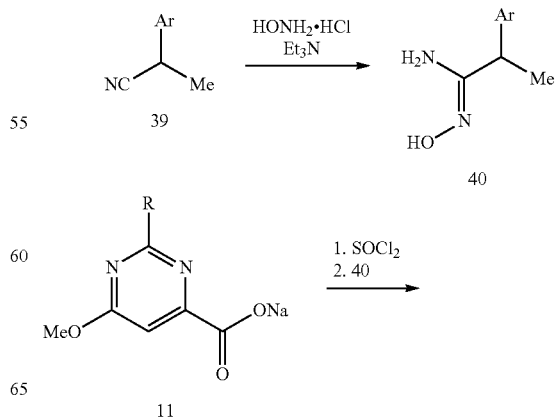

-continued

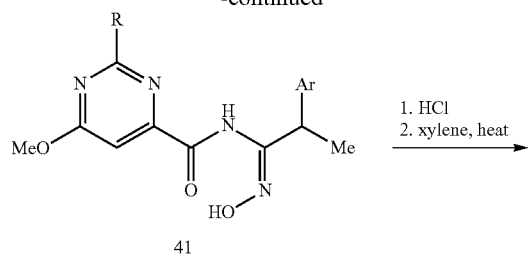

41

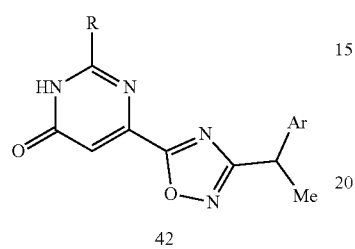

42

Scheme 8 illustrates a synthetic sequence for the preparation of oxadiazolyl pyrimidinones such as 42 from carboxylates such as 11 and hydroxyamidines such as 40. Intermediate 41 may be prepared by coupling of 40 with the acid chloride derived from 11. Acid mediated deprotection of 41 followed by cyclization under thermal conditions furnishes oxadiazolylpyrimidinone 42.

Scheme 9

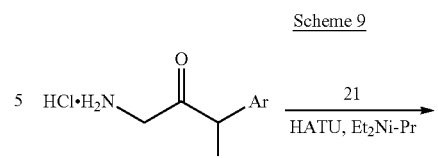

28

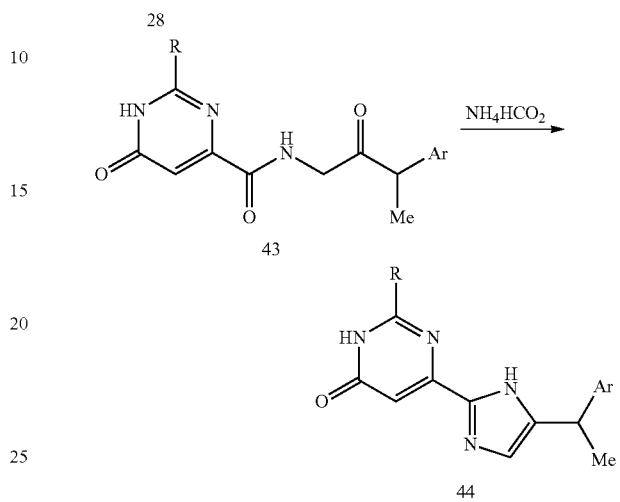

Scheme 9 illustrates a synthetic procedure for the synthesis of imidazolylpyrimidinones such as 44 from aminoketones such as 28. Coupling of 28 with pyrimidinone acid 21 yields intermediate 43 which may be converted to imidazolylpyrimidinone 44.

Scheme 10.

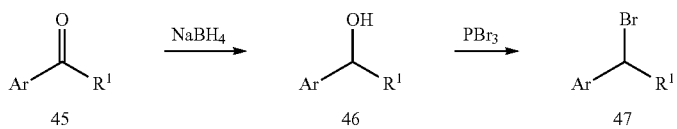

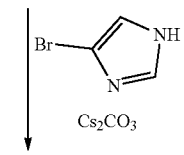

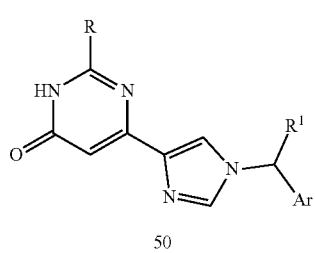

50

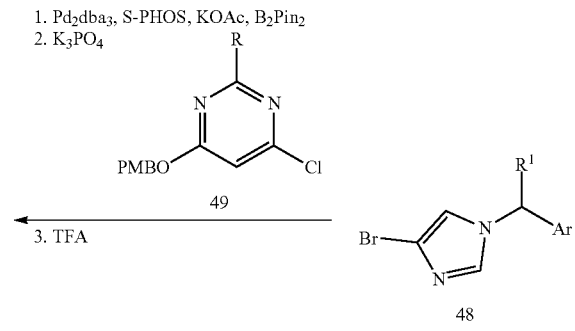

Scheme 10 illustrates a synthetic sequence for the preparation of imidazolylpyrimidinones such as 50 from bromoimidazole 48 and pyrimidine 49 via a palladium catalyzed borylation-Suzuki coupling sequence. Compound 48 is prepared in three steps from aryl ketones such as 45 by reduction of 45 to 46 with sodium borohydride, bromination of 46 to 47 with phosphorous (III) bromide, and finally alkylation of 4-bromoimidazole with 47.

Scheme 11

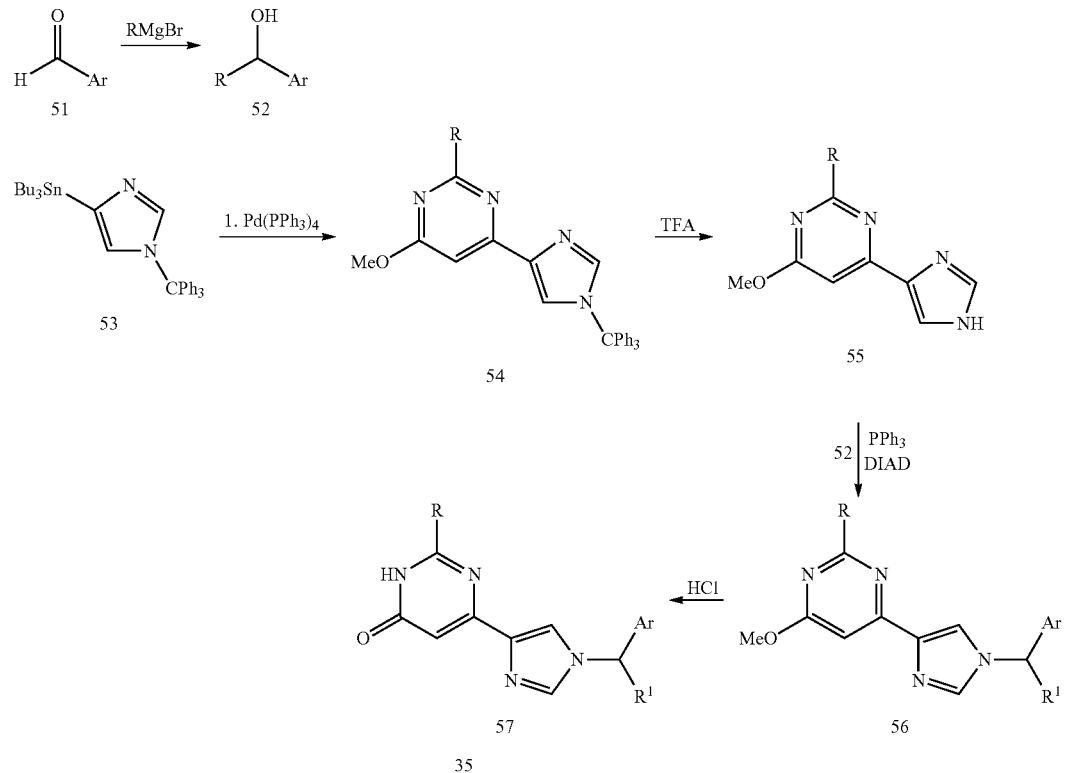

Scheme 11 illustrates a synthetic sequence for the preparation of imidazolylpyrimidinones such as 57 from Mitsunobu reaction of intermediate 55 and benzylic alcohols such as 52. Compound 52 is obtained via nucleophilic addition to aldehydes such as 51. Intermediate 55 is prepared via a Stille coupling reaction of 53 with chloropyrimidine 1, followed by deprotection with TFA. Mitsunobu reaction of 55 with 52 provides intermediate 56 which can be deprotected under acidic conditions to afford imidazolylpyrimidinone derivatives 57.

Scheme 12.

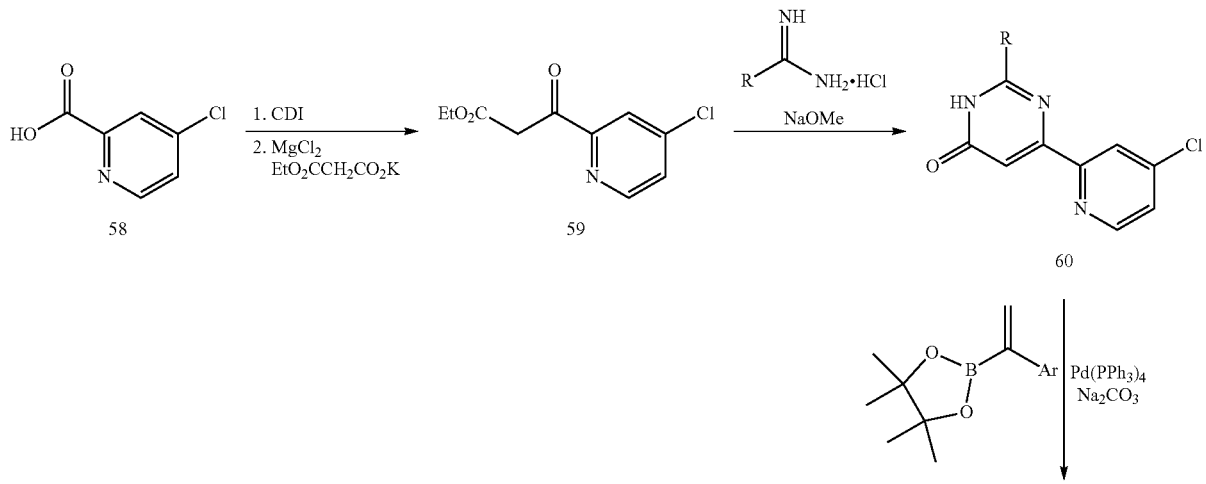

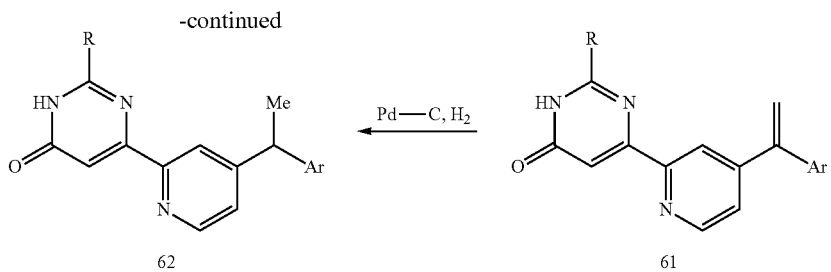

Scheme 12 illustrates a synthetic sequence for the preparation of pyridylpyrimidinone derivatives such as 62 from halopyridine carboxylic acids such as 58. Compound 58 can be converted to β-ketoester 59 by activation with carbonyldiimidazole followed by reaction with ethyl potassium malonate and magnesium chloride. β-ketoester 59 can be condensed with an amidine under basic conditions to provide pyridylpyrimidinone intermediate 60. Compound 60 can be converted to 62 via a Suzuki coupling reaction with a vinylboronate followed by hydrogenation.

tion with an arylbromide, to 63 affords intermediate 64. Compound 64 can be coupled to chloropyrimidine 49 via a palladium catalyzed borylation-Suzuki coupling sequence to provide intermediate 65. Secondary alcohol 65 is converted to the mesylate to enable copper substitution with a Grignard reagent. Subsequent deprotection with trifluoroacetic acid of the resulting intermediate furnishes pyridylpyrimidinone 66.

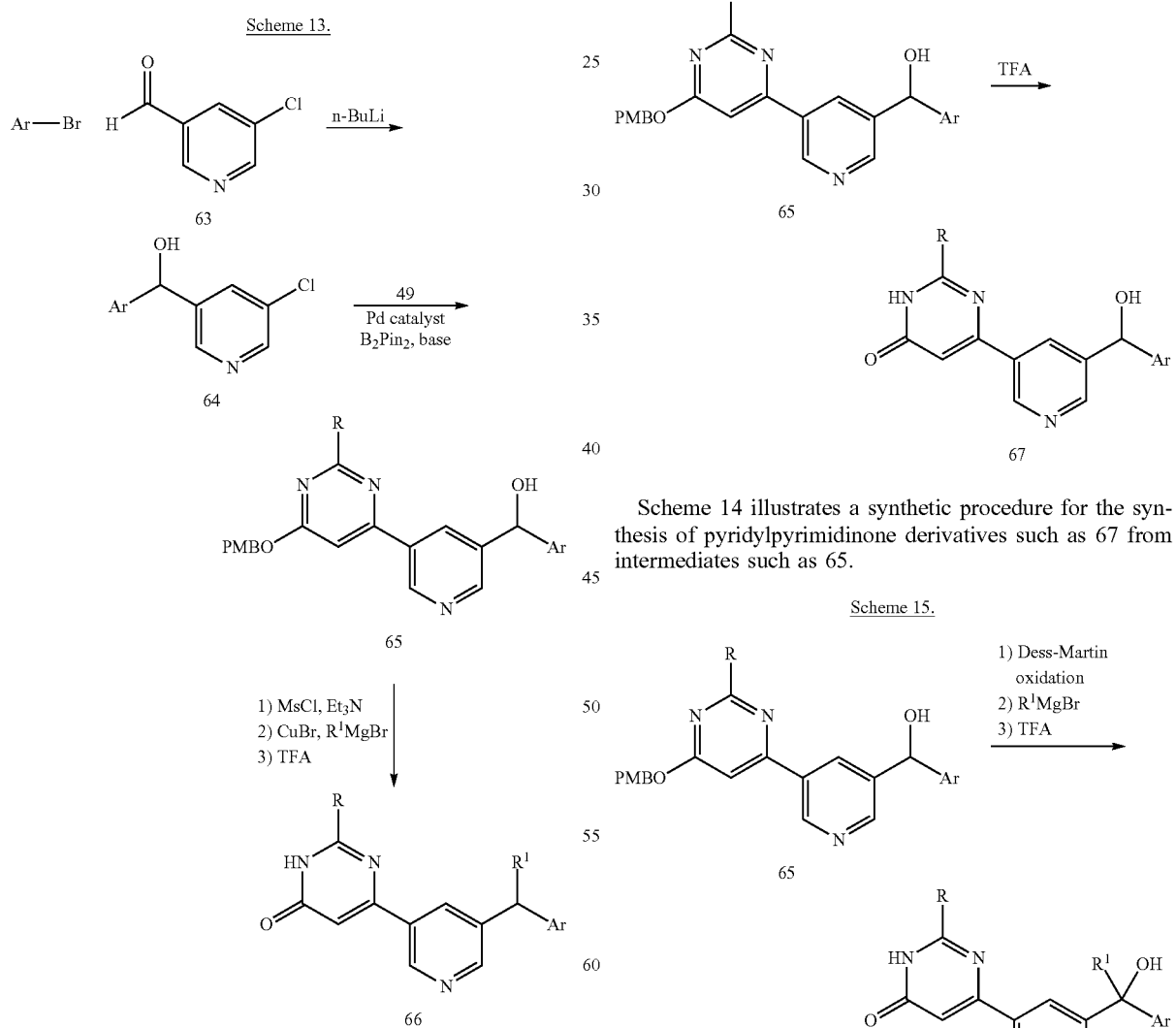

Scheme 13 illustrates a synthetic sequence for the preparation of pyridylpyrimidinones such as 66 from chloropyridylaldehydes such as 63. Addition of an aryllithium reagent, generated from a lithium-halogen exchange reac- Scheme 14 illustrates a synthetic procedure for the synthesis of pyridylpyrimidinone derivatives such as 67 from intermediates such as 65.

Scheme 15 illustrates a synthetic sequence for the preparation of pyridylpyrimidinones such as 68 containing a tertiary alcohol from intermediates such as 65 via a three-step sequence consisting of oxidation to the ketone, treatment with a Grignard reagent, and finally deprotection under acidic conditions.

Scheme 16.

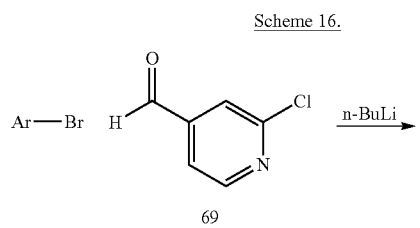

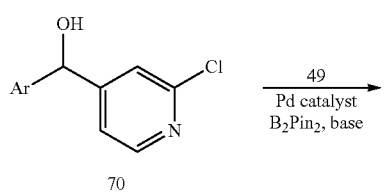

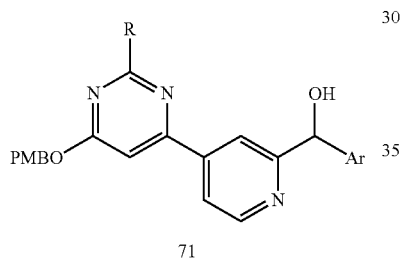

1) MsCl, Et₃N
2) CuBr, R¹MgBr
3) TFA

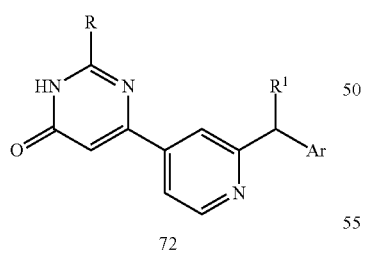

Scheme 16 illustrates a synthetic sequence for the preparation of pyridylpyrimidinones such as 72 from chloropyridylaldehydes such as 69. Addition of an aryllithium reagent, generated from a lithium-halogen exchange reaction with an arylbromide, to 69 affords intermediate 70. Compound 70 can be coupled to chloropyrimidine 49 via a palladium catalyzed borylation-Suzuki coupling sequence to provide intermediate 71. Secondary alcohol 71 is converted to the mesylate to enable copper mediated substitution with a Grignard reagent. Subsequent deprotection with trifluoroacetic acid of the resulting intermediate furnishes pyridylpyrimidinone 72.

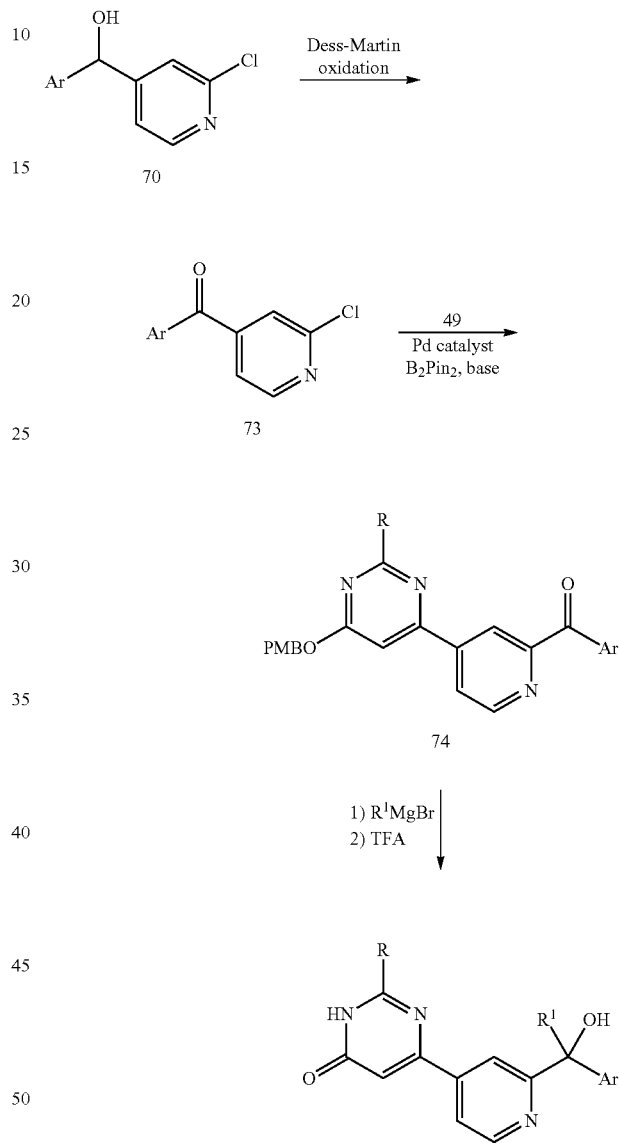

Scheme 17 illustrates a synthetic sequence for the preparation of pyridylpyrimidinone derivatives containing a tertiary alcohol such as 75 from intermediates such as 70. Compound 70 may be converted to benzophenone derivative 73 via Dess-Martin oxidation. A palladium catalyzed borylation/Suzuki cross coupling sequence of 73 with pyrimidine 49 provides intermediate 74, which can be converted to pyridylpyrimidinone derivatives such as 75 by treatment with a Grignard reagent followed by deprotection under acidic conditions.

Scheme 18.

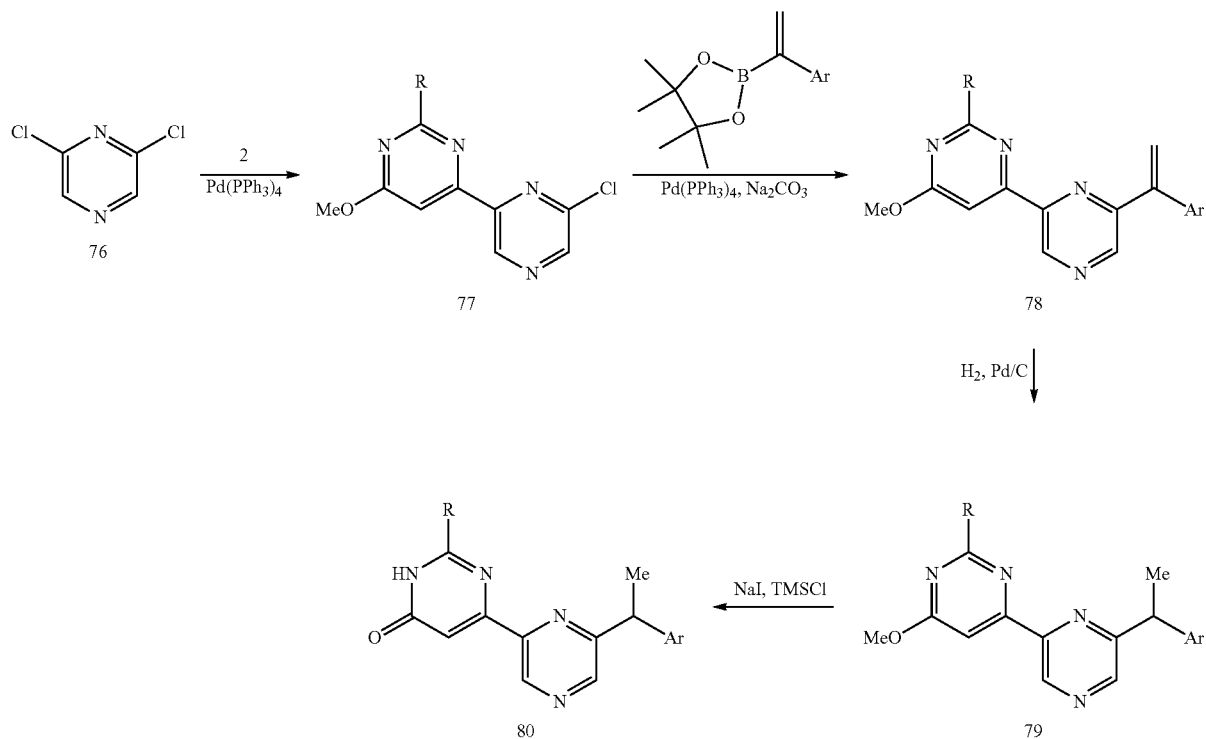

Scheme 18 illustrates a synthetic sequence for the preparation of pyrazinylpyrimidinone derivatives such as 80 from dichloropyrazine 76. A Stille cross coupling reaction of 76 with stannane 2 provides intermediate 77. A Suzuki cross coupling reaction of 77 with a vinyl boronate provides intermediate 78, which is reduced to 79 with palladium on carbon under an atmosphere of hydrogen. Compound 79 is deprotected with sodium iodide and trimethylsilyl chloride to furnish pyrazinylpyrimidinone derivatives such as 80.

Scheme 19

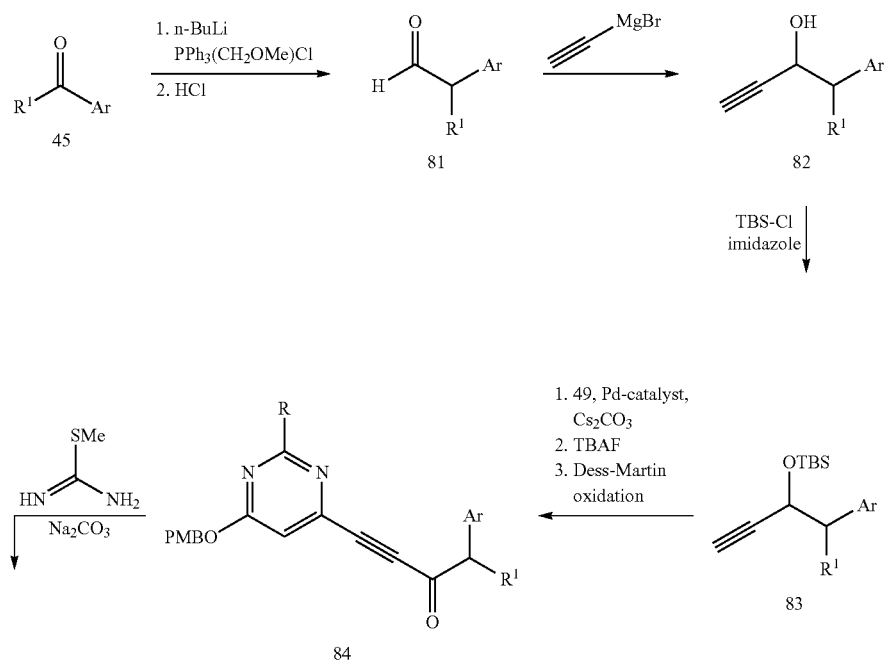

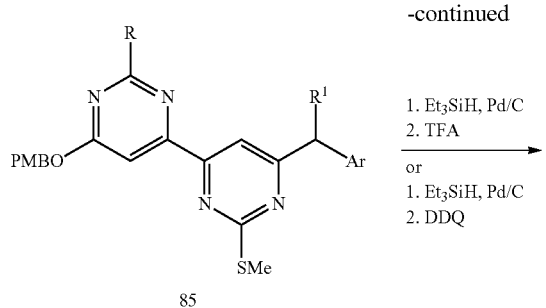
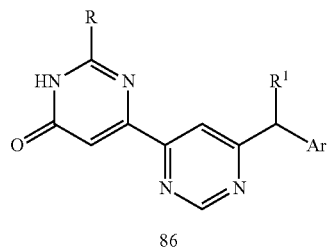

Scheme 19 illustrates a synthetic sequence for the preparation of pyrimidinylpyrimidinones such as 86 from aryl ketone derivatives such as 45. Wittig reaction of 45 with methoxymethyltriphenylphosphonium chloride followed by treatment with HCl provides aldehyde 81. Addition of ethynylmagnesium bromide to 81 provides propargylic alcohol 82 which is protected as the TBS-ether 83. A three step sequence consisting of a Sonogashira cross coupling reaction of 83 and 49, deprotection with TBAF, and Dess-Martin oxidation provides intermediate 84. Intermediate 84 is condensed with thiomethylamidine under basic conditions to furnish thiomethylpyrimidine intermediate 85, which can be sequentially reduced with triethyl silane and palladium on carbon and then deprotected under acidic or oxidation conditions to provide pyrimidinylpyrimidinone derivatives such as 86.

Example 1

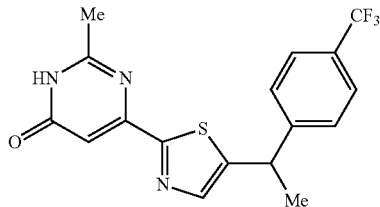 [SMILES: Cc1nc(-c2ncc(C(C)c3ccc(C(F)(F)F)cc3)s2)cc(=O)[nH]1]

2-Methyl-6-(5-(1-(4-(trifluoromethyl)phenyl)ethyl)thiazol-2-yl)pyrimidin-4(3H)-one, (Scheme 1)

Step 1.
4-Methoxy-2-methyl-6-(trimethylstannyl)pyrimidine 1,1,1,2,2,2-Hexamethyl-distannane (620 mg, 1.892 mmol) and tetrakis(triphenylphosphine)palladium (219 mg, 0.189 mmol) were added to a solution of 4-chloro-6-methoxy-2-methylpyrimidine (300 mg, 1.892 mmol) in 1,4-dioxane (3 mL). The reaction mixture was degassed with nitrogen 3 times and stirred for 1 h at 100° C. under and atmosphere of nitrogen. The reaction mixture was used in the next step directly without further purification. MS=285.0/287.0/289.0 (+ESI).

Step 2.
2-(6-Methoxy-2-methylpyrimidin-4-yl)thiazole

Cuprous iodide (108 mg, 0.567 mmol), lithium chloride (241 mg, 5.67 mmol), 2-bromothiazole (341 mg, 2.081 mmol) and 1,4-dioxane (2 mL) were added into the mixture from step 1. Then the reaction mixture was degassed with nitrogen 3 times and stirred for 1 h in a sealed tube at 120° C. The mixture was cooled, filtered and the filtrate was concentrated. Then brine (10 mL) was added. The resulting mixture was extracted with ethyl acetate (3×10 mL). The combined organic extracts were dried with anhydrous sodium sulfate and filtered. The filtrate was concentrated. The residue was purified by silica gel chromatography (16% ethyl acetate in petroleum ether) to furnish the title compound as a solid. MS=208.0 (+ESI).

Step 3. 5-Bromo-2-(6-methoxy-2-methylpyrimidin-4-yl)thiazole

Bromine (1.00 mL, 19.40 mmol) was added to 2-(6-methoxy-2-methylpyrimidin-4-yl)thiazole (150 mg, 0.724 mmol). The reaction mixture was stirred for 1 h at RT. The reaction solution was quenched with saturated aqueous sodium hydrogen sulfite (20 mL) and extracted with ethyl acetate (3×15 mL). The combined organic extracts were dried with anhydrous sodium sulfate and filtered. The filtrate was concentrated under vacuum. The residue was purified by silica gel chromatography (5% ethyl acetate in petroleum ether) to furnish the title compound as a solid. MS=285.8/287.9 (+ESI).

Step 4. 2-(6-Methoxy-2-methylpyrimidin-4-yl)-5-(1-(4-(trifluoromethyl)phenyl)vinyl)thiazole The title compound was prepared using procedures similar to those described in Step 3 of Example 22 using 5-bromo-2-(6-methoxy-2-methylpyrimidin-4-yl)thiazole to afford the title compound as a liquid. MS=378.2 (+ESI).

Step 5. 2-(6-Methoxy-2-methylpyrimidin-4-yl)-5-(1-(4-(trifluoromethyl)phenyl)ethyl)thiazole The title compound was prepared using procedures similar to those described in step 4 of Example 22 using 2-(6-methoxy-2-methylpyrimidin-4-yl)-5-(1-(4-(trifluoromethyl)phenyl)vinyl)thiazole in ethyl acetate to afford the title compound as a solid. MS=380.1 (+ESI).

Step 6. 2-Methyl-6-(5-(1-(4-(trifluoromethyl)phenyl)ethyl)thiazol-2-yl)pyrimidin-4(3H)-one The title compound was prepared using procedures similar to those described in step 8 of Examples 4 and 5 using 2-(6-methoxy-2-methylpyrimidin-4-yl)-5-(1-(4-(trifluoromethyl)phenyl) ethyl)thiazole to afford the title compound as a solid. $^1$H NMR (300 MHz, CDCl$_3$) δ: 7.71 (s, 1H), 7.59 (d, J=8.1 Hz, 2H), 7.39 (d, J=8.1 Hz, 2H), 7.12 (s, 1H), 4.48 (q, J=7.2 Hz, 1H), 2.52 (s, 3H), 1.78 (d, J=7.2 Hz, 3H). MS=366.1 (+ESI).

Example 2

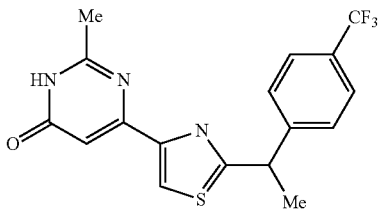

2-Methyl-6-(2-(1-(4-(trifluoromethyl)phenyl)ethyl)
thiazol-4-yl)pyrimidin-4(3H)-one, (Scheme 2)

Step 1. 2-(4-(Trifluoromethyl)phenyl)propanamide

The title compound was prepared using procedures similar to those described in step 2 of Examples 4 and 5 using thionyl chloride, 2-(4-(trifluoromethyl)phenyl)propanoic acid and ammonium hydroxide to afford the title compound as a solid and was used in the next step directly without further purification. MS=217.7 (+ESI).

Step 2.
2-(4-(Trifluoromethyl)phenyl)propanethioamide 2,4-Bis(4-methoxyphenyl)-1,3,2,4-dithiadiphosphetane-2,4-disulfide (1.12 g, 2.76 mmol) was added to a mixture of 2-(4-(trifluoromethyl)phenyl)propanamide (0.300 g, 1.38 mmol) in 1,2-dichloroethane (5 mL). The resulting reaction mixture was stirred at 75° C. for 1.5 h. After cooling to RT, the resulting mixture was concentrated under vacuum. The residue was diluted with water (30 mL) and extracted with ethyl acetate (3×30 mL). The combined organic extracts were washed with water (2×20 mL) and brine (2×20 mL), dried with anhydrous sodium sulfate and filtered. The filtrate was concentrated under vacuum. The residue was purified by silica gel chromatography (35% ethyl acetate in petroleum ether) to furnish the title compound as a liquid. MS=234.2 (+ESI).

Step 3. 2-Chloro-1-(6-methoxy-2-methylpyrimidin-4-yl)ethanone

Oxalyl chloride (1.89 g, 14.9 mmol) was added to a mixture of sodium 6-methoxy-2-methylpyrimidine-4-carboxylate (1.00 g, 5.95 mmol) in dichloromethane (100 mL) at 0° C. followed by the addition of DMF (0.1 mL, 5.95 mmol). The reaction mixture was stirred for 2 h at 25° C. The resulting mixture was concentrated under vacuum and was then dissolved in tetrahydrofuran (10 mL) and acetonitrile (10 mL). The reaction solution was degassed with nitrogen 3 times. Then (diazomethyl)-trimethylsilane (8.05 mL, 16.1 mmol; 2 M in hexane) was added dropwise with stirring at 0° C. The reaction mixture was stirred for 16 h at 25° C. To this was added a solution of saturated hydrogen chloride gas in ethyl acetate (40 mL). The resulting mixture was stirred for 2 h at 25° C. and concentrated under vacuum. The resulting mixture was diluted with water (40 mL) and extracted with ethyl acetate (3×50 mL). The combined organic extracts were washed with water (2×30 mL) and brine (2×30 mL), dried with anhydrous sodium sulfate and filtered. The filtrate was concentrated under vacuum. The residue was purified by silica gel chromatography (5% ethyl acetate in petroleum ether) to furnish the title compound as a solid. $^1$H NMR (400 MHz, DMSO-$d_6$) δ: 7.14 (s, 1H), 5.22 (s, 2H), 3.97 (s, 3H), 2.53 (s, 3H).

Step 4. 4-(6-Methoxy-2-methylpyrimidin-4-yl)-2-(1-(4-(trifluoromethyl)phenyl)ethyl)-thiazole 2-(4-(Trifluoromethyl)phenyl)propanethioamide (55.8 mg, 0.239 mmol) was added to a mixture of 2-chloro-1-(6-methoxy-2-methylpyrimidin-4-yl)ethanone (40.0 mg, 0.199 mmol) in 1,4-dioxane (2 mL). The reaction mixture was irradiated with microwave radiation at 125° C. for 4 h. After cooling to RT, the resulting mixture was concentrated under vacuum. The residue was diluted with water (10 mL) and extracted with ethyl acetate (3×15 mL). The combined organic extracts were washed with water (2×10 mL) and brine (2×10 mL), dried with anhydrous sodium sulfate and filtered. The filtrate was concentrated under vacuum. The residue was purified by silica gel chromatography (2-10% ethyl acetate in petroleum ether) to furnish the title compound as a liquid. MS=380.2 (+ESI).

Step 5. 2-Methyl-6-(2-(1-(4-(trifluoromethyl)phenyl)ethyl)thiazol-4-yl)pyrimidin-4(3H)-one Sodium iodide (79.0 mg, 0.527 mmol) was added to a mixture of 4-(6-methoxy-2-methylpyrimidin-4-yl)-2-(1-(4-(trifluoromethyl)phenyl)ethyl)thiazole (50.0 mg, 0.132 mmol) in acetonitrile (2 mL) followed by the addition of chlorotrimethylsilane (57.3 mg, 0.527 mmol). The reaction mixture was degassed with nitrogen 3 times. The reaction mixture was irradiated with microwave radiation at 120° C. for 20 min. After cooling to RT, the reaction mixture was quenched with saturated sodium bisulfate (10 mL) and extracted with ethyl acetate (3×15 mL). The combined organic extracts were washed with water (3×10 mL) and brine (3×10 mL), dried with anhydrous sodium sulfate and filtered. The filtrate was concentrated under reduced pressure. The crude product was purified by preparative reverse phase HPLC (Xbridge RP18 column; 5-85% acetonitrile in water+0.05% ammonium bicarbonate) to furnish the title compound as a solid. $^1$H NMR (300 MHz, DMSO-$d_6$) δ: 12.40-12.20 (br, 1H), 8.17 (s, 1H), 7.72 (d, J=8.4 Hz, 2H), 7.65 (d, J=8.4 Hz, 2H), 6.74 (s, 1H), 4.75 (q, J=7.2 Hz, 1H), 2.51 (s, 3H), 1.75 (d, J=7.2 Hz, 3H). MS=366.1 (+ESI).

Example 3

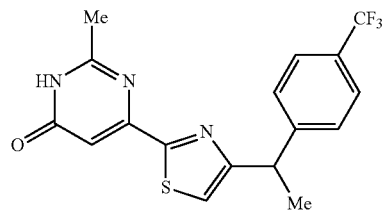 [SMILES: Cc1nc(-c2nc(C(C)c3ccc(C(F)(F)F)cc3)cs2)cc(=O)[nH]1]

2-Methyl-6-(4-(1-(4-(trifluoromethyl)phenyl)ethyl)
thiazol-2-yl)pyrimidin-4(3H)-one, (Scheme 3)

Step 1.
6-Methoxy-2-methylpyrimidine-4-carboxamide

The title compound was prepared using procedures similar to those described in step 2 of Examples 4 and 5 using sodium 6-methoxy-2-methylpyrimidine-4-carboxylate and ammonium hydroxide to afford the title compound as a solid. MS=168.4 (+ESI).

Step 2. 6-Methoxy-2-methylpyrimidine-4-carbothioamide

The title compound was prepared using procedures similar to those described in step 2 of Example 2 using 6-methoxy-2-methylpyrimidine-4-carboxamide to afford the title compound as a solid. MS=184.4 (+ESI).

Step 3. 2-Methyl-6-(4-(1-(4-(trifluoromethyl)phenyl)ethyl)thiazol-2-yl)pyrimidin-4(3H)-one 1-Chloro-3-(4-(trifluoromethyl)phenyl)butan-2-one (from step 1 of Example 8) (0.109 g, 0.437 mmol) was added to a stirred mixture of 6-methoxy-2-methylpyrimidine-4-carbothioamide (80 mg, 0.437 mmol) in 1,4-dioxane (10 mL) and the mixture was stirred at 120° C. for 12 h. The mixture was cooled, diluted with ethyl acetate (100 mL), washed with brine (2×50 mL). The organic layer was dried with anhydrous sodium sulfate, filtered and the filtrate was concentrated. The residue was purified by preparative reverse phase HPLC (XBridge C18; 50-75% acetonitrile in water+0.05% NH$_4$HCO3) to furnish the title compound as a solid. $^1$H NMR (400 MHz, DMSO-d$_6$) δ: 12.70-12.51 (br, 1H), 7.67 (d, J=8.1 Hz, 2H), 7.66 (s, 1H), 7.56 (d, J=8.1 Hz, 2H), 6.72 (s, 1H), 4.51-4.48 (m, 1H), 2.35 (s, 3H), 1.66 (d, J=7.2 Hz, 3H). MS=366.1 (+ESI).

Examples 4 and 5

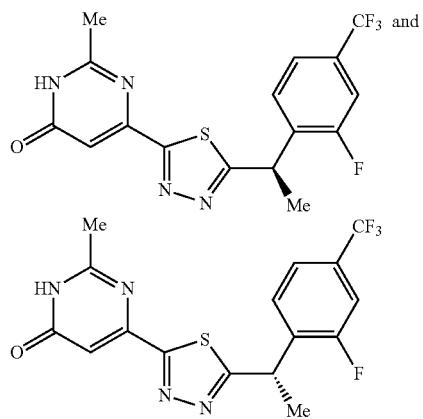

(R)- and (S)-6-(5-(1-(2-fluoro-4-(trifluoromethyl)phenyl)ethyl)-1,3,4-thiadiazol-2-yl)-2-methylpyrimidin-4(3H)-one, (Scheme 4)

Step 1. 2-(2-Fluoro-4-(trifluoromethyl)phenyl)propanoic acid n-Butyllithium (3.96 mL, 9.90 mmol) was added to a stirred solution of diisopropylamine (1.00 g, 9.90 mmol) in tetrahydrofuran (30 mL) at 0° C. The solution was stirred at 0° C. for 20 minutes. A solution of 2-(2-fluoro-4-(trifluoromethyl)phenyl)acetic acid (1.00 g, 4.50 mmol) in tetrahydrofuran (10 mL) was added into the above solution with stirring at −60° C. over 10 minutes. The resulting mixture was stirred at −70° C. for 2 h and at −40° C. for 1 h followed by the addition of a solution of iodomethane (0.703 g, 4.95 mmol) in tetrahydrofuran (10 mL) at −70° C. over 5 min. The reaction mixture was stirred for 16 h at RT. The resulting mixture was quenched with saturated ammonium chloride (80 mL) and extracted with dichloromethane (3×80 mL). The combined organic extracts were dried with anhydrous sodium sulfate and filtered. The residue was purified by silica gel chromatography (80% ethyl acetate in petroleum ether) to furnish the title compound as a liquid. $^1$H NMR (300 MHz, CDCl$_3$) δ: 12.11-12.09 (br, 1H), 7.61-7.38 (m, 2H), 7.38-7.28 (m, 1H), 4.10 (q, J=7.2 Hz, 1H), 1.56 (d, J=7.2 Hz, 3H).

Step 2. 2-(2-Fluoro-4-(trifluoromethyl)phenyl)propanehydrazide

Oxalyl chloride (2.06 g, 16.2 mmol) was added to a solution of 2-(2-fluoro-4-(trifluoromethyl)phenyl)propanoic acid (1.53 g, 6.48 mmol) in dichloromethane (25 mL) with stirring at 0° C. followed by the addition of DMF (5 μl, 0.065 mmol). The reaction mixture was stirred for 16 h at RT. The resulting mixture was concentrated under vacuum and then dissolved in tetrahydrofuran (20 mL). The solution was then added dropwise to a solution of hydrazine hydrate (3.24 g, 64.8 mmol) in tetrahydrofuran (20 mL) at RT. The reaction mixture was stirred for 4 h at RT. The resulting mixture was concentrated under vacuum. The residue was diluted with brine (30 mL) and extracted with dichloromethane (3×30 mL). The combined organic extracts were dried with anhydrous sodium sulfate and filtered. The filtrate was concentrated under vacuum. The residue was purified by silica gel chromatography (100% MeOH) to furnish the title compound as a solid. MS=251.1 (+ESI).

Step 3. Methyl 6-methoxy-2-methylpyrimidine-4-carboxylate

6-Hydroxy-2-methylpyrimidine-4-carboxylic acid (5 g, 32.4 mmol) was added to phosphoryl trichloride (30 mL) at RT and the mixture was stirred at 105° C. for 2 h. After cooling to RT, the solution was concentrated under reduced pressure. MeOH (30 mL) was added to the mixture dropwise at 0° C. and the solution was stirred for 16 h at RT. The solution was concentrated under reduced pressure. The resulting mixture was quenched by the addition of saturated aqueous sodium bicarbonate (50 mL) and the product was extracted with ethyl acetate (2×100 mL). The combined organic extracts were dried with anhydrous sodium sulfate and filtered. The title compound was obtained as a solid and was used in the next step directly without further purification. MS=183.1 (+ESI).

Step 4. Sodium 6-methoxy-2-methylpyrimidine-4-carboxylate

Sodium hydroxide (23.05 mg, 0.576 mmol) was added to a stirred solution of methyl 6-methoxy-2-methylpyrimidine-4-carboxylate (100 mg, 0.549 mmol) in MeOH:H$_2$O=3.5:1 (6 mL). The mixture was stirred at RT for 16 h. MeOH (2 mL) was added to the reaction mixture. The mixture was filtered and then washed with EtOAc (2 mL). The title compound was obtained as a solid. MS=169.0 (+ESI, from parent acid).

Step 5. 6-Chloro-N'-(2-(2-fluoro-4-(trifluoromethyl)phenyl)propanoyl)-2-methylpyrimidine-4-carbohydrazide The title compound was prepared using procedures similar to those described in step 2 of Examples 4 and 5 using thionyl chloride, sodium 6-methoxy-2-methylpyrimidine-4-carboxylate and 2-(2-fluoro-4-(trifluoromethyl)phenyl)propanehydrazide to afford the title compound as a solid. MS=405.2 (+ESI).

Step 6. N'-(2-(2-fluoro-4-(trifluoromethyl)phenyl)propanoyl)-6-methoxy-2-methylpyrimidine-4-carbohydrazide Sodium methoxide (0.327 g, 6.05 mmol) was added to a solution of 6-chloro-N'-(2-(2-fluoro-4-(trifluoromethyl)phenyl)-propanoyl)-2-methylpyrimidine-4-carbohydrazide (0.980 g, 2.42 mmol) in methanol (15 mL). The reaction mixture was stirred for 2 h at 40° C. After cooling to RT, the pH value of the reaction mixture was adjusted to 7 with aqueous hydrochloric acid solution (1 M). The resulting mixture was diluted with brine (50 mL) and extracted with ethyl acetate (3×50 mL). The combined organic extracts were dried with anhydrous sodium sulfate and filtered. The filtrate was concentrated under vacuum. The residue was purified by silica gel chromatography (35% ethyl acetate in petroleum ether) to furnish the title compound as a solid. MS=401.3 (+ESI).

Step 7. 2-(1-(2-Fluoro-4-(trifluoromethyl)phenyl)ethyl)-5-(6-methoxy-2-methylpyrimidin-4-yl)-1,3,4-thiadiazole Phosphorus pentasulfide (0.472 g, 2.12 mmol) was added to a mixture of sodium carbonate (0.144 g, 1.36 mmol) in tetrahydrofuran (6 mL) at 0° C. under nitrogen atmosphere. The reaction mixture was stirred for 10 min at RT and was then added into a solution of N'-(2-(2-fluoro-4-(trifluoromethyl)phenyl)propanoyl)-6-methoxy-2-methylpyrimidine-4-carbohydrazide (0.340 g, 0.849 mmol) in dioxane (6 mL) dropwise with stirring at 80° C. over 2 minutes. The reaction mixture was allowed to stir at 80° C. for 20 h. After cooling to RT, the resulting mixture was diluted with brine (50 mL) and extracted with ethyl acetate (3×50 mL). The combined organic extracts were dried with anhydrous sodium sulfate and filtered. The filtrate was concentrated under vacuum. The residue was purified by silica gel chromatography (35% ethyl acetate in petroleum ether) to furnish the title compound as a solid. MS=399.1 (+ESI).

Step 8. (R)- and (S)-6-(5-(1-(2-fluoro-4-(trifluoromethyl)phenyl)ethyl)-1,3,4-thiadiazol-2-yl)-2-methylpyrimidin-4(3H)-one A solution of hydrogen chloride in ethyl acetate (2.0 mL, 8.00 mmol) was added to a solution of 2-(1-(2-fluoro-4-(trifluoromethyl)phenyl)ethyl)-5-(6-methoxy-2-methylpyrimidin-4-yl)-1,3,4-thiadiazole (0.100 g, 0.251 mmol) in toluene (2.0 mL). The reaction mixture was stirred for 16 h at 100° C. After cooling to RT, the resulting mixture was concentrated under vacuum. The residue was purified by silica gel chromatography (35% ethyl acetate in petroleum ether) to furnish the title compound as a solid. MS=385.2 (+ESI). The enantiopure compounds were obtained by resolution of the racemic title compound by chiral preparative HPLC (Chiralpak IA column; 10% EtOH in hexanes+0.1% TFA). The faster-eluting enantiomer of the title compound was obtained as a solid (Example 4). $^1$H NMR (400 MHz, CDCl$_3$) δ: 7.57-7.48 (m, 1H), 7.51-7.46 (m, 1H), 7.43-7.35 (m, 2H), 5.03 (q, J=7.2 Hz, 1H), 2.57 (s, 3H), 1.93 (d, J=7.2 Hz, 3H). MS=385.2 (+ESI). The slower-eluting enantiomer of the title compound was obtained as a solid (Example 5). $^1$H NMR (400 MHz, CDCl$_3$) δ: 7.57-7.48 (m, 1H), 7.51-7.46 (m, 1H), 7.43-7.35 (m, 2H), 5.03 (q, J=7.2 Hz, 1H), 2.57 (s, 3H), 1.93 (d, J=7.2 Hz, 3H). MS=385.2 (+ESI).

Examples 6 and 7

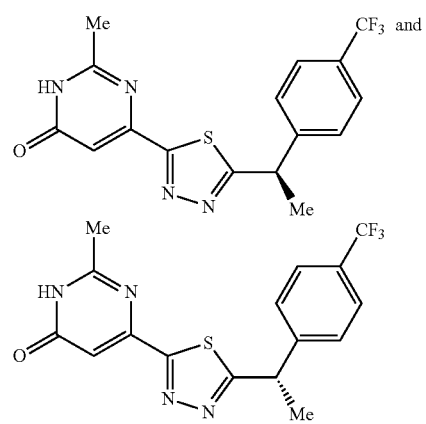

(R)- and (S)-2-methyl-6-(5-(1-(4-(trifluoromethyl)phenyl)ethyl)-1,3,4-thiadiazol-2-yl)pyrimidin-4(3H)-one. (Scheme 4)

Step 1. 6-Methoxy-2-methyl-N-(2-(4-(trifluoromethyl)phenyl)propanoyl)pyramidine-4-carbohydrazide The title compound was prepared using procedures similar to those described in step 2 of Examples 9 and 10 using sodium 6-methoxy-2-methylpyrimidine-4-carboxylate from step 4 of Examples 4 and 5 to afford the title compound as a liquid. MS=383.0 (+ESI).

Step 2. 2-(6-Methoxy-2-methylpyrimidin-4-yl)-5-(1-(4-(trifluoromethyl)phenyl)ethyl)-1,3,4-thiadiazole The title compound was prepared using procedures similar to those described in step 2 of Example 2 using 6-methoxy-2-methyl-N-(2-(4-(trifluoromethyl)phenyl)-propanoyl)pyrimidine-4-carbohydrazide to afford the title compound as a liquid. MS=381.2 (+ESI).

Step 3. (R)- and (S)-2-methyl-6-(5-(1-(4-(trifluoromethyl)phenyl)ethyl)-1,3,4-thiadiazol-2-yl)pyrimidin-4(3H)-one The title compound was prepared using procedures similar to those described in step 5 of Example 2 using 2-(6-methoxy-2-methylpyrimidin-4-yl)-5-(1-(4-(trifluoromethyl)phenyl)ethyl)-1,3,4-thiadiazole to afford the racemic title compound as a solid. MS (+ESI) m/z=367.0. $^1$H NMR (300 MHz, DMSO-d$_6$) δ: 7.73 (d, J=8.1 Hz, 2H), 7.65 (d, J=8.4 Hz, 2H), 6.86 (s, 1H), 4.96-4.90 (m, 1H), 2.28 (s, 3H), 1.80 (d, J=7.5 Hz, 3H). The enantiopure compounds were obtained by resolution of the racemic title compound by chiral preparative HPLC (Chiralpak IA; 50% isopropanol in hexanes+0.1% triethylamine). The faster-eluting enantiomer of the title compound was obtained as a solid (Example 6). $^1$H NMR (300 MHz, CDCl$_3$) δ: 13.05-12.91 (br, 1H), 7.63 (d, J=8.1 Hz, 2H), 7.49 (d, J=8.1 Hz, 2H), 7.33 (s, 1H), 4.75 (q, J=7.2 Hz, 1H), 2.53 (s, 3H), 1.91 (d, J=7.2 Hz, 3H). MS=367.1 (+ESI). The slower-eluting enantiomer of the title compound was obtained as a solid (Example 7). $^1$H NMR (300 MHz, CDCl$_3$) δ: 13.25-12.90 (br, 1H), 7.63 (d, J=7.5 Hz, 2H), 7.50 (d, J=7.5 Hz, 2H), 7.33 (s, 1H), 4.75 (q, J=6.6 Hz, 1H), 2.54 (s, 3H), 1.91 (d, J=6.9 Hz, 3H). MS=367.1 (+ESI).

Example 8

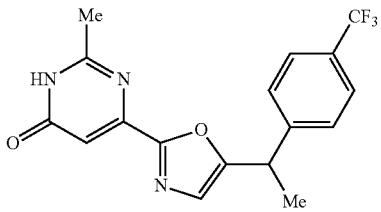 [SMILES: Cc1nc(-c2ncc(C(C)c3ccc(C(F)(F)F)cc3)o2)cc(=O)[nH]1]

2-Methyl-6-(5-(1-(4-(trifluoromethyl)phenyl)ethyl)oxazol-2-yl)pyrimidin-4(3H)-one, (Scheme 5)

Step 1.
1-Chloro-3-(4-(trifluoromethyl)phenyl)butan-2-one

The title compound was prepared using procedures similar to those described in step 3 of Example 2 using 2-(4-(trifluoromethyl)phenyl)propanoic acid to afford the title compound as a liquid. $^1$H NMR (300 MHz, DMSO-d$_6$) δ: 7.71 (d, J=8.1 Hz, 2H), 7.51 (d, J=8.1 Hz, 2H), 4.75-4.47 (m, 2H), 4.18 (q, J=6.9 Hz, 1H), 1.32 (d, J=6.9 Hz, 3H).

Step 2.
1-Azido-3-(4-(trifluoromethyl)phenyl)butan-2-one

Sodium azide (38.9 mg, 0.6 mmol) was added to a solution of 1-chloro-3-(4-(trifluoromethyl)phenyl) butan-2-one (0.100 g, 0.4 mmol) in DMF (2 mL). The resulting solution was stirred for 30 minutes at RT. The resulting mixture was diluted with brine (15 mL) and extracted with ethyl acetate (3×15 mL). The combined organic extracts were dried with anhydrous sodium sulfate and filtered. The filtrate was concentrated under reduced pressure. The title compound was obtained as a liquid and was used in the next step directly without further purification. MS=280.2 (+ESI).

Step 3.
1-Amino-3-(4-(trifluoromethyl)phenyl)butan-2-one

Palladium on carbon (15 mg, 0.14 mmol) was added to a solution of 1-azido-3-(4-(trifluoromethyl)phenyl)butan-2-one (30 mg, 0.1 mmol) in methanol (1 mL) followed by the addition of hydrochloric acid (1 mL, 12.2 mmol). The reaction mixture was degassed with hydrogen 3 times and stirred under hydrogen (1 atm) for 1 h at RT. The resulting mixture was filtered and the filtrate was concentrated under reduced pressure. The title compound was obtained as a solid and was used in the next step directly without further purification. MS=232.0 (+ESI).

Step 4. 6-Chloro-2-methyl-N-(2-oxo-3-(4-(trifluoromethyl)phenyl)butyl)pyrimidine-4-carboxamide Saturated sodium bicarbonate (10 mL) was added to a stirred mixture of 6-chloro-2-methylpyrimidine-4-carbonyl chloride (0.900 g, 4.7 mmol) and 1-amino-3-(4-(trifluoromethyl)phenyl)butan-2-one hydrochloride (0.883 g, 3.3 mmol) in DCM (10 ml) at 0° C. The mixture was stirred at RT for 12 h. The resulting mixture was diluted with DCM (10 mL), washed with brine (2×10 mL), dried with anhydrous sodium sulfate and filtered. The filtrate was concentrated. The residue was purified by silica gel chromatography (0-70% ethyl acetate in petroleum ether) to furnish the title compound as a liquid: MS=386.3/388.1 (+ESI).

Step 5. 2-(6-Chloro-2-methylpyrimidin-4-yl)-5-(1-(4-(trifluoromethyl)phenyl)ethyl)oxazole To 6-chloro-2-methyl-N-(2-oxo-3-(4-(trifluoromethyl)phenyl)buty)pyrimidine-4-carboxamide (0.150 g, 0.4 mmol) were added toluene (3 mL) and phosphorus oxychloride (0.2 mL, 1.9 mmol). The reaction mixture was refluxed for 24 h. The mixture was cooled, and brine (10 mL) was added. The mixture was extracted with ethyl acetate (3×10 mL). The combined organic extracts were washed with water (3×10 mL), dried with anhydrous sodium sulfate, and filtered. The filtrate was concentrated. The residue was purified by silica gel chromatography (0-50% ethyl acetate in petroleum ether) to furnish the title compound as a solid: MS=368.1/370.1 (+ESI).

Step 6. 2-Methyl-6-(5-(1-(4-(trifluoromethyl)phenyl)ethyl)oxazol-2-yl)pyrimidin-4(3H)-one Sodium hydroxide (6.8 mL, 13.6 mmol, 2 M in water) was added to a stirred mixture of 2-(6-chloro-2-methylpyrimidin-4-yl)-5-(1-(4-(trifluoromethyl)phenyl)ethyl)oxazole (40 mg, 0.1 mmol) in tetrahydrofuran (10 mL) at 0° C. The reaction mixture was stirred at RT for 24 h. The resulting mixture was concentrated under reduced pressure. The residue was diluted with ethyl acetate (10 mL), washed with water (3×10 mL), dried with anhydrous sodium sulfate, and filtered. The filtrate was concentrated. The residue was purified by preparative reverse phase HPLC (X Bridge C18 column; 30-70% acetonitrile in water+0.05% TFA) to furnish the title compound as a solid. $^1$H NMR (300 MHz, DMSO-d$_6$) δ: 7.71 (d, J=8.1 Hz, 2H), 7.51 (d, J=8.1 Hz, 2H), 7.30 (s, 1H), 6.70 (s, 1H), 4.49 (q, J=7.2 Hz, 1H), 2.31 (s, 3H), 1.60 (d, J=7.2 Hz, 3H). MS=350.3 (+ESI).

Examples 9 and 10

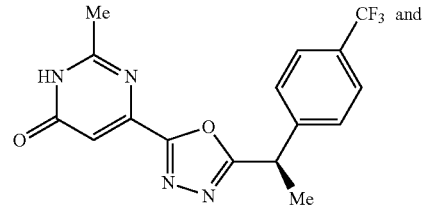

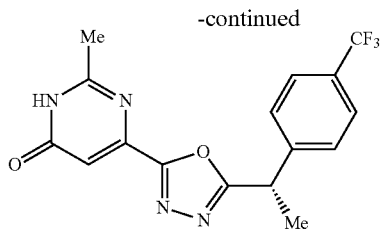

(R)- and (S)-2-methyl-6-(5-(1-(4-(trifluoromethyl)
phenyl)ethyl)-1,3,4-oxadiazol-2-yl)pyrimidin-4(3H)-
one, (Scheme 6)

Step 1.
2-(4-(Trifluoromethyl)phenyl)propanehydrazide

The title compound was prepared using procedures similar to those described in step 2 of Examples 4 and 5 using thionyl chloride, 2-(4-(trifluoromethyl)phenyl)propanoic acid and hydrazine hydrate to afford the title compound as a liquid and was used in the next step directly without further purification. MS=233.4 (+ESI).

Step 2. 2-Methyl-6-oxo-N-(2-(4-(trifluoromethyl)
phenyl)propanoyl)-1,6-dihydropyrimidine-4-carbohydrazide 2-Methyl-6-oxo-1,6-dihydropyrimidine-4-carboxylic acid (0.139 g, 0.9 mmol), 2-(3H-[1,2,3]triazolo[4,5-b]pyridin-3-yl)-1,1,3,3-tetramethylisouronium hexafluorophosphate(V) (0.344 g, 0.9 mmol) and DIEA (0.584 g, 4.5 mmol) were added to a stirred mixture of 2-(4-(trifluoromethyl)phenyl)propanehydrazide (0.300 g, 0.9 mmol) in NMP (3 mL). The mixture was stirred at RT for 2 h. The reaction was quenched with water (30 mL) and extracted with ethyl acetate (3×20 mL). The combined organic extracts were washed with brine (30 mL), dried with anhydrous sodium sulfate and filtered. The filtrate was concentrated under reduced pressure. The residue was purified by silica gel chromatography (0-20% methanol in dichloromethane) to furnish the title compound as a solid: MS=369.3 (+ESI).

Step 3. (R)- and (S)-2-methyl-6-(5-(1-(4-(trifluoromethyl)phenyl)ethyl)-1,3,4-oxadiazol-2-yl)pyrimidin-4(3H)-one 2-Methyl-6-oxo-N-(2-(4-(trifluoromethyl)phenyl)propanoyl)-1,6-dihydropyrimidine-4-carbohydrazide (80.0 mg, 0.2 mmol) was added to a stirred mixture of 1-methoxy-N-triethylammoniosulfonyl-methanimidate (0.129 g, 0.5 mmol) in dioxane (5 mL). The mixture was degassed with nitrogen 3 times. The mixture was heated in a sealed tube at 120° C. for 50 minutes. The mixture was cooled to RT and brine (10 mL) was added. The resulting mixture was extracted with ethyl acetate (3×10 mL). The combined organic extracts were dried with anhydrous sodium sulfate and filtered. The filtrate was concentrated under reduced pressure. The residue was purified by reverse phase preparative HPLC (XBridge C18 column: 5-38% acetonitrile in water+0.05% ammonium bicarbonate) to furnish the racemic title compound as a solid. The enantiopure compounds were obtained by resolution of the racemic title compound by chiral preparative HPLC (Chiralpak IC; 80% ethanol in hexanes). The faster-eluting enantiomer of the title compound was obtained as a solid (Example 9). $^1$H NMR (300 MHz, DMSO-d$_6$) δ: 12.95-12.76 (br, 1H), 7.75 (d, J=8.4 Hz, 2H), 7.59 (d, J=8.4 Hz, 2H), 6.84 (s, 1H), 4.77 (q, J=7.2 Hz, 1H), 2.35 (s, 3H), 1.71 (d, J=7.2 Hz, 3H). MS=351.0 (+ESI). The slower-eluting enantiomer of the title compound was obtained as a solid (Example 10). $^1$H NMR (300 MHz, DMSO-d$_6$) δ: 12.87 (br, 1H), 7.75 (d, J=8.1 Hz, 2H), 7.59 (d, J=8.4 Hz, 2H), 6.84 (s, 1H), 4.77 (q, J=7.5 Hz, 1H), 2.35 (s, 3H), 1.71 (d, J=7.2 Hz, 3H). MS=351.1 (+ESI).

Example 11

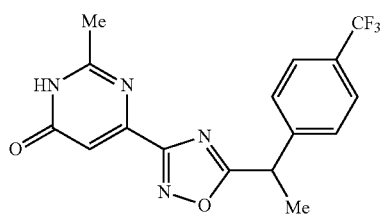 [SMILES: Cc1nc(-c2noc(C(C)c3ccc(C(F)(F)F)cc3)n2)cc(=O)[nH]1]

2-Methyl-6-(5-(1-(4-(trifluoromethyl)phenyl)ethyl)-
1,2,4-oxadiazol-3-yl)pyrimidin-4(3H)-one,
(Scheme 7)

Step 1.
6-Methoxy-2-methylpyrimidine-4-carbonitrile

Dicyanozinc (0.267 g, 2.270 mmol) and zinc (0.049 g, 0.757 mmol) were added to a stirred solution of 4-chloro-6-methoxy-2-methylpyrimidine (0.600 g, 3.78 mmol) in DMA (2.5 mL) at RT. To the mixture were added di-tert-butyl(2',4',6'-triisopropyl-[1,1'-biphenyl]-2-yl)phosphine (0.321 g, 0.757 mmol) and Pd$_2$(dba)$_3$ (0.173 g, 0.189 mmol). The reaction mixture was degassed with nitrogen 3 times and stirred under nitrogen atmosphere for 30 minutes at RT, then stirred for another 1 h at 90° C. The reaction mixture was cooled, diluted with brine (10 mL) and extracted with ethyl acetate (5×6 mL). The combined organic extracts were dried with anhydrous sodium sulfate and filtered. The filtrate was concentrated under reduced pressure. The residue was purified by silica gel chromatography (0-15% ethyl acetate in petroleum ether) to furnish the title compound as a solid. MS=150.4 (+ESI).

Step 2. N'-hydroxy-6-methoxy-2-methylpyrimidine-
4-carboximidamide

Hydroxylamine hydrochloride (189 mg, 2.73 mmol) was added to a solution of 6-methoxy-2-methylpyrimidine-4-carbonitrile (428 mg, 2.87 mmol) in TEA (8 mL, 57.4 mmol). The reaction mixture was stirred for 1 h at 90° C. Methanol (30 mL) was added to the resulting mixture. The resulting mixture was concentrated under reduce pressure. The title compound was obtained as a solid and was used in the next step directly without further purification. MS=183.2 (+ESI).

Step 3. N-((hydroxyimino)(6-methoxy-2-methylpy-
rimidin-4-yl)methyl)-2-(4-(trifluoromethyl)phenyl)
propanamide The title compound was prepared using procedures similar to those described in step 2 of Examples 4 and 5 using thionyl chloride, 2-(4-(trifluoromethyl)phenyl)propanoic acid and N'-hydroxy-6-methoxy-2-methylpyrimidine-4-carboximidamide to afford the title compound as a solid and was used in the next step directly without further purification. MS=383.3 (+ESI).

Step 4. 2-Methyl-6-(5-(1-(4-(trifluoromethyl)phenyl)ethyl)-1,2,4-oxadiazol-3-yl)pyrimidin-4(3H)-one N-((hydroxyimino)(6-methoxy-2-methylpyrimidin-4-yl)methyl)-2-(4-(trifluoromethyl)phenyl)propanamide (120 mg, 0.314 mmol) was added to xylene (2 mL). The reaction mixture was stirred for 2 h at 120° C. After cooling to RT, the reaction mixture was concentrated. The residue was purified by silica gel chromatography (60% ethyl acetate in petroleum ether) to furnish the title compound as a solid. $^1$H NMR (300 MHz, CDCl$_3$) δ: 7.63 (d, J=8.1 Hz, 2H), 7.48 (d, J=8.1 Hz, 2H), 7.19 (s, 1H), 4.56 (q, J=6.9 Hz, 1H), 2.61 (s, 3H), 1.84 (d, J=7.2 Hz, 3H). MS=350.9 (+ESI).

Example 12

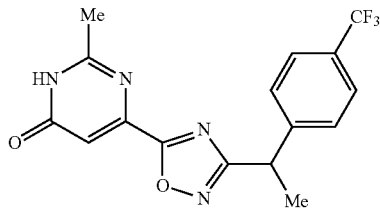 [SMILES: Cc1nc(-c2nc(C(C)c3ccc(C(F)(F)F)cc3)no2)cc(=O)[nH]1]

2-Methyl-6-(3-(1-(4-(trifluoromethyl)phenyl)ethyl)-1,2,4-oxadiazol-5-yl)pyrimidin-4(3H)-one, (Scheme 8)

Step 1. N'-hydroxy-2-(4-(trifluoromethyl)phenyl)propanimidamide

The title compound was prepared using procedures similar to those described in step 2 of Example 11 using 2-(4-(trifluoromethyl)phenyl)propanenitrile to afford the title compound as a liquid. MS=232.7 (+ESI).

Step 2. N-(1-(hydroxyimino)-2-(4-(trifluoromethyl)phenyl)propyl)-6-methoxy-2-methylpyrimidine-4-carboxamide The title compound was prepared using procedures similar to those described in step 2 of Examples 4 and 5 using thionyl chloride, sodium 6-methoxy-2-methylpyrimidine-4-carboxylate and N-hydroxy-2-(4-(trifluoromethyl)phenyl)propanimidamide to afford the title compound as a liquid. MS=383.0 (+ESI).

Step 3. 2-Methyl-6-(3-(1-(4-(trifluoromethyl)phenyl)ethyl)-1,2,4-oxadiazol-5-yl)pyrimidin-4(3H)-one The title compound was prepared using procedures similar to those described in step 8 of Examples 4 and 5 using N-(1-(hydroxyimino)-2-(4-(trifluoromethyl)phenyl)propyl)-6-methoxy-2-methylpyrimidine-4-carboxamide to afford the title compound as a solid. $^1$H NMR (300 MHz, CDCl$_3$) δ: 7.59 (d, J=8.1 Hz, 2H), 7.50 (d, J=8.4 Hz, 2H), 7.21 (s, 1H), 4.46 (q, J=7.2 Hz, 1H), 2.61 (s, 3H), 1.79 (d, J=7.2 Hz, 3H). MS=351.0 (+ESI).

Example 13

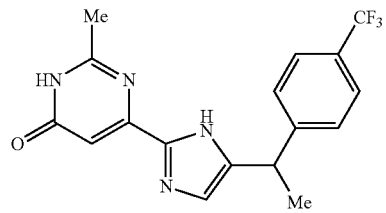 [SMILES: Cc1nc(-c2ncc(C(C)c3ccc(C(F)(F)F)cc3)[nH]2)cc(=O)[nH]1]

2-Methyl-6-(5-(1-(4-(trifluoromethyl)phenyl)ethyl)-1H-imidazol-2-yl)pyrimidin-4(3H)-one, (Scheme 9)

Step 1. 2-Methyl-6-oxo-N-(2-oxo-3-(4-(trifluoromethyl)phenyl)butyl)-1,6-dihydropyrimidine-4-carboxamide The title compound was prepared using procedures similar to those described in step 2 of Examples 9 and 10 using 1-amino-3-(4-(trifluoromethyl)-phenyl)butan-2-one hydrochloride from step 3 of Example 8 to afford the title compound as a liquid. MS=368.1 (+ESI).

Step 2. 2-Methyl-6-(5-(1-(4-(trifluoromethyl)phenyl)ethyl)-1H-imidazol-2-yl)pyrimidin-4(3H)-one Acetic acid ammonia salt (79.0 mg, 1.0 mmol) was added to a mixture of 2-methyl-6-oxo-N-(2-oxo-3-(4-(trifluoromethyl)phenyl)butyl)-1,6-dihydropyrimidine-4-carboxamide (75.0 mg, 0.2 mmol) in xylene (5 mL) and the mixture was stirred at 140° C. for 18 h. After cooling to RT, the solvent was concentrated under reduced pressure. The crude product was purified by preparative reverse phase HPLC (Xbridge RP18 column; 45-55% acetonitrile in water+0.05% ammonium bicarbonate) to furnish the title compound as a solid. $^1$H NMR (300 MHz, DMSO-d$_6$) δ:12.60-12.40 (br, 1H), 7.64 (d, J=8.4 Hz, 2H), 7.51 (d, J=8.1 Hz, 2H), 7.06 (s, 1H), 6.56 (s, 1H), 4.20 (q, J=6.9 Hz, 1H), 2.36 (s, 3H), 1.59 (d, J=7.2 Hz, 3H). MS=349.1 (+ESI).

Examples 14 and 15

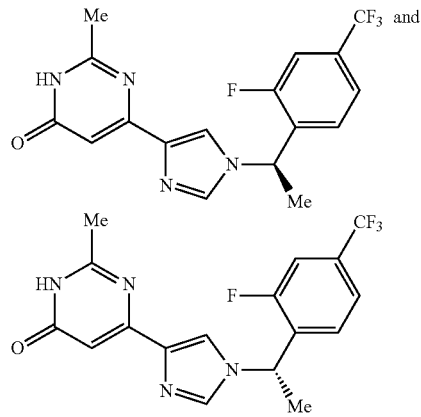

(R)- and (S)-6-(1-(1-(2-fluoro-4-(trifluoromethyl)phenyl)ethyl)-1H-imidazol-4-yl)-2-methylpyrimidin-4(3H)-one, (Scheme 10)

Step 1. 1-(2-fluoro-4-(trifluoromethyl)phenyl)ethanol

To a solution of 1-(2-fluoro-4-(trifluoromethyl)phenyl)ethanone (5 g, 24.26 mmol) in THF (40.4 ml) and MeOH (40.4 ml) at 0° C. was added NaBH$_4$ (2.294 g, 60.6 mmol). After 1 h, the reaction was quenched with saturated aqueous NaHCO$_3$ and water. This mixture was then extracted with EtOAc. The combined organic extracts were washed with brine, dried over Na$_2$SO$_4$ and concentrated.

$^1$H NMR (500 MHz, DMSO-d$_6$) δ: 7.74 (m, 1H), 7.57 (m, 2H), 5.51 (d, J=4.5 Hz, 1H), 5.02 (m, 1H), 1.34 (d, J=6.5 Hz, 3H).

Step 2. 1-(1-bromoethyl)-2-fluoro-4-(trifluoromethyl)benzene

To a flask containing 1-(2-fluoro-4-(trifluoromethyl)phenyl)ethanol (4.65 g, 22.34 mmol) at 0° C. was added tribromophosphine (4.5 ml, 47.7 mmol) dropwise. The reaction was removed from the ice bath and stirred overnight at RT. The reaction was cooled to 0° C. and quenched with saturated aqueous NaHCO$_3$ solution followed by solid NaHCO$_3$. The mixture was then extracted with EtOAc and the organic layers were then washed with brine, dried over Na$_2$SO$_4$ and concentrated.

$^1$H NMR (500 MHz, DMSO-d$_6$) δ: 7.67 (t, 1H), 7.44 (d, J=8 Hz, 1H), 7.33 (d, J=10 Hz, 1H), 5.46 (q, J=7 Hz, 1H), 2.06 (d, J=7 Hz, 3H).

Step 3. 4-bromo-1-(1-(2-fluoro-4-(trifluoromethyl)phenyl)ethyl)-1H-imidazole

To a RT solution of 4-bromo-1H-imidazole (303 mg, 2.062 mmol) in DMF (6872 μl) was added cesium carbonate (806 mg, 2.474 mmol) followed by 1-(1-bromoethyl)-2-fluoro-4-(trifluoromethyl)benzene (726 mg, 2.68 mmol). The reaction was stirred overnight at RT. The reaction was diluted with EtOAc and washed with brine. The organic layer was dried over Na$_2$SO$_4$ and concentrated. The residue was purified by silica gel chromatography (0-10% MeOH in DCM) to furnish the title compound as a liquid. LCMS=338.85 (M+1).

Step 4. (R)- and (S)-6-(1-(1-(2-fluoro-4-(trifluoromethyl)phenyl)ethyl)-1H-imidazol-4-yl)-2-methyl-pyrimidin-4(3H)-one 4-Bromo-1-(1-(2-fluoro-4-(trifluoromethyl)phenyl)ethyl)-1H-imidazole (555 mg, 1.646 mmol), 4,4,4',4',5,5,5',5'-octamethyl-2,2'-bi(1,3,2-dioxaborolane) (418 mg, 1.646 mmol), potassium acetate (268 mg, 2.73 mmol), 2-dicyclohexylphosphino-2',6'-dimethoxybiphenyl (67.6 mg, 0.165 mmol), and Pd$_2$(dba)$_3$ (37.7 mg, 0.041 mmol) were combined in degassed dioxane (3.98 mL) and heated to 105° C. for 2.5 h. Then degassed potassium phosphate tribasic solution (1.664 mL of 5N, 8.23 mmol) and 4-chloro-6-((4-methoxybenzyl)oxy)-2-methyl-pyrimidine (362 mg, 1.366 mmol) in degassed dioxane (0.5 mL) were added and the reaction was heated at 105° C. overnight. The reaction was diluted with EtOAc. The organic layer was washed with brine, dried over Na$_2$SO$_4$, and concentrated. The residue was then purified by silica gel chromatography (0-40% (3:1 EtOAc:EtOH) in hexanes) to furnish the PMB-protected title compound after concentration of the product-containing fractions. The residue was then dissolved in DCM (3 mL) and TFA (3 mL, 38.9 mmol) was added. After 2 h, the reaction was concentrated and diluted with DCM. The DCM layer was washed with saturated aqueous NaHCO$_3$ (3×) and brine (1×). The organic layer was dried over Na$_2$SO$_4$ and concentrated. The residue was purified by silica gel chromatography (0-100% (3:1 EtOAc:EtOH) in hexanes) to furnish the racemic title compound. The racemic title compound was then resolved into the enantiomers by chiral SFC chromatography (Chiralpak AD-H; 25% 1:1 acetonitrile: methanol in CO$_2$+0.2% diethylamine). The faster-eluting enantiomer of the title compound was obtained as a solid (Example 14). $^1$H NMR (500 MHz, DMSO-d$_6$) δ: 12.17 (s, 1H), 7.96 (s, 1H), 7.81 (s, 1H), 7.73 (d, J=10.5 Hz, 1H), 7.64 (d, J=8.5 Hz, 1H), 7.52 (t, J=7.5 Hz, 1H), 6.47 (s, 1H), 5.93 (q, J=7 Hz, 1H), 2.27 (s, 3H), 1.87 (d, J=7 Hz, 3H). MS=366.92 (M+1).

The slower-eluting enantiomer of the title compound was obtained as a solid (Example 15). $^1$H NMR (500 MHz, DMSO-d$_6$) δ: 12.17 (s, 1H), 7.96 (s, 1H), 7.81 (s, 1H), 7.73 (d, J=10.5 Hz, 1H), 7.64 (d, J=8.5 Hz, 1H), 7.53 (t, J=7.5 Hz, 1H), 6.47 (s, 1H), 5.93 (q, J=7 Hz, 1H), 2.27 (s, 3H), 1.87 (d, J=7 Hz, 3H). MS=366.94 (M+1).

TABLE 1

The following compounds were prepared using procedures similar to those described for Examples 14 and 15 using the appropriate starting materials.

| Example No. | Structure | IUPAC Name | Exact Mass [M + H]$^+$ | Chiral column |
|---|---|---|---|---|
| 16 | (structure) | (R)- or (S)-2-methyl-6-(1-(1-(4-(trifluoromethyl)phenyl)ethyl)-1H-imidazol-4-yl)pyrimidin-4(3H)-one | Calc'd 349.1, Found 349.0 | Chiralpak IA |
| 17 | (structure) | (R)- or (S)-2-methyl-6-(1-(1-(4-(trifluoromethyl)phenyl)ethyl)-1H-imidazol-4-yl)pyrimidin-4(3H)-one | Calc'd 349.1, Found 349.0 | Chiralpak IA |

TABLE 1-continued

The following compounds were prepared using procedures similar to those described for Examples 14 and 15 using the appropriate starting materials.

| Example No. | Structure | IUPAC Name | Exact Mass [M + H]⁺ | Chiral column |
|---|---|---|---|---|
| 18 | (structure shown) | (R)- or (S)-2-(3,4-dimethoxybenzyl)-6-(1-(1-(2-fluoro-4-(trifluoromethyl)phenyl)ethyl)-1H-imidazol-4-yl)pyrimidin-4(3H)-one | Calc'd 503.1, Found 503.0 | Chiralpak OJ |
| 19 | (structure shown) | (R)- or (S)-2-(3,4-dimethoxybenzyl)-6-(1-(1-(2-fluoro-4-(trifluoromethyl)phenyl)ethyl)-1H-imidazol-4-yl)pyrimidin-4(3H)-one | Calc'd 503.1, Found 503.0 | Chiralpak OJ |

Racemic products were separated using the chiral columns specified in the table. Where an "*" appears in any structure in a table it is intended to indicate a single stereoisomer where the absolute stereochemistry has not been determined.

Example 20

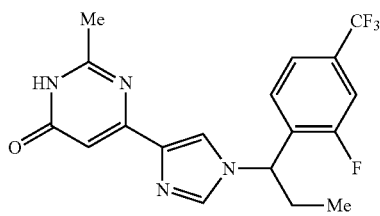 [SMILES: CCC(c1ccc(C(F)(F)F)cc1F)n1cnc(-c2cc(=O)[nH]c(C)n2)c1]

6-(1-(1-(2-Fluoro-4-(trifluoromethyl)phenyl)propyl)-1H-imidazol-4-yl)-2-methylpyrimidin-4(3H)-one, (Scheme 11)

Step 1. 1-(2-Fluoro-4-(trifluoromethyl)phenyl)propan-1-ol

To a solution of 2-fluoro-4-(trifluoromethyl)benzaldehyde (1.00 g, 5.2 mmol) in THF (15 mL) was added dropwise ethylmagnesium bromide (3.47 mL, 10.4 mmol) at −78° C. The reaction mixture was stirred at −78° C. for 20 min and stirred for additional 1 h at RT. The resulting mixture was quenched with water (150 mL) and extracted with DCM (5×150 mL). The combined organic extracts were washed with brine (100 mL), dried with anhydrous sodium sulfate and filtered. The filtrate was concentrated under reduced pressure. The residue was purified by silica gel chromatography (10-40% of ethyl acetate in petroleum ether) to furnish the title compound as a solid. ¹H NMR (400 MHz, DMSO-$d_6$) δ: 7.74-7.71 (m, 1H), 7.59 (d, J=9.2 Hz, 2H), 5.48 (d, J=4.4 Hz, 1H), 4.84-4.79 (m, 1H), 1.70-1.58 (m, 2H), 0.86 (t, J=7.2 Hz, 3H).

Step 2. 4-Methoxy-2-methyl-6-(1-trityl-1H-imidazol-4-yl)pyrimidine

The title compound was prepared using procedures similar to those described in step 1 of Example 29 using 4-(tributylstannyl)-1-trityl-1H-imidazole, 4-chloro-6-methoxy-2-methylpyrimidine to afford the title compound as a solid. MS=433.3 (+ESI).

Step 3. 4-(1H-imidazol-4-yl)-6-methoxy-2-methylpyrimidine

To a solution of 4-methoxy-2-methyl-6-(1-trityl-1H-imidazol-4-yl)pyrimidine (1.45 g, 3.4 mmol) in DCM (20 mL) was added TFA (1.29 mL, 16.8 mmol). The reaction solution was stirred at RT for 3 h. The resulting mixture was concentrated under reduced pressure. The residue was diluted with DCM (200 mL) and washed with saturated $Na_2CO_3$ (50 mL). The separated organic extracts were dried with anhydrous sodium sulfate and filtered. The filtrate was concentrated under reduced pressure. The title compound was obtained as a solid and was used in next step directly without further purification. MS=191.0 (+ESI).

Step 4. 4-(1-(1-(2-Fluoro-4-(trifluoromethyl)phenyl)propyl)-1H-imidazol-4-yl)-6-methoxy-2-methylpyrimidine To a solution of 4-(1H-imidazol-4-yl)-6-methoxy-2-methylpyrimidine (0.300 g, 0.8 mmol) in THF (10 mL) were added 1-(2-fluoro-4-(trifluoromethyl)phenyl)propan-1-ol (0.350 g, 1.6 mmol), $PPh_3$ (0.621 g, 2.4 mmol) and DIAD (0.46 mL, 2.4 mmol) at 0° C. The reaction mixture was stirred at RT for 16 h. The resulting mixture was concentrated under reduced pressure. The residue was purified by silica gel chromatography (45-70% of ethyl acetate in petroleum ether) to furnish the title compound as a solid. MS=395.1 (+ESI).

Step 5. 6-(1-(1-(2-Fluoro-4-(trifluoromethyl)phenyl)propyl)-1H-imidazol-4-yl)-2-methylpyrimidin-4(3H)-one To a solution of 4-(1-(1-(2-fluoro-4-(trifluoromethyl)phenyl)propyl)-1H-imidazol-4-yl)-6-methoxy-2-methylpyrimidine (0.400 g, 0.3 mmol) in toluene (4 mL) was added a solution of saturated HCl in ethyl acetate (8 mL). The reaction mixture was stirred at 100° C. for 1.5 h. The resulting mixture was cooled and concentrated under reduced pressure. The residue was purified by preparative reverse phase HPLC (Xbridge C18 column; 34% acetonitrile in water+0.05% TFA) to furnish the title compound as a solid. $^1$H NMR (400 MHz, CD$_3$OD) δ: 9.44 (s, 1H), 8.12 (s, 1H), 7.69-7.64 (m, 1H), 7.60-7.54 (m, 1H), 7.45-7.42 (m, 1H), 6.74 (t, J=7.6 Hz, 1H), 6.55 (s, 1H), 2.60-2.51 (m, 1H), 2.45 (s, 3H), 2.42-2.35 (m, 1H), 1.09 (t, J=7.2 Hz, 3H). MS=381.1 (+ESI).

Example 21

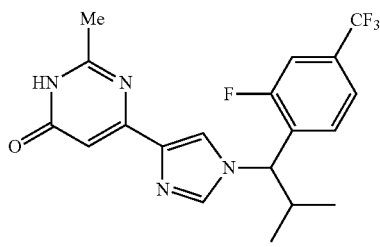 [SMILES: Cc1nc(-c2cn(C(c3ccc(C(F)(F)F)cc3F)C(C)C)cn2)cc(=O)[nH]1]

6-(1-(1-(2-Fluoro-4-(trifluoromethyl)phenyl)-2-methylpropyl)-1H-imidazol-4-yl)-2-methylpyrimidin-4(3H)-one, (Scheme 11)

Step 1. 4-(1-(1-(2-Fluoro-4-(trifluoromethyl)phenyl)-2-methylpropyl)-1H-imidazol-4-yl)-6-methoxy-2-methylpyrimidine The title compound was prepared using procedures similar to those described in step 4 of Example 20 using 4-(1H-imidazol-4-yl)-6-methoxy-2-methylpyrimidine and 1-(2-fluoro-4-(trifluoromethyl)phenyl)-2-methylpropan-1-ol to afford the title compound as a liquid. MS=409.2 (+ESI).

Step 2. 6-(1-(1-(2-Fluoro-4-(trifluoromethyl)phenyl)-2-methylpropyl)-1H-imidazol-4-yl)-2-methylpyrimidin-4(3H)-one The title compound was prepared using procedures similar to those described in step 5 of Example 2 using 4-(1-(1-(2-fluoro-4-(trifluoromethyl)phenyl)-2-methylpropyl)-1H-imidazol-4-yl)-6-methoxy-2-methylpyrimidine to afford the title compound as a solid. $^1$H NMR (300 MHz, DMSO-d$_6$) δ: 12.15-11.98 (br, 1H), 8.11-8.01 (m, 1H), 7.98 (s, 1H), 7.90 (s, 1H), 7.76-7.67 (m, 2H), 6.46 (s, 1H), 5.35 (d, J=11.4 Hz, 1H), 2.95-2.80 (m, 1H), 2.29 (s, 3H), 0.86 (d, J=6.6 Hz, 3H), 0.83 (d, J=7.2 Hz, 3H). MS=395.2 (+ESI).

Example 22

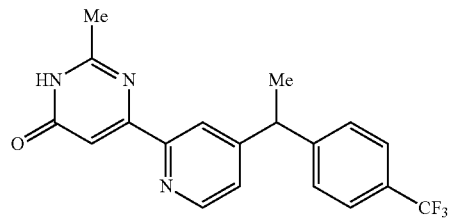 [SMILES: Cc1nc(-c2cc(C(C)c3ccc(C(F)(F)F)cc3)ccn2)cc(=O)[nH]1]

2-methyl-6-(4-(1-(4-(trifluoromethyl)phenyl)ethyl)pyridin-2-yl)pyrimidin-4(3H)-one (Scheme 12)

Step 1. Ethyl 3-(4-chloropyridin-2-yl)-3-oxopropanoate 1,1'-Carbonyldiimidazole (1.24 g, 7.62 mmol) was added to a stirred solution of 4-chloropicolinic acid (1.00 g, 6.35 mmol) in THF (30 mL) at RT. The reaction mixture was stirred at RT for 1 h. To the reaction solution were added magnesium chloride (0.604 g, 6.35 mmol) and potassium 3-ethoxy-3-oxopropanoate (1.08 g, 6.35 mmol) at RT. The reaction mixture was stirred at RT for 3 h. The resulting mixture was neutralized by aqueous hydrochloride acid (2N), diluted with brine (50 mL) and extracted with ethyl acetate (3×30 mL). The combined organic extracts were dried with anhydrous sodium sulfate and filtered. The filtrate was concentrated. The residue was purified by silica gel chromatography (0-10% ethyl acetate in petroleum ether) to furnish the title compound as a liquid. MS=227.7/229.7 (+ESI).

Step 2. 6-(4-Chloropyridin-2-yl)-2-methylpyrimidin-4(3H)-one

Acetimidamide hydrochloride (0.731 g, 7.73 mmol) was added to a stirred solution of ethyl 3-(4-chloropyridin-2-yl)-3-oxopropanoate (0.440 g, 1.933 mmol) in EtOH (60 mL) at RT. To the mixture was added sodium methoxide (0.522 g, 9.66 mmol). The reaction mixture was refluxed for 6 h. After cooling to RT, the reaction mixture was concentrated under reduced pressure. The residue was diluted with water (100 mL) and extracted with ethyl acetate (3×50 mL). The combined organic extracts were washed with brine (100 mL), dried with anhydrous sodium sulfate and filtered. The filtrate was concentrated under reduced pressure. The residue was purified by silica gel chromatography (30-40% ethyl acetate in petroleum ether) to furnish the title compound as a liquid. MS=222.0/224.0 (+ESI).

Step 3. 2-Methyl-6-(4-(1-(4-(trifluoromethyl)phenyl)vinyl)pyridin-2-yl)pyrimidin-4(3H)-one 4,4,5,5-Tetramethyl-2-(1-(4-(trifluoromethyl)phenyl)vinyl)-1,3,2-dioxaborolane (108 mg, 0.180 mmol) and aqueous sodium carbonate (2 N, 0.541 mL, 1.083 mmol) were added to a stirred solution of 6-(4-chloropyridin-2-yl)-2-methylpyrimidin-4(3H)-one (80.0 mg, 0.361 mmol) in dioxane (4 mL) at RT. To the reaction solution was added tetrakis(triphenyl-phosphine)palladium(0) (41.7 mg, 0.0360 mmol). The reaction mixture was degassed with nitrogen 3 times and refluxed under an atmosphere of nitrogen for 1 h.

The reaction mixture was cooled, diluted with brine (6 mL) and extracted with ethyl acetate (5×5 mL). The combined organic extracts were dried with anhydrous sodium sulfate and filtered. The filtrate was concentrated under reduced pressure. The filtrate was concentrated under reduced pressure. The residue was purified by silica gel chromatography (40-50% methanol in dichloromethane). The product containing fractions were combined and concentrated and the resulting residue was purified by reverse phase chromatography (C18 silica gel; 50-80% methanol in water) to furnish the title compound as a solid. MS=358.1 (+ESI).

Step 4. 2-Methyl-6-(4-(1-(4-(trifluoromethyl)phenyl)ethyl)pyridin-2-yl)pyrimidin-4(3H)-one 10% Palladium on carbon (5.00 mg) was added to a stirred solution of 2-methyl-6-(4-(1-(4-(trifluoromethyl)phenyl)vinyl)pyridin-2-yl)pyrimidin-4(3H)-one (45.0 mg, 0.076 mmol) in ethanol (8 mL) at RT. The reaction mixture was degassed with hydrogen 3 times and stirred under hydrogen (1.0 atm) for 3 h at RT. The mixture was filtered. The filter cake was washed with 1:1 methanol:dichloromethane (5×2 mL). The combined filtrate was concentrated under reduced pressure. The residue was purified by preparative reverse phase HPLC (Sunfire C18 column; 45-65% acetonitrile in water+0.05% ammonium bicarbonate) to furnish the title compound as a solid. $^1$H NMR (300 MHz, DMSO-$d_6$) δ:12.63-12.44 (br, 1H), 8.60 (d, J=5.1 Hz, 1H), 8.14 (s, 1H), 7.69 (d, J=8.0 Hz, 2H), 7.53 (d, J=8.0 Hz, 2H), 7.47-7.33 (m, 1H), 7.03 (s, 1H), 4.46 (q, J=7.2 Hz, 1H), 2.37 (s, 3H), 1.65 (d, J=7.2 Hz, 3H). MS=360.1 (+ESI).

Examples 23 and 24

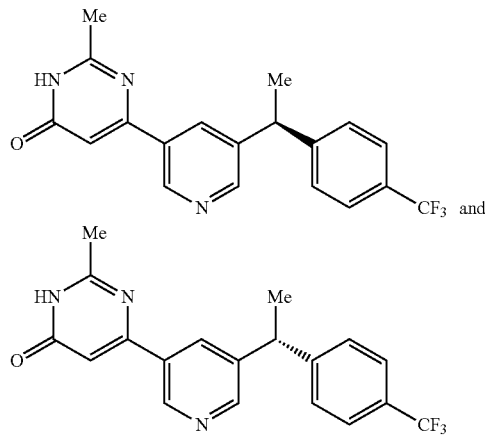

(R)- and (S)-2-Methyl-6-(5-(1-(4-(trifluoromethyl)phenyl)ethyl)pyridin-3-yl)pyrimidin-4(3H)-one, (Scheme 13)

Step 1. (5-Chloropyridin-3-yl)(4-(trifluoromethyl)phenyl)methanol n-Butyllithium (2.063 ml, 5.16 mmol) was added to −40° C. solution of 1-bromo-4-(trifluoromethyl)benzene (0.722 ml, 5.16 mmol) in THF (30 ml) and this solution was stirred at −40° C. for 1 h. A solution of 5-chloronicotinaldehyde (730 mg, 5.16 mmol) in THF (5 mL) was added and the solution was stirred at −40° C. for 1 h and then at 0° C. for 1 h. The reaction was then quenched with saturated aqueous NH$_4$Cl solution. The product was extracted with ethyl acetate. The organic extract was dried over Na$_2$SO$_4$, filtered, and concentrated. No further purification is necessary. $^1$H NMR (500 MHz, CDCl$_3$) δ: 8.54 (s, 1H), 8.48 (s, 1H), 7.78 (s, 1H), 7.66 (d, J=8 Hz, 2H), 7.53 (d, J=8 Hz, 2H), 5.97 (s, 1H), 3.55 (broad s, 1H).

Step 2. (5-(6-((4-Methoxybenzyl)oxy)-2-methylpyrimidin-4-yl)pyridin-3-yl)(4-(trifluoromethyl)phenyl)methanol (5-Chloropyridin-3-yl)(4-(trifluoromethyl)phenyl)methanol (500 mg, 1.738 mmol), 4,4,4',4',5,5,5',5'-octamethyl-2,2'-bi(1,3,2-dioxaborolane) (441 mg, 1.738 mmol), potassium acetate (171 mg, 1.738 mmol), 2-dicyclohexylphosphino-2',6'-dimethoxybiphenyl (71.4 mg, 0.174 mmol), and Pd$_2$(dba)$_3$ (39.8 mg, 0.043 mmol) were combined in degassed dioxane (6 ml) and heated to 105° C. for 4 h. Then potassium phosphate tribasic (1.757 ml, 8.69 mmol) and 4-chloro-6-((4-methoxybenzyl)oxy)-2-methylpyrimidine (391 mg, 1.477 mmol) were added and the reaction was heated at 105° C. for an additional 16 h. The reaction was cooled to RT, filtered through silica gel eluting with ethyl acetate, and concentrated. The crude material was then purified by silica gel chromatography (0-70% ethyl acetate in hexanes). MS=482.07 (M+1).

Step 3. (5-(6-((4-Methoxybenzyl)oxy)-2-methylpyrimidin-4-yl)pyridin-3-yl)(4-(trifluoromethyl)phenyl)methyl methanesulfonate Methanesulfonyl chloride (0.061 ml, 0.777 mmol) was added to 0° C. solution of (5-(6-((4-methoxybenzyl)oxy)-2-methylpyrimidin-4-yl)pyridin-3-yl)(4-(trifluoromethyl)phenyl)methanol (340 mg, 0.706 mmol) and triethylamine (0.108 ml, 0.777 mmol) in CPME (0.8 ml). The reaction was allowed to warm to RT overnight. The reaction was diluted with ether and the precipitate was filtered off. The eluent was concentrated to yield the title compound which was used directly in the next step without further purification.

Step 4. 2-Methyl-6-(5-(1-(4-(trifluoromethyl)phenyl)ethyl)pyridin-3-yl)pyrimidin-4(3H)-one Methylmagnesium bromide (0.233 ml, 0.700 mmol; 3.0 M in Et$_2$O) was added to a solution of (5-(6-((4-methoxybenzyl)oxy)-2-methylpyrimidin-4-yl)pyridin-3-yl)(4-(trifluoromethyl)phenyl)methyl methanesulfonate (196 mg, 0.35 mmol) and copper(I) bromide-dimethyl sulfide complex (36.0 mg, 0.175 mmol) in THF (2 ml) cooled to 0° C. After 30 minutes, 2 equivalents more of methylmagnesium bromide was added. The reaction was quenched with saturated aqueous NH$_4$Cl solution. The product was extracted with ethyl acetate. The extracts were dried over Na$_2$SO$_4$, filtered and concentrated. The PMB-protected title compound was purified by silica gel chromatography (0-30% ethyl acetate in hexanes). The product-containing fractions were concentrated and treated with TFA (1 ml) in DCM (1 ml). After 10 min the volatiles were removed and the product was purified by reverse phase chromatography (Biotage 12g C-18 SNAP cartridge; 10-60% acetonitrile in water+0.05% TFA). The product-containing fractions were concentrated and partioned between DCM and saturated aqueous NaHCO$_3$. The organic extract was dried over Na$_2$SO$_4$, filtered, and concentrated to provide the free base. The racemic title compound was then resolved into the enantiomers by chiral SFC chromatography (Chiralpak AD; 60% MeOH in CO$_2$+0.2% NH$_4$OH). The faster-eluting enantiomer of the title compound was obtained as a solid (Example 23). $^1$H NMR (500 MHz, DMSO-$d_6$) δ: 13.0-12.1

(broad, 1H), 9.03 (d, J=1.5 Hz, 1H), 8.62 (d, J=2.0 Hz, 1H), 8.28 (dd, J=1.5 Hz, J=2.0 Hz, 1H), 7.66 (d, J=8 Hz, 2H), 7.57 (d, J=8 Hz, 2H), 6.88 (s, 1H), 4.44 (q, J=7 Hz, 1H), 2.35 (s, 3H), 1.68 (d, J=7 Hz, 3H). MS=360.1 (M+1). The slower-eluting enantiomer of the title compound was obtained as a solid (Example 24). $^1$H NMR (500 MHz, DMSO-$d_6$) δ: 13.7-12.2 (broad, 1H), 9.03 (d, J=1.5 Hz, 1H), 8.62 (d, J=2.0 Hz, 1H), 8.28 (dd, J=1.5 Hz, J=2.0 Hz, 1H), 7.66 (d, J=8 Hz, 2H), 7.57 (d, J=8 Hz, 2H), 6.88 (s, 1H), 4.44 (q, J=7 Hz, 1H), 2.35 (s, 3H), 1.68 (d, J=7 Hz, 3H). MS=360.1.

Example 25

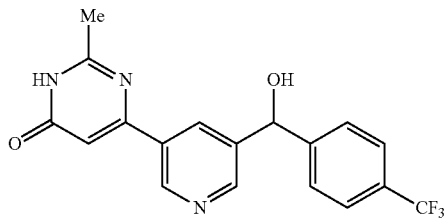 [SMILES: Cc1nc(-c2cncc(C(O)c3ccc(C(F)(F)F)cc3)c2)cc(=O)[nH]1]

6-(5-(Hydroxy(4-(trifluoromethyl)phenyl)methyl) pyridin-3-yl)-2-methylpyrimidin-4(3H)-one, (Scheme 14)

A solution of (5-(6-((4-methoxybenzyl)oxy)-2-methylpyrimidin-4-yl)pyridin-3-yl)(4-(trifluoromethyl)phenyl) methanol (40 mg, 0.083 mmol) in DCM (1 ml) was treated with TFA (1 ml, 12.98 mmol). When the reaction was complete, as judged by LCMS, the reaction was concentrated under reduced pressure and directly purified by reverse phase chromatography (Biotage 30g C-18 Cartridge; 10-60% acetonitrile in water+0.05% TFA) to afford the title compound. $^1$H NMR (500 MHz, DMSO-$d_6$) δ: 12.88-12.30 (broad, 1H), 9.10 (s, 1H), 8.74 (s, 1H), 8.48 (s, 1H), 7.70 (d, J=7.5 Hz, 2H), 7.67 (d, J=7.5 Hz, 2H), 6.87 (s, 1H), 7.00-5.80 (broad, 1H), 6.01 (s, 1H), 2.36 (s, 3H). MS=362.0 (M+1).

Example 26

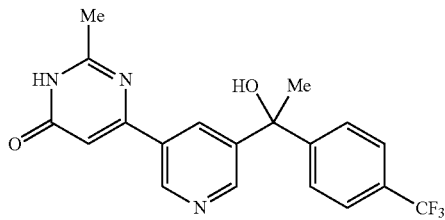 [SMILES: Cc1nc(-c2cncc(C(C)(O)c3ccc(C(F)(F)F)cc3)c2)cc(=O)[nH]1]

6-(5-(1-Hydroxy-1-(4-(trifluoromethyl)phenyl)ethyl) pyridin-3-yl)-2-methylpyrimidin-4(3H)-one, (Scheme 15)

Dess-Martin periodinane (106 mg, 0.249 mmol) was added to a stirring suspension of (5-(6-((4-methoxybenzyl) oxy)-2-methylpyrimidin-4-yl)pyridin-3-yl)(4-(trifluoromethyl)phenyl)methanol (100 mg, 0.208 mmol) and sodium bicarbonate (174 mg, 2.077 mmol) in DCM (2 ml) cooled to 0° C. The reaction was stirred at 0° C. until judged to be complete by LCMS. The mixture was partioned between saturated aqueous NaHCO$_3$ and DCM. The organic extract was dried over Na$_2$SO$_4$, filtered, and concentrated. The crude ketone was then dissolved in THF (2.000 ml) and cooled to 0° C. before being treated with methylmagnesium bromide (0.138 ml, 3.0 M in Et$_2$O 0.415 mmol). After 1 h, the reaction was quenched with saturated aqueous NH$_4$Cl solution and the product was extracted with ethyl acetate. The extracts were dried over Na$_2$SO$_4$, filtered, and concentrated. The crude material was then treated with TFA (1 ml, 12.98 mmol) in DCM (1 ml). Upon completion of the reaction as judged by LCMS, the organic solvents were removed and the product was purified directly by reverse phase chromatography (Biotage 30g SNAP C-18 cartridge; 0-55% acetonitrile in water+0.05% TFA). $^1$H NMR (500 MHz; DMSO-$d_6$) δ: 12.82-12.26 (broad, 1H), 9.09 (d, J=1.5 Hz, 1H), 8.78 (d, J=2 Hz, 1H), 8.54 (dd, J=2 Hz, J=1.5 Hz, 1H), 7.27 (d, J=8.5 Hz, 2H), 7.68 (d, J=8.5 Hz, 2H), 6.92 (s, 1H), 2.36 (s, 3H), 1.97 (s, 3H). MS=376.0 (M+1).

Example 27

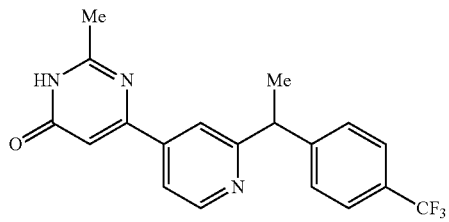 [SMILES: Cc1nc(-c2ccnc(C(C)c3ccc(C(F)(F)F)cc3)c2)cc(=O)[nH]1]

2-Methyl-6-(2-(1-(4-(trifluoromethyl)phenyl)ethyl) pyridin-4-yl)pyrimidin-4(3H)-one, (Scheme 16)

Step 1. (4-Chloropyridin-2-yl)(4-(trifluoromethyl) phenyl)methanol n-Butyllithium (8.00 ml, 20.00 mmol) was added to −40° C. solution of 1-bromo-4-(trifluoromethyl)benzene (2.80 ml, 20 mmol) in THF (30 ml) and this solution was stirred at −40° C. for 1 h. A solution of 4-chloropicolinaldehyde (2.83 g, 20.00 mmol) in THF (5 mL) was added and the solution was stirred at −40° C. for 1 h and then at 0° C. for 1 h. The reaction was then quenched with saturated aqueous NH$_4$Cl solution. The product was extracted with ethyl acetate. The extracts were dried over Na$_2$SO$_4$, filtered, and concentrated. The product was then purified by silica gel chromatography (10-60% ethyl acetate in hexanes). $^1$H NMR (500 MHz, CDCl$_3$) δ: 8.52 (d, J=5.5 Hz, 1H), 7.66 (d, J=8.5 Hz, 2H), 7.57 (d, J=8.5 Hz, 2H), 7.31-7.29 (m, 2H), 5.87 (s, 1H).

Step 2. (4-(6-((4-Methoxybenzyl)oxy)-2-methylpyrimidin-4-yl)pyridin-2-yl)(4-(trifluoromethyl)phenyl)methanol (4-Chloropyridin-2-yl)(4-(trifluoromethyl)phenyl)methanol (300 mg, 1.04 mmol), 4,4,4',4',5,5,5',5'-octamethyl-2,2'-bi(1,3,2-dioxaborolane) (265 mg, 1.043 mmol), potassium acetate (102 mg, 1.043 mmol), 2-dicyclohexylphosphino-2',6'-dimethoxy-biphenyl (42.8 mg, 0.104 mmol), and Pd$_2$(dba)$_3$ (23.87 mg, 0.026 mmol) were combined in degassed dioxane (3.5 ml) and heated to 105° C. for 4 h. Then potassium phosphate tribasic (1.043 ml, 5.21 mmol) and 4-chloro-6-((4-methoxybenzyl)oxy)-2-methylpyrimidine (232 mg, 0.875 mmol) were added and the reaction was heated at 105° C. for an additional 16 h. The reaction was cooled to RT, filtered through silica gel eluting with ethyl acetate, and concentrated. The crude material was then purified by silica gel chromatography (ISCO 40 g silica cartridge; 0-40% ethyl acetate in hexanes) to furnish the title compound. MS=482.0 (M+1).

Step 3. (4-(6-((4-Methoxybenzyl)oxy)-2-methylpyrimidin-4-yl)pyridin-2-yl)(4-(trifluoromethyl)phenyl)methyl methanesulfonate Methanesulfonyl chloride (0.013 ml, 0.171 mmol) was added to 0° C. solution of (4-(6-((4-methoxybenzyl)oxy)-2-methylpyrimidin-4-yl)pyridin-2-yl)(4-(trifluoromethyl)phenyl)methanol (75 mg, 0.156 mmol) and triethylamine (0.024 ml, 0.171 mmol) in CPME (0.8 ml). The reaction was allowed to warm to RT overnight. The reaction was diluted with ether, the precipitate was filtered off, and the eluent was concentrated to yield the title compound which was used directly in the next step.

Step 4. 2-Methyl-6-(2-(1-(4-(trifluoromethyl)phenyl)ethyl)pyridin-4-yl)pyrimidin-4(3H)-one Methylmagnesium bromide (0.052 ml, 0.156 mmol) was added to a solution of (4-(6-((4-methoxybenzyl)oxy)-2-methylpyrimidin-4-yl)pyridin-2-yl)(4-(trifluoromethyl)phenyl)methyl methanesulfonate (43.6 mg, 0.078 mmol) and copper(I) bromide-dimethyl sulfide complex (8.02 mg, 0.039 mmol) in THF (0.75 ml) cooled to 0° C. After 30 minutes, 2 equivalents more of methylmagnesiumbromide was added. After 15 minutes, the reaction was quenched with saturated aqueous NH$_4$Cl solution. The product was extracted with ethyl acetate. The extracts were dried over Na$_2$SO$_4$, filtered and concentrated. The PMB-protected title compound was purified by silica gel chromatography (0-30% ethyl acetate in hexanes). The product-containing fractions were concentrated and treated with TFA (1 ml) in DCM (1 ml). After 10 min the volatiles were removed and the product was purified by reverse phase chromatography (Biotage 12g C-18 SNAP cartridge; 10-60% ACN in water+0.05% TFA). The product-containing fractions were concentrated and partioned between DCM and saturated NaHCO$_3$. The organic extract was dried over Na$_2$SO$_4$, filtered, and concentrated to provide the free base. $^1$H NMR (500 MHz, DMSO-d$_6$) δ: 12.82-12.30 (broad, 1H), 8.63 (d, J=5 Hz, 1H), 7.96 (s, 1H), 7.80 (dd, J=5 Hz, J=1.5 Hz, 1H), 7.65 (d, J=8 Hz, 2H), 7.58 (d, J=8 Hz, 2H), 6.93 (s, 1H), 7.51 (q, J=7 Hz, 1H), 2.37 (s, 3H), 1.68 (d, J=7.5 Hz, 3H). MS=360.1 (M+1).

Example 28

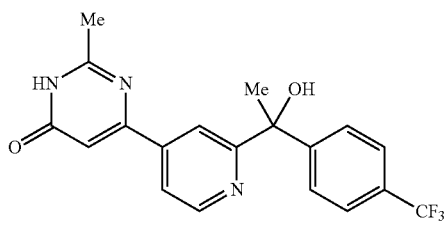 [SMILES: Cc1nc(-c2ccnc(C(C)(O)c3ccc(C(F)(F)F)cc3)c2)cc(=O)[nH]1]

6-(2-(1-hydroxy-1-(4-(trifluoromethyl)phenyl)ethyl)pyridin-4-yl)-2-methylpyrimidin-4(3H)-one, (Scheme 17)

Step 1. (4-Chloropyridin-2-yl)(4-(trifluoromethyl)phenyl)methanone n-Butyllithium (3.20 ml, 8.00 mmol) was added to −40° C. solution of 1-bromo-4-(trifluoromethyl)benzene (1800 mg, 8 mmol) in THF (30 ml) and this solution was stirred at −40° C. for 1 h. A solution of 4-chloropicolinaldehyde (1132 mg, 8.00 mmol) in THF (5 mL) was added and the solution was stirred at −40° C. for 1 h and then at 0° C. for 1 h. The reaction was quenched with saturated aqueous NH$_4$Cl solution. The product was extracted with ethyl acetate, the extract dried over Na$_2$SO$_4$, filtered, and concentrated. The crude material was dissolved in DCM (25 ml) and sodium bicarbonate (3360 mg, 40.0 mmol) was added. The solution was cooled to 0° C. and treated with Dess-Martin periodinane (3393 mg, 8.00 mmol). After 2 h of stirring at RT the byproducts were precipitated by the addition of 1:1 hexanes: ethyl acetate solution and removed by filtration. The eluent was concentrated and purified by silica gel chromatography (0-15% ethyl acetate in hexanes) to afford the title compound. LCMS=285.94 (M+1)

Step 2. (4-(6-((4-Methoxybenzyl)oxy)-2-methylpyrimidin-4-yl)pyridin-2-yl)(4-(trifluoromethyl)phenyl)-methanone (4-chloropyridin-2-yl)(4-(trifluoromethyl)phenyl)methanone (300 mg, 1.050 mmol), 4,4,4',4',5,5,5',5'-octamethyl-2,2'-bi(1,3,2-dioxaborolane) (267 mg, 1.050 mmol), potassium acetate (103 mg, 1.050 mmol), 2-dicyclohexylphosphino-2',6'-dimethoxybiphenyl (43.1 mg, 0.105 mmol), and Pd$_2$(dba)$_3$ (24.04 mg, 0.026 mmol) were combined in degassed dioxane (3 ml) and heated to 110° C. for 2.5 h. Potassium phosphate tribasic (1.050 ml, 5.25 mmol) and 4-chloro-6-((4-methoxybenzyl)oxy)-2-methylpyrimidine (232 mg, 0.875 mmol) were added and the reaction was heated at 110° C. for an additional 16 h. The reaction was cooled to RT, filtered through silica gel eluting with ethyl acetate, and concentrated. The crude material was then purified by silica gel chromatography (0-20% ethyl acetate in hexanes). LCMS=480.00 (M+1).

Step 3. 6-(2-(1-hydroxy-1-(4-(trifluoromethyl)phenyl)ethyl)pyridin-4-yl)-2-methylpyrimidin-4(3H)-one Methylmagnesium bromide (99 μl, 3.0 M in Et$_2$O, 0.298 mmol) was added to a 0° C. solution of (4-(6-((4-methoxybenzyl)oxy)-2-methylpyrimidin-4-yl)pyridin-2-yl)(4-(trifluoromethyl)phenyl)methanone (110 mg, 0.229 mmol) in THF (2 ml). The reaction was quenched with saturated aqueous NH$_4$Cl solution when it was judged to be complete by LCMS. The product was extracted with ethyl acetate and the extract was then dried over Na$_2$SO$_4$, filtered, and concentrated. The crude tertiary alcohol was dissolved in DCE (0.4 ml) and treated with TFA (400 μl, 5.19 mmol) and triethylsilane (400 μl, 2.504 mmol). No reduction was observed by LCMS after heating to 80° C. overnight. The reaction was concentrated and the tertiary alcohol was purified by reverse phase chromatography (Biotage 30g C-18 SNAP cartridge; 5-70% acetonitrile in water+0.05% TFA). The product-containing fractions were combined and concentrated. The compound was then freebased by partitioning between DCM and saturated aqueous NaHCO$_3$ solution. The organic extract was dried over Na$_2$SO$_4$, filtered, and concentrated. $^1$H NMR (500 MHz, CDCl$_3$) δ: 13.04-12.78 (broad, 1H), 8.70 (d, J=5.5 Hz, 1H), 7.92 (s, 1H), 7.80 (dd, J=5 Hz, J=1.5 Hz, 1H), 7.67 (d, J=8.5 Hz, 2H), 7.61 (d, J=8.5 Hz, 2H), 6.82 (s, 1H), 2.61 (s, 3H), 2.06 (s, 3H). MS=376.0 (M+1).

Example 29

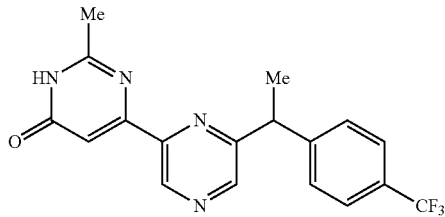

2-Methyl-6-(6-(1-(4-(trifluoromethyl)phenyl)ethyl)
pyrazin-2-yl)pyrimidin-4(3H)-one, (Scheme 18)

Step 1. 4-(6-Chloropyrazin-2-yl)-6-methoxy-2-methylpyrimidine

To a solution of 2,6-dichloropyrazine (0.312 g, 2.091 mmol) in 1,4-dioxane (10 mL) were added 4-methoxy-2-methyl-6-(trimethylstannyl)pyrimidine (0.300 g, 1.05 mmol) and tetrakis(triphenylphosphine)-palladium (0.121 g, 0.105 mmol) at RT. The reaction mixture was degassed with nitrogen 3 times. The mixture was stirred for 16 h at 100° C. under an atmosphere of nitrogen. The resulting mixture was cooled, and filtered. The filtrate was concentrated under reduced pressure. The residue was dissolved in ethyl acetate (50 mL). The organic layer was washed with brine (2×20 mL), dried with anhydrous sodium sulfate and filtered. The filtrate was concentrated under reduced pressure. The residue was purified by silica gel chromatography (3% ethyl acetate in petroleum ether) to furnish the title compound as a solid. $^1$H NMR (300 MHz, CDCl$_3$) δ: 9.55 (s, 1H), 8.67 (s, 1H), 7.51 (s, 1H), 4.03 (s, 3H), 2.71 (s, 3H).

Step 2. 4-Methoxy-2-methyl-6-(6-(1-(4-(trifluoromethyl)phenyl)vinyl)pyrazin-2-yl)pyrimidine The title compound was prepared using procedures similar to those described in step 3 of Example 22 using 4-(6-chloropyrazin-2-yl)-6-methoxy-2-methylpyrimidine to afford the title compound as a solid. MS=373.1 (+ESI).

Step 3. 4-Methoxy-2-methyl-6-(6-(1-(4-(trifluoromethyl)phenyl)ethyl)pyrazin-2-yl)pyrimidine The title compound was prepared using procedures similar to those described in step 4 of Example 22 using 4-methoxy-2-methyl-6-(6-(1-(4-(trifluoromethyl)phenyl)vinyl)pyrazin-2-yl)pyrimidine in methanol to afford the title compound as a solid and was used in the next step directly without further purification. MS=375.0 (+ESI).

Step 4. 2-Methyl-6-(6-(1-(4-(trifluoromethyl)phen)ethyl)pyrazin-2-yl)pyrimidin-4(3H)-one The title compound was prepared using procedures similar to those described in step 5 of Example 2 using 4-methoxy-2-methyl-6-(6-(1-(4-(trifluoromethyl)phenyl)ethyl)pyrazin-2-yl)pyrimidine to afford the title compound as a solid. $^1$H NMR (400 MHz, CDCl$_3$) δ: 13.32-13.20 (br, 1H), 9.43 (s, 1H), 9.56 (s, 1H), 7.61 (d, J=8.0 Hz, 2H), 7.55 (s, 1H), 7.51 (d, J=8.0 Hz, 2H), 4.46 (q, J=7.2 Hz, 1H), 2.66 (s, 3H), 1.83 (d, J=6.8 Hz, 3H). MS=361.1 (+ESI).

Examples 30 and 31

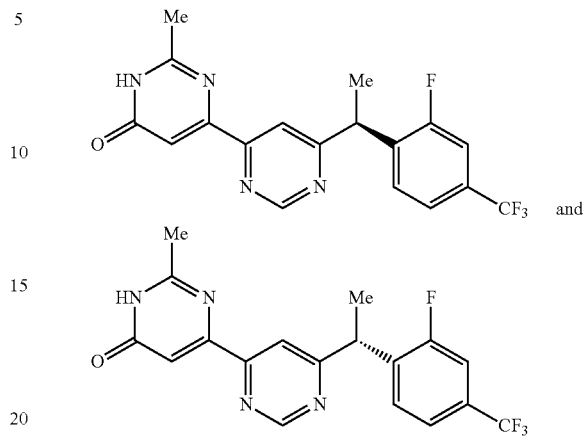

(R)- and (S)-6'-(1-(2-fluoro-4-(trifluoromethyl)phenyl)ethyl)-2-methyl-[4,4'-bipyrimidin]-6(1H)-one, (Scheme 19)

Step 1. 4-(2-fluoro-4-(trifluoromethyl)phenyl)pent-1-yn-3-ol n-Butyllithium (13.97 ml, 34.9 mmol) was added dropwise to a −78° C. slurry of (methoxymethyl)triphenylphosphonium chloride (12.86 g, 36.4 mmol) in THF (143 ml). The solution was stirred at −78° C. for 30 minutes and then at RT for 1 h. The mixture was recooled to −78° C. and 1-(2-fluoro-4-(trifluoromethyl)phenyl)ethanone (5 g, 24.26 mmol) was added as a solution in THF (19.02 ml). The mixture was allowed to warm to RT naturally overnight. The reaction was quenched with water (35 mL) and half of the THF was removed by evaporation under reduced pressure. The reaction was treated with HCl (35 mL) at 0° C. and then warmed to 55° C. for 24 h. The reaction was extracted with ether, and the combined organic layers were washed with water and saturated aqueous NaHCO$_3$. The solvent was removed at 100 torr to ~55 mL volume. The crude reaction mixture was cooled to 0° C. and treated with ethynylmagnesium bromide (97 ml, 48.5 mmol). The ice bath was removed and the reaction was stirred at RT for 30 minutes. The reaction was quenched with saturated aqueous NH$_4$Cl, extracted with ethyl acetate, dried over Na$_2$SO$_4$ and concentrated. The residue was then purified by silica gel chromatography (0-20% ethyl acetate in hexanes) to furnish the title compound as a liquid. $^1$H NMR (500 MHz, CDCl$_3$) δ: 7.54 (t, J=8 Hz, 1H), 7.40 (d, J=8 Hz, 1H), 7.31 (d, J=10 Hz, 1H), 4.59 (m, 1H), 3.49 (m, 1H), 1.44 (d, J=7.5 Hz, 3H).

Step 2. tert-butyl((4-(2-fluoro-4-(trifluoromethyl)phenyl)pent-1-yn-3-yl)oxy)dimethylsilane To a 0° C. solution of 4-(2-fluoro-4-(trifluoromethyl)phenyl)pent-1-yn-3-ol (626 mg, 2.54 mmol) and imidazole (346 mg, 5.09 mmol) in DMF (2543 µl) was added a solution of TBS-Cl (422 mg, 2.80 mmol) in DMF (0.6 mL). After 1 h, the reaction was warmed to RT and then stirred overnight. The reaction was diluted with ethyl acetate, washed with water and brine, dried over Na$_2$SO$_4$ and concentrated. The residue was then purified by silica gel chromatography (0-10% ethyl acetate in hexanes). ¹H NMR (500 MHz, CDCl₃) δ: 7.48 (t, J=8 Hz, 1H), 7.37 (d, J=8 Hz, 1H), 7.29 (d, J=10.5 Hz, 1H), 4.51 (m, 1H), 3.44 (m, 1H), 2.38 (s, 1H), 1.41 (d, J=7 Hz, 3H), 0.84-0.78 (m, 9H), 0.08 to −0.07 (m, 6H).

Step 3. 4-(3-((tert-butyldimethylsilyl)oxy)-4-(2-fluoro-4-(trifluoromethyl)phenyl)pent-1-yn-1-yl)-6-((4-methoxybenzyl)oxy)-2-methylpyrimidine tert-butyl((4-(2-fluoro-4-(trifluoromethyl)phenyl)pent-1-yn-3-yl)oxy)dimethylsilane (129 mg, 0.357 mmol), 4-chloro-6-((4-methoxybenzyl)oxy)-2-methylpyrimidine (86 mg, 0.325 mmol), cesium carbonate (318 mg, 0.975 mmol), and CataCXium A Palladium G3 (24.91 mg, 0.032 mmol) were combined in degassed toluene (1083 μl). The mixture was further degassed and heated to 90° C. overnight. The reaction was filtered through a pad of silica and washed with ethyl acetate. The eluent was concentrated and the crude material was used in the next step without further purification. MS=589.0 (M+1)

Step 4. 4-(2-fluoro-4-(trifluoromethyl)phenyl)-1-(6-((4-methoxybenzyl)oxy)-2-methylpyrimidin-4-yl)pent-1-yn-3-one To a RT solution of 4-(3-((tert-butyldimethylsilyl)oxy)-4-(2-fluoro-4-(trifluoromethyl)phenyl)pent-1-yn-1-yl)-6-((4-methoxybenzyl)oxy)-2-methylpyrimidine (940 mg, 1.597 mmol) in THF (16.0 mL) was added TBAF (1.92 mL, 1.916 mmol). After 2 h, the reaction was diluted with ethyl acetate, washed with saturated aqueous NaHCO₃, dried over Na₂SO₄ and concentrated. The residue was dissolved in DCM (6 mL) and cooled to 0° C. To the reaction vessel was added sodium bicarbonate (1342 mg, 15.97 mmol) followed by Dess-Martin periodinane (813 mg, 1.916 mmol). After 1 h, the reaction was filtered through a pad of silica eluting with EtOAc and the eluent was concentrated. The residue was purified by silica gel chromatography (0-30% ethyl acetate in hexanes) to furnish the title compound. MS=472.8 (M+1).

Step 5. 6-(1-(2-fluoro-4-(trifluoromethyl)phenyl)ethyl)-6'-((4-methoxybenzyl)oxy)-2'-methyl-2-(methylthio)-4,4'-bipyrimidine To a solution of 4-(2-fluoro-4-(trifluoromethyl)phenyl)-1-(6-((4-methoxybenzyl)oxy)-2-methylpyrimidin-4-yl)pent-1-yn-3-one (190 mg, 0.402 mmol) and sodium carbonate (63.9 mg, 0.603 mmol) in ethyl acetate (2346 μl) and water (335 μl) was added 2-methyl-2-thiopseudourea sulfate (168 mg, 0.603 mmol). This mixture was heated to 80° C. for 2 h. The reaction was cooled to RT, diluted with ethyl acetate, washed with saturated aqueous NaHCO₃, dried over Na₂SO₄ and concentrated. The residue was purified by silica gel chromatography (0-20% ethyl acetate in hexanes) to furnish the title compound. MS=544.9 (M+1).

Step 6. (R)- and (S)-6'-(1-(2-fluoro-4-(trifluoromethyl)phenyl)ethyl)-2-methyl-[4,4'-bipyrimidin]-6(1H)-one To a 0° C. mixture of 6-(1-(2-fluoro-4-(trifluoromethyl)phenyl)ethyl)-6'-((4-methoxybenzyl)oxy)-2'-methyl-2-(methylthio)-4,4'-bipyrimidine (70 mg, 0.129 mmol) and 10% Pd—C (13.68 mg, 0.013 mmol) in THF (300 μl) under nitrogen was added triethylsilane (0.062 mL, 0.386 mmol). After 18 h, an additional 9 equiv. of triethylsilane were added. After 2 h, an additional portion of 10% Pd/C (13.68 mg, 0.013 mmol) was added. After 2 h more, the reaction was filtered through Celite and eluting with ethyl acetate and the eluent was concentrated. The residue was dissolved in DCM (1 mL) and treated with trifluoroacetic acid (1 mL, 12.98 mmol) at RT. After 10 minutes, the reaction was concentrated, diluted with ethyl acetate, washed with saturated aqueous NaHCO₃, dried over Na₂SO₄ and concentrated. The residue was purified by silica gel chromatography (0-30% (3:1 ethyl acetate:ethanol) in hexanes) to furnish the racemic title compound. The racemic title compound was then resolved in the enantiomers by chiral SFC chromatography (Chiralpak IA; 20% methanol in CO₂+0.2% NH₄OH). The faster-eluting enantiomer of the title compound was obtained as a solid (Example 30). ¹H NMR (500 MHz, DMSO-d₆) δ: 12.72 (s, 1H), 9.19 (s, 1H), 8.15 (s, 1H), 7.69-7.59 (m, 3H), 7.11 (s, 1H), 4.74 (q, J=7 Hz, 1H), 2.38 (s, 3H), 1.68 (d, J=7.5 Hz, 3H). MS=378.78 (M+1). The slower-eluting enantiomer of the title compound was obtained as a solid (Example 31). ¹H NMR (500 MHz, DMSO-d₆) δ: 12.72 (s, 1H), 9.19 (s, 1H), 8.15 (s, 1H), 7.69-7.59 (m, 3H), 7.11 (s, 1H), 4.74 (q, J=7 Hz, 1H), 2.38 (s, 3H), 1.68 (d, J=7.5 Hz, 3H). MS=378.8 (M+1).

TABLE 2

The following compounds were prepared using procedures similar to those described for Examples 30 and 31 using the appropriate starting materials.

| Example No. | Structure | IUPAC Name | Exact Mass [M + H]⁺ | Chiral column |
|---|---|---|---|---|
| 32 | 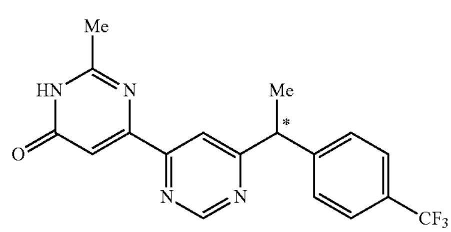 [SMILES: Cc1nc(-c2cc(C(C)c3ccc(C(F)(F)F)cc3)ncn2)cc(=O)[nH]1] | (R)- or (S)-2-methyl-6'-(1-(4-(trifluoromethyl)phenyl)ethyl)-[4,4'-bipyrimidin]-6(1H)-one | Calc'd 361.1, Found 361.3 | Chiralpak IA |

TABLE 2-continued

The following compounds were prepared using procedures similar to those described for Examples 30 and 31 using the appropriate starting materials.

| Example No. | Structure | IUPAC Name | Exact Mass [M + H]+ | Chiral column |
|---|---|---|---|---|
| 33 | 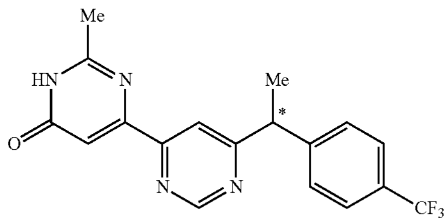 [SMILES: Cc1nc(-c2cc(C(C)c3ccc(C(F)(F)F)cc3)ncn2)cc(=O)[nH]1] | (S)- or (R)-2-methyl-6-(1-(1-(4-(trifluoromethyl)phenyl)ethyl)-1H-imidazol-4-yl)pyrimidin-4(3H)-one | Calc'd 361.1, Found 361.2 | Chiralpak IA |
| 34 | 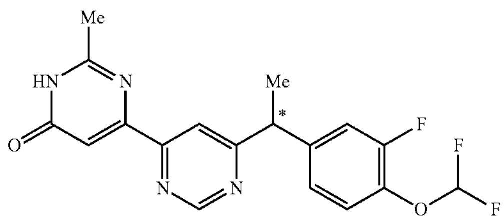 [SMILES: Cc1nc(-c2cc(C(C)c3ccc(OC(F)F)c(F)c3)ncn2)cc(=O)[nH]1] | (R)- or (S)-6'-(1-(4-(difluoromethoxy)-3-fluorophenyl)ethyl)-2-methyl-[4,4'-bipyrimidin]-6(1H)-one | Calc'd 377.1, found 377.0. | Chiralpak IC |
| 35 | 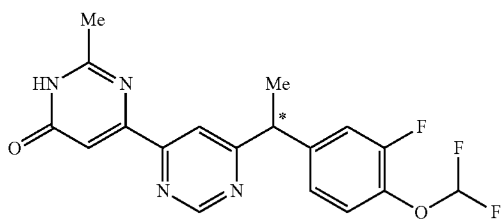 [SMILES: Cc1nc(-c2cc(C(C)c3ccc(OC(F)F)c(F)c3)ncn2)cc(=O)[nH]1] | (S)- or (R)-6'-(1-(4-(difluoromethoxy)-3-fluorophenyl)ethyl)-2-methyl-[4,4'-bipyrimidin]-6(1H)-one | Calc'd 377.1, found 377.0. | Chiralpak IC |
| 36 | 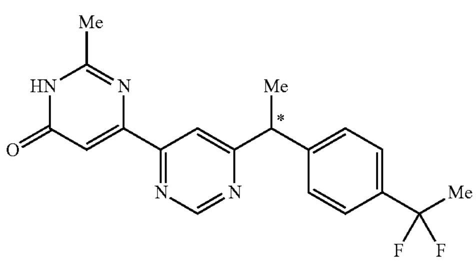 [SMILES: Cc1nc(-c2cc(C(C)c3ccc(C(C)(F)F)cc3)ncn2)cc(=O)[nH]1] | (R)- or (S)-6'-(1-(4-(1,1-difluoroethyl)phenyl)ethyl)-2-methyl-[4,4'-bipyrimidin]-6(1H)-one | Calc'd 357.1, found 357.1. | Chiralpak IC |
| 37 | 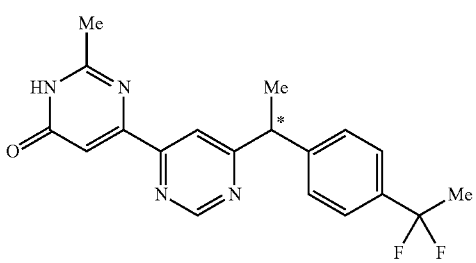 [SMILES: Cc1nc(-c2cc(C(C)c3ccc(C(C)(F)F)cc3)ncn2)cc(=O)[nH]1] | (S)- or (R)-6'-(1-(4-(1,1-difluoroethyl)phenyl)ethyl)-2-methyl-[4,4'-bipyrimidin]-6(1H)-one | Calc'd 357.1, found 357.1. | Chiralpak IC |
| 38 | 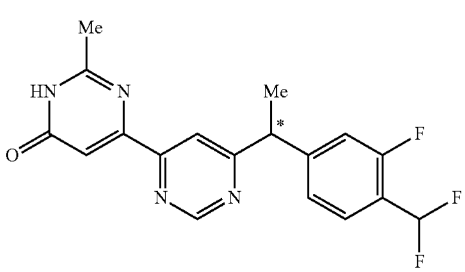 [SMILES: Cc1nc(-c2cc(C(C)c3ccc(C(F)F)c(F)c3)ncn2)cc(=O)[nH]1] | (R)- or (S)-6'-(1-(4-(difluoromethyl)-3-fluorophenyl)ethyl)-2-methyl-[4,4'-bipyrimidin]-6(1H)-one | Calc'd 361.1, found 361.2. | Chiralpak AD-H |

TABLE 2-continued

The following compounds were prepared using procedures similar to those described for Examples 30 and 31 using the appropriate starting materials.

| Example No. | Structure | IUPAC Name | Exact Mass [M + H]+ | Chiral column |
|---|---|---|---|---|
| 39 | 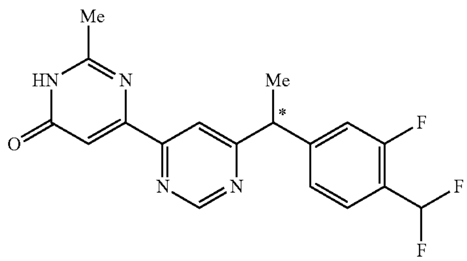 [SMILES: Cc1nc(-c2cc(C(C)c3ccc(C(F)F)c(F)c3)ncn2)cc(=O)[nH]1] | (S)- or (R)-6'-(1-(4-(difluoromethyl)-3-fluorophenyl)ethyl)-2-methyl-[4,4'-bipyrimidin]-6(1H)-one | Calc'd 361.1, found 361.2. | Chiralpak AD-H |
| 40 | 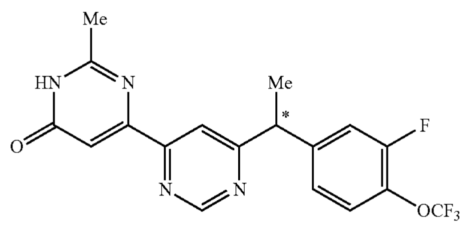 [SMILES: Cc1nc(-c2cc(C(C)c3ccc(OC(F)(F)F)c(F)c3)ncn2)cc(=O)[nH]1] | (R)- or (S)-6'-(1-(3-fluoro-4-(trifluoromethoxy)phenyl)ethyl)-2-methyl-[4,4'-bipyrimidin]-6(1H)-one | Calc'd 395.1, found 394.9. | Chiralpak IA |
| 41 | 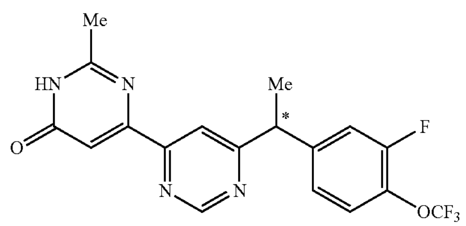 [SMILES: Cc1nc(-c2cc(C(C)c3ccc(OC(F)(F)F)c(F)c3)ncn2)cc(=O)[nH]1] | (S)- or (R)-6'-(1-(3-fluoro-4-(trifluoromethoxy)phenyl)ethyl)-2-methyl-[4,4'-bipyrimidin]-6(1H)-one | Calc'd 395.1, found 394.9. | Chiralpak IA |
| 42 | 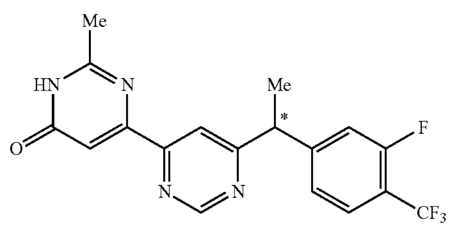 [SMILES: Cc1nc(-c2cc(C(C)c3ccc(C(F)(F)F)c(F)c3)ncn2)cc(=O)[nH]1] | (R)- or (S)-6'-(1-(3-fluoro-4-(trifluoromethoxy)phenyl)ethyl)-2-methyl-[4,4'-bipyrimidin]-6(1H)-one | Calc'd 379.1, found 379.0. | Chiralpak IA |
| 43 | 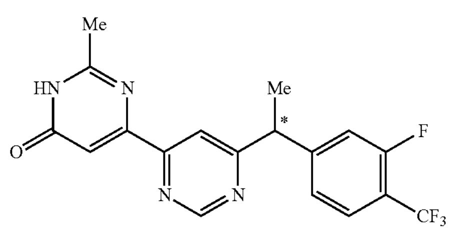 [SMILES: Cc1nc(-c2cc(C(C)c3ccc(C(F)(F)F)c(F)c3)ncn2)cc(=O)[nH]1] | (S)- or (R)-6'-(1-(3-fluoro-4-(trifluoromethoxy)phenyl)ethyl)-2-methyl-[4,4'-bipyrimidin]-6(1H)-one | Calc'd 379.1, found 379.0. | Chiralpak IA |
| 44 | 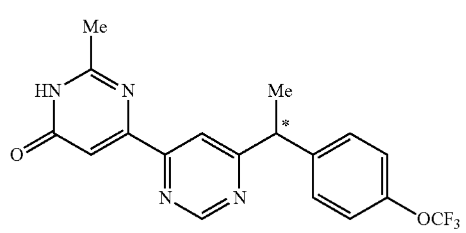 [SMILES: Cc1nc(-c2cc(C(C)c3ccc(OC(F)(F)F)cc3)ncn2)cc(=O)[nH]1] | (R)- or (S)-2-methyl-6'-(1-(4-(trifluoromethoxy)phenyl)ethyl)-[4,4'-bipyrimidin]-6(1H)-one | Calc'd 377.1, found 377.0. | Chiralpak IA |

TABLE 2-continued

The following compounds were prepared using procedures similar to those described for Examples 30 and 31 using the appropriate starting materials.

| Example No. | Structure | IUPAC Name | Exact Mass [M + H]⁺ | Chiral column |
|---|---|---|---|---|
| 45 | 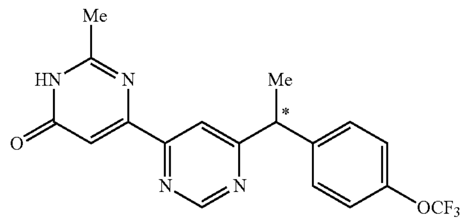 [SMILES: Cc1nc(-c2cc(C(C)c3ccc(OC(F)(F)F)cc3)ncn2)cc(=O)[nH]1] | (S)- or (R)-2-methyl-6'-(1-(4-(trifluoromethoxy)phenyl)ethyl)-[4,4'-bipyrimidin]-6(1H)-one | Calc'd 377.1, found 377.0. | Chiralpak IA |

Racemic products were separated using the chiral columns specified in the table.

Examples 46 and 47

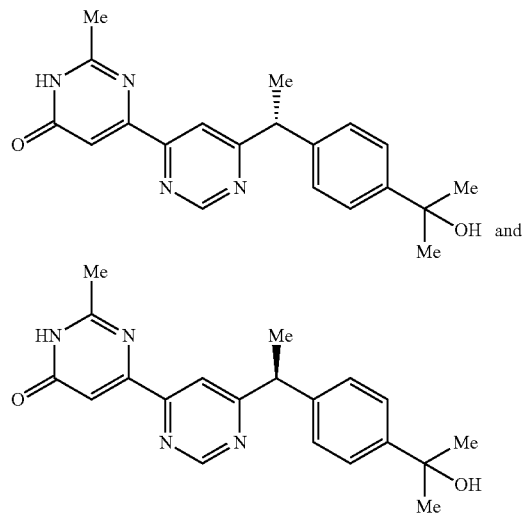

(R)- and (S)-6'-(1-(4-(2-hydroxypropan-2-yl)phenyl)ethyl)-2-methyl-[4,4'-bipyrimidin]-6(1H)-one, (Scheme 19)

Step 1. (Z)-methyl 4-(1-methoxyprop-1-en-2-yl)benzoate

To a stirred solution of chloro(methoxymethyl)triphenylphosphorane (14.4 g, 42.1 mmol) in THF (70 mL) was added n-butyllithium (2.5 M in hexane, 16.8 mL, 42.1 mmol) dropwise under an atmosphere of nitrogen at −78° C. The reaction solution was stirred at −78° C. for 30 minutes and then at RT for 1 h. The reaction mixture was cooled to −78° C. and a solution of methyl 4-acetylbenzoate (5.00 g, 28.1 mmol) in THF (30 mL) was added at −78° C. The reaction mixture was allowed to warm to RT and stirred for 16 h. The resulting mixture was quenched with water (15 mL). The mixture was extracted with ethyl acetate (3×100 mL). The combined organic layers were washed with saturated aqueous NaHCO₃ (30 mL) and dried over anhydrous Na₂SO₄. The filtrate was concentrated under reduced pressure. The residue was purified by silica gel chromatography (1-7% ethyl acetate in petroleum ether) to furnish the title compound as a liquid. MS (EI) m/z=206.0.

Step 2. Methyl 4-(1-oxopropan-2-yl)benzoate

To a stirred solution of (Z)-methyl 4-(1-methoxyprop-1-en-2-yl)benzoate (2.80 g, 13.6 mmol) in acetone (20 mL) and water (5 mL) was added hydrogen bromide (40% in water, 4.12 g, 20.4 mmol) at 0° C. The resulting mixture was stirred at 25° C. for 16 h. The reaction mixture was then quenched by saturated aqueous NaHCO₃ (25 mL) and extracted with ethyl acetate (3×50 mL). The combined organic layers were washed with brine (25 mL), dried over anhydrous Na₂SO₄ and filtered. The filtrate was concentrated under reduced pressure. The residue was purified by silica gel chromatography (1-12% of ethyl acetate in petroleum ether) to furnish the title compound as a liquid. MS (EI) m/z=192.0.

Step 3. Methyl 4-(3-hydroxypent-4-yn-2-yl)benzoate

The title compound was prepared using procedures similar to those described in step 1 of Examples 30 and 31 using methyl 4-(1-oxopropan-2-yl)benzoate (1.20 g, 6.24 mmol) and ethynylmagnesium bromide (0.5 M in THF, 12.5 mL, 6.24 mmol) in THF (20 mL) to afford the title compound as a liquid. ¹H NMR (300 MHz, DMSO-d₆) δ: 7.83 (d, J=8.1 Hz, 2H), 7.38 (d, J=8.1 Hz, 2H), 5.55-5.48 (m, 1H), 4.32-4.27 (m, 1H), 3.27 (s, 3H), 2.96-2.88 (m, 1H), 1.25 (d, J=7.1 Hz, 3H).

Step 4. Methyl 4-(3-((tert-butyldimethylsilyl)oxy)pent-4-yn-2-yl)benzoate

The title compound was prepared using procedures similar to those described in step 2 of Examples 30 and 31 using methyl 4-(3-hydroxypent-4-yn-2-yl)benzoate (1.00 g, 4.58 mmol), imidazole (0.624 g, 9.16 mmol) and tert-butylchlorodimethylsilane (1.38 g, 9.16 mmol) in DCM (20 mL) to afford the title compound as a liquid. ¹H NMR (400 MHz, CDCl₃) δ: 7.97 (d, J=8.0 Hz, 2H), 7.33 (d, J=8.0 Hz, 2H), 4.43-4.36 (m, 1H), 3.91 (s, 3H), 3.08-3.01 (m, 1H), 2.41-2.35 (m, 1H), 1.40 (d, J=8.0 Hz, 3H), 0.86 (s, 9H), 0.01 (s, 3H), −0.05 (s, 3H).

Step 5. 2-(4-(3-((tert-Butyldimethylsilyl)oxy)pent-4-yn-2-yl)phenyl)propan-2-ol To a stirred solution of methyl 4-(3-((tert-butyldimethylsilyl)oxy)pent-4-yn-2-yl)benzoate (1.30 g, 3.91 mmol) in THF (15 mL) was added and methylmagnesium bromide (3.0 M in THF, 13.0 mL, 39.1 mmol) as a solution in THF (15 mL) under an atmosphere of nitrogen at 0° C. The reaction mixture was stirred at 0° C. for 1 h and stirred at RT for additional 2 h. The resulting mixture was quenched with saturated aqueous NH$_4$Cl (20 mL) at 0° C. and extracted with ethyl acetate (3×20 mL). The combined organic layers were washed with brine (3×10 mL), dried with anhydrous Na$_2$SO$_4$ and filtered. The filtrate was concentrated under reduced pressure. The residue was purified by silica gel chromatography (10-20% of ethyl acetate in petroleum ether) to furnish the title compound as a liquid. $^1$H NMR (400 MHz, CDCl$_3$) δ: 7.40 (d, J=8.0 Hz, 2H), 7.23 (d, J=8.0 Hz, 2H), 4.40-4.31 (m, 1H), 3.02-2.94 (m, 1H), 2.41-2.35 (m, 1H), 1.57 (s, 6H), 1.39 (d, J=8.0 Hz, 3H), 0.87 (s, 9H), 0.01 (s, 3H), −0.06 (s, 3H).

Step 6. 2-(4-(3-((tert-Butyldimethylsilyl)oxy)-5-(6-((4-methoxybenzyl)oxy)-2-methylpyrimidin-4-yl)pent-4-yn-2-yl)phenyl)propan-2-ol The title compound was prepared using procedures similar to those described in step 3 of Examples 30 and 31 using 2-(4-(3-((tert-butyldimethylsilyl)oxy)pent-4-yn-2-yl)phenyl)propan-2-ol (1.30 g, 3.91 mmol), 4-chloro-6-((4-methoxybenzyl)oxy)-2-methylpyrimidine (1.04 g, 3.91 mmol), bis(triphenylphosphine)-palladium(II) dichloride (0.549 g, 0.782 mmol) and cesium carbonate (3.82 g, 11.7 mmol) in toluene (10 mL) to afford the title compound as a liquid. MS (+ESI) m/z=561.2

Step 7. 4-(4-(2-Hydroxypropan-2-yl)phenyl)-1-(6-((4-methoxybenzyl)oxy)-2-methylpyrimidin-4-yl)pent-1-yn-3-ol The title compound was prepared using procedures similar to those described in step 4 of Examples 30 and 31 using 2-(4-(3-((tert-butyldimethyl-silyl)oxy)-5-(6-((4-methoxybenzyl)oxy)-2-methylpyrimidin-4-yl)pent-4-yn-2-yl)phenyl)propan-2-ol (1.30 g, 2.32 mmol) and tetrabutylammonium fluoride (1 M in THF, 2.8 mL, 2.78 mmol) in THF (15 mL) followed by (1,1,1-triacetoxy)-1,1-dihydro-1,2-benziodoxol-3(1H)-one (1.00 g, 2.37 mmol) in DCM (10 mL) to afford the title compound as a liquid. MS (+ESI) m/z=445.0.

Step 8. 2-(4-(1-(6'-((4-Methoxybenzyl)oxy)-2'-methyl-2-(methylthio)-[4,4'-bipyrimidin]-6-yl)ethyl)phenyl)propan-2-ol The title compound was prepared using procedures similar to those described in step 5 of Examples 30 and 31 using 4-(4-(2-hydroxypropan-2-yl)phenyl)-1-(6-((4-methoxybenzyl)oxy)-2-methylpyrimidin-4-yl)pent-1-yn-3-one (0.650 g, 1.46 mmol), methyl carbamimidothioate hemisulfate (0.413 g, 2.19 mmol) and sodium carbonate (0.232 g, 2.19 mmol) in ethyl acetate (5 mL) and water (0.7 mL) to afford the title compound as a liquid. MS (+ESI) m/z=517.1.

Step 9. 2-(4-(1-(6'-((4-Methoxybenzyl)oxy)-2'-methyl-[4,4'-bipyrimidin]-6-yl)ethyl)phenyl)propan-2-ol To a 0° C. mixture of using 2-(4-(1-(6'-((4-methoxybenzyl)oxy)-2'-methyl-2-(methylthio)-[4,4'-bipyrimidin]-6-yl)ethyl)phenyl)propan-2-ol (0.650 g, 1.26 mmol) and palladium 10% on carbon (0.134 g, 0.126 mmol) in THF (6 mL) under nitrogen was added triethylsilane (1.0 mL, 6.29 mmol). After 20 h the reaction mixture was filtered through Celite and the filter cake was washed with ethyl acetate to furnish the title compound. MS (+ESI) m/z=471.0.

Step 10. (R)- and (S)-6'-(1-(4-(2-hydroxypropan-2-yl)phenyl)ethyl)-2-methyl-[4,4'-bipyrimidin]-6(1H)-one To a stirred solution of 2-(4-(1-(6'-((4-methoxybenzyl)oxy)-2'-methyl-[4,4'-bipyrimidin]-6-yl)ethyl)phenyl)propan-2-ol (0.100 g, 0.213 mmol) in DCM (2 mL) and water (0.4 mL) was added 2,3-dichloro-5,6-dicyano-1,4-benzoquinone (72.4 mg, 0.319 mmol) at RT. The solution was stirred at RT for 3 h. The resulting solution was extracted with DCM (3×5 mL). The combined organic fractions were washed with brine (4 mL), dried over anhydrous Na$_2$SO$_4$ and filtered. The filtrate was concentrated under reduced pressure and the residue was purified by preparative HPLC (X Bridge C-18 OBD Prep Column (20% to 50% acetonitrile in water (10 mmol/L NH$_4$HCO$_3$)) to furnish the title compound as a solid. MS (+ESI) m/z=351.1. Racemic 6'-(1-(4-(2-hydroxypropan-2-yl)phenyl)ethyl)-2-methyl-[4,4'-bipyrimidin]-6(1H)-one was separated into the enantiomers by chiral preparative HPLC (Chiralpak IA column; 30% ethanol in hexane). The faster-eluting enantiomer of the title compound (Example 46) was obtained at as a solid. $^1$H NMR (400 MHz, CD$_3$OD) δ: 9.13 (s, 1H), 8.17 (s, 1H), 7.43 (d, J=8.4 Hz, 2H), 7.32 (s, 1H), 7.28 (d, J=8.0 Hz, 2H), 4.35 (q, J=7.1 Hz, 1H), 2.46 (s, 3H), 1.72 (d, J=7.2 Hz, 3H), 1.50 (s, 6H). MS (+ESI) m/z=351.1. The slower-eluting enantiomer of the title compound (Example 47) was obtained as a solid.

$^1$H NMR (400 MHz, CD$_3$OD) δ: 9.13 (s, 1H), 8.17 (s, 1H), 7.43 (d, J=8.4 Hz, 2H), 7.32 (s, 1H), 7.28 (d, J=8.4 Hz, 2H), 4.35 (q, J=7.2 Hz, 1H), 2.46 (s, 3H), 1.72 (d, J=7.2 Hz, 3H), 1.50 (s, 6H). MS (+ESI) m/z=351.2.

Example 48

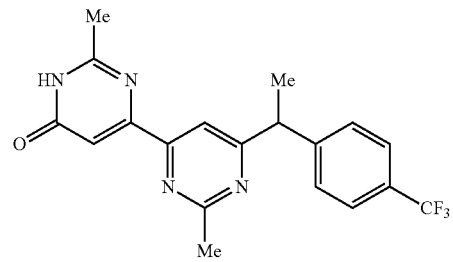 [SMILES: Cc1nc(-c2cc(=O)[nH]c(C)n2)cc(C(C)c2ccc(C(F)(F)F)cc2)n1]

2,2'-dimethyl-6'-(1-(4-(trifluoromethyl)phenyl)ethyl)-[4,4'-bipyrimidin]-6(1H)-one. (Scheme 19)

1-(6-((4-methoxybenzyl)oxy)-2-methylpyrimidin-4-yl)-4-(4-(trifluoromethyl)phenyl)-pent-1-yn-3-one (52 mg, 0.114 mmol), acetimidamide hydrochloride (21.64 mg, 0.229 mmol), and sodium carbonate (24.26 mg, 0.229 mmol) were combined in ethyl acetate (0.7 ml) and water (0.1 ml) and heated to 80° C. for 5 h. The mixture was partioned between ethyl acetate and saturated aqueous NaHCO$_3$. The organic extract was dried over Na$_2$SO$_4$, filtered, and concentrated. The crude material was dissolved in DCM (1 ml) and treated with TFA (1 ml, 12.98 mmol). The deprotection was complete within minutes. The solvent was removed and the compound was purified by reverse phase chromatography (Biotage 30g C-18 SNAP cartridge; 10-55% acetonitrile in water+0.05% TFA). The product containing fractions were concentrated and the residue was partioned between DCM and saturated NaHCO$_3$. The organic extract was dried over Na$_2$SO$_4$, filtered, and concentrated to yield the free-based compound. $^1$H NMR (500 MHz, DMSO-d$_6$) δ: 12.74-12.62 (broad, 1H), 7.92 (s, 1H), 7.67 (d, J=8.5 Hz, 2H), 7.57 (d, J=8.5 Hz, 2H), 7.09 (s, 1H), 4.51 (q, J=7 Hz, 1H), 3.31 (s, 3H), 2.63 (s, 3H), 1.64 (d, J=7 Hz, 3H). MS=375.1 (M+1).

Assay

The activity of the compounds in accordance with the present invention as PDE2 inhibitors may be readily determined using a fluorescence polarization (FP) methodology (Huang, W., et al., J. Biomol Screen, 2002, 7: 215). In particular, the compounds of the following examples had activity in reference assays by exhibiting the ability to inhibit the hydrolysis of the phosphate ester bond of a cyclic nucleotide. Any compound exhibiting a Ki (inhibitory constant) of about 50 μM or below would be considered a PDE2 inhibitor as defined herein.

In a typical experiment the PDE2 inhibitory activity of the compounds of the present invention was determined in accordance with the following experimental method. Rhesus PDE2A3 was amplified from rhesus macaque brain cDNA (Biochain Institute, Hayward, Calif.) using primers based on human PDE2A sequence (accession NM_002599.3) where the forward primer containing a Kozak consensus was 5'-gccaccatggggcaggcatgtggc-3' and the reverse primer was 5'-tcactcagcatcaaggctgca-3'. Amplification with Easy-A High-Fidelity PCR cloning enzyme (Stratagene, La Jolla, Calif.) was 95° C. for 2 minutes followed by thirty three cycles of 95° C. for 40 seconds, 52° C. for 30 seconds, and 72° C. for 2 minutes 48 seconds. Final extension was 72° C. for 7 minutes. The PCR product was TA cloned into pcDNA3.3-TOPO (Invitrogen, Carlsbad, Calif.) according to standard protocol. A consensus sequence was developed from multiple clones and then deposited into GenBank (EU812167). AD293 cells (Stratagene, La Jolla, Calif.) with 70-80% confluency were transiently transfected with rhesus PDE2A3/pcDNA3.3-TOPO using Lipofectamine 2000 according to manufacturer specifications (Invitrogen, Carlsbad, Calif.). Cells were harvested 48 hours post-transfection and lysed by sonication (setting 3, 10×5 sec pulses) in a buffer containing 20 mM HEPES pH 7.4, 1 mM EDTA and Complete Protease Inhibitor Cocktail Tablets (Roche, Indianapolis, Ind.). Lysate was collected by centrifugation at 75,000×g for 20 minutes at 4° C. and supernatant utilized for evaluation of PDE2 activity. The fluorescence polarization assay for cyclic nucleotide phosphodiesterases was performed using an IMAP® FP kit supplied by Molecular Devices, Sunnyvale, Calif. (product # R8139). IMAP® technology has been applied previously to examine the effects of phosphodiesterase inhibitors (Huang, W., et al., J. Biomol Screen, 2002, 7: 215). Assays were performed at room temperature in 384-well microtiter plates with an incubation volume of 20.2 μL. Solutions of test compounds were prepared in DMSO and serially diluted with DMSO to yield 8 μL of each of 10 solutions differing by 3-fold in concentration, at 32 serial dilutions per plate. 100% inhibition is determined using a known PDE2 inhibitor, which can be any compound that is present at 5,000 times its Ki value in the assay described below, such as Bay 60-7550 (Ki-~0.2 nM) at 1 μM concentration for 100% inhibition. Bay 60-7550 was obtained from Axxora via Fisher Scientific (cat#ALX-270-421-M025/cat#NC9314773). Put another way, any compound with Ki of ~0.2 to about 2 nM could be used at 1 to 10 μM. 0% of inhibition is determined by using DMSO (1% final concentrations).

A Labcyte Echo 555 (Labcyte, Sunnyvale, Calif.) is used to dispense 200 nL from each well of the titration plate to the 384 well assay plate. Ten microliters of a solution of enzyme (1/2000 final dilution from aliquots; sufficient to produce 20% substrate conversion) was added to the assay plate. Next 10 uL of a separate solution of the substrate FAM-labeled cAMP (50 nM final concentration product # R7506 from Molecular Devices) and the activator cGMP (1 uM final concentration), prepared in the assay buffer (10 mM Tris HCl, pH 7.2, 10 mM MgCl$_2$, 0.05% NaN$_3$ 0.01% Tween-20, and 1 mM DTT) was added to the assay plate and shaken to mix. The reaction is allowed to proceed at room temperature for 60 minutes. A binding solution is then made from the kit components, comprised of 80% Solution A, 20% Solution B and binding reagent at a volume of 1/600 the total binding solution. The enzymatic reaction is stopped by addition of 60 μL of the binding solution to each well of the assay plates and the plates are sealed and shaken for 30 seconds. The plate was incubated at room temperature for at least one hour prior to determining the fluorescence polarization (FP). The parallel and perpendicular fluorescence of each well of the plate was measured using a Tecan Genios Pro plate reader (Tecan, Switzerland) or Perkin Elmer EnVision™ plate reader (Waltham, Mass.). Fluorescence polarization (mP) was calculated from the parallel (S) and perpendicular (P) fluorescence of each sample well and the analogous values for the median control well, containing only substrate (So and Po), using the following equation:

Polarization (mP)=1000*(S/So−P/Po)/(S/So+P/Po).

Dose-inhibition profiles for each compound were characterized by fitting the mP data to a four-parameter equation given below. The apparent inhibition constant (KI), the maximum inhibition at the low plateau relative to "100% Inhibition Control" (Imax; e.g. 1=>same as this control), the minimum inhibition at the high plateau relative to the "0% Inhibition Control" (Imin, e.g. 0=>same as the no drug control) and the Hill slope (nH) are determined by a non-linear least squares fitting of the mP values as a function of dose of the compound using an in-house software based on the procedures described by Mosser et al., JALA, 2003, 8: 54-63, using the following equation:

$$mP = \frac{(0\% \ mP - 100\% \ mP)(Imax - Imin)}{1 + \left[\frac{[Drug]}{\left(10^{-pK_1}\left(1 + \frac{[Substrate]}{K_M}\right)\right)}\right]^{nH}} +$$

$$100\% \ mP + (0\% \ mP - 100\% \ mP)(1 - Imax)$$

The median signal of the "0% inhibition controls" (0% mP) and the median signal of the "100% inhibition controls" (100% mP) are constants determined from the controls located in columns 1-2 and 23-24 of each assay plate. An apparent (K$_M$) for FAM-labeled cAMP of ~10 uM was used.

Selectivity for PDE2, as compared to other PDE families, was assessed using the IMAPR technology. Human PDE10A2 enzyme was prepared from cytosolic fractions of transiently transfected HEK cells. All other PDE's were GST Tag human enzyme expressed in insect cells and were obtained from BPS Bioscience (San Diego, Calif.): PDE1A (Cat#60010), human PDE2A1(Cat#60020), PDE3A (Cat#60030), PDE4A1A (Cat#60040), PDE5A1

(Cat#60050), PDE6C (Cat#60060), PDE7A (Cat#60070), PDE8A1 (Cat#60080), PDE9A2 (Cat#60090), PDE11A4 (Cat#60110).

Assays for PDE 1 through 11 were performed in parallel at room temperature in 384-well microtiter plates with an incubation volume of 20.2 µL. Solutions of test compounds were prepared in DMSO and serially diluted with DMSO to yield 30 µL of each of ten solutions differing by 3-fold in concentration, at 32 serial dilutions per plate. 100% inhibition was determined by adding buffer in place of the enzyme and 0% inhibition is determined by using DMSO (1% final concentrations). A Labcyte POD 810 (Labcyte, Sunnyvale, Calif.) was used to dispense 200 nL from each well of the titration plate to make eleven copies of the assay plate for each titration, one copy for each PDE enzyme. A solution of each enzyme (dilution from aliquots, sufficient to produce 20% substrate conversion) and a separate solution of FAM-labeled cAMP or FAM-labeled cGMP from Molecular Devices (Sunnyvale, Calif., product # R7506 or cGMP#R7508), at a final concentration of 50 nM were made in the assay buffer (10 mM Tris HCl, pH 7.2, 10 mM MgCl$_2$, 0.05% NaN$_3$ 0.01% Tween-20, and 1 mM DTT). Note that the substrate for PDE2 is 50 nM FAM cAMP containing 1000 nM of cGMP. The enzyme and the substrate were then added to the assay plates in two consecutive additions of 10 µL and then shaken to mix. The reaction was allowed to proceed at room temperature for 60 minutes. A binding solution was then made from the kit components, comprised of 80% Solution A, 20% Solution B and binding reagent at a volume of 1/600 the total binding solution. The enzymatic reaction was stopped by addition of 60 µL of the binding solution to each well of the assay plate. The plates were sealed and shaken for 10 seconds. The plates were incubated at room temperature for one hour, then the parallel and perpendicular fluorescence was measured using a Tecan Genios Pro plate reader (Tecan, Switzerland). The apparent inhibition constants for the compounds against all 11 PDE's was determined from the parallel and perpendicular fluorescent readings as described for PDE10 FP assay using the following apparent K$_M$ values for each enzyme and substrate combination: PDE1A (FAM cGMP) 70 nM, human PDE2A1 (FAM cAMP) 10,000 nM, PDE3A (FAM cAMP) 50 nM, PDE4A1A (FAM cAMP) 1500 nM, PDE5A1 (FAM cGMP) 400 nM, PDE6C (FAM cGMP) 700 nM, PDE7A (FAM cAMP) 150 nM, PDE8A1 (FAM cAMP) 50 nM, PDE9A2 (FAM cGMP) 60 nM, PDE1A2 (FAM cAMP) 150 nM, PDE11A4 (FAM cAMP) 1000 nM. The intrinsic PDE2 inhibitory activity of a compound which may be used in accordance with the present invention may be determined by these assays.

The compounds of the following examples had activity in inhibiting the human PDE2 enzyme in the aforementioned assays with a Ki of less than about 50 µM. Many of compounds within the present invention had activity in inhibiting the human PDE2 enzyme in the aforementioned assays, with a Ki of less than about 1 µM, preferably less than or about 0.1 µM. Additional data is provided in the following Examples. Such a result is indicative of the intrinsic activity of the compounds in use as inhibitors of the PDE2 enzyme. In general, one of ordinary skill in the art would appreciate that a substance is considered to effectively inhibit PDE2 activity if it has a Ki of less than or about 1 µM, preferably less than or about 0.1 µM. The present invention also includes compounds within the generic scope of the invention which possess activity as inhibitors of other phosphodiesterase enzymes.

In the following tables representative data for the compounds of formula I as PDE2 inhibitors as determined by the foregoing assays. The PDE2 Ki is a measure of the ability of the test compound to inhibit the action of the PDE2 enzyme.

TABLE 3

| | PDE2 Ki Values | | | |
|---|---|---|---|---|
| Example | hPDE2 Ki (nM) LabA | rhPDE2 Ki (nM) LabA | hPDE2 Ki (nM) LabB | rhPDE2 Ki (nM) LabB |
| 1 | 60 | 96 | NA | 481 |
| 2 | NA | 1235 | NA | NA |
| 3 | NA | 532 | NA | NA |
| 4 | NA | NA | 22 | 20 |
| 5 | NA | NA | 18 | 19 |
| 6 | 6 | 10 | 12 | 13 |
| 7 | 13 | 21 | 62 | 57 |
| 8 | 403 | 352 | NA | NA |
| 9 | 79 | 86 | NA | 159 |
| 10 | NA | 470 | NA | 699 |
| 11 | NA | 1081 | NA | 1751 |
| 12 | NA | 1870 | NA | 2410 |
| 13 | NA | 868 | NA | 631 |
| 14 | NA | 298 | NA | NA |
| 15 | 21 | 24 | 45 | 46 |
| 16 | NA | 340 | NA | NA |
| 17 | 76 | 106 | NA | NA |
| 18 | 1.4 | 2.3 | NA | NA |
| 19 | NA | 0.2 | 0.4 | 0.4 |
| 20 | NA | NA | NA | 123 |
| 21 | NA | NA | NA | 110 |
| 22 | NA | 920 | NA | 868 |
| 23 | NA | >1000 | NA | NA |
| 24 | NA | 826 | NA | NA |
| 25 | NA | 12900 | NA | NA |
| 26 | NA | 1806 | NA | NA |
| 27 | NA | 1267 | NA | NA |
| 28 | NA | 2878 | NA | NA |
| 29 | NA | 1711 | NA | 1661 |
| 30 | NA | NA | 39 | NA |
| 31 | NA | NA | 16 | NA |
| 32 | NA | NA | 64 | NA |
| 33 | NA | NA | 20 | NA |
| 34 | NA | NA | 13 | NA |
| 35 | NA | NA | 232 | NA |
| 36 | NA | NA | 20 | NA |
| 37 | NA | NA | 65 | NA |
| 38 | NA | NA | 30 | NA |
| 39 | NA | NA | 174 | NA |
| 40 | NA | NA | 1.8 | NA |
| 41 | NA | NA | 212 | NA |
| 42 | NA | NA | 7.5 | NA |
| 43 | NA | NA | 45 | NA |
| 44 | NA | NA | 4.1 | NA |
| 45 | NA | NA | 194 | NA |
| 46 | NA | NA | 890 | NA |
| 47 | NA | NA | 1716 | NA |
| 48 | 312 | 516 | NA | NA |

(NA = Not available)

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of structural formula I:

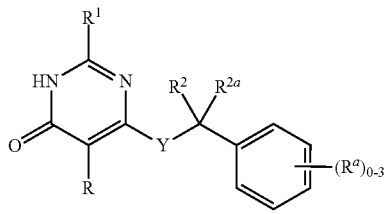

I or a pharmaceutically acceptable salt thereof, wherein:
$R^1$ is selected from the group consisting of hydrogen, $C_{1-6}$alkyl, $C_{3-10}$cycloalkyl, and $(CH_2)_nC_{6-10}$aryl, said alkyl, cycloalkyl, and aryl optionally substituted with one to three groups of $R^a$;
$R^2$ and $R^{2a}$ are independently selected from the group consisting of hydrogen, $C_{1-6}$alkyl, $C_{2-6}$alkenyl, $(CH_2)nOR$, $C(O)OR$, $N(R)_2$, $C_{3-10}$ cycloalkyl, $(CH_2)_nC_{5-10}$ heterocyclyl said alkyl, cycloalkyl, and heterocyclyl optionally substituted with one to three groups of $R^b$;
$R^2$ and $R^{2a}$ can combine with the carbon atom to which they are attached to form a $C_{2-6}$ alkenyl, $C_{3-6}$ cycloalkyl, or $C_{4-10}$ heterocyclyl, said alkenyl, cycloalkyl and heterocyclyl optionally substituted with one to three groups of $R^b$;
Y is selected from the group consisting of pyridyl, pyrimidinyl, pyrazinyl, pyridazinyl, oxazolyl, oxadiazolyl, thiazolyl, thiadiazolyl, and imidazolyl, said group optionally substituted with one to three groups of $R^b$;
R represents H, or $C_{1-6}$ alkyl,
$R^a$ is selected from the group consisting of halo, CN, $C_{1-6}$alkyl, $(CH_2)_nOR$, $(O)_pC_{1-4}$haloalkyl, $C(O)OR$, $-O(CH_2)_nN(R)_2$, $(CHR)_nN(R)_2$, $NO_2$, $SCF_3$, $S(O)_sCF_3$, $S(O)_sR$, $SF_5$, $C_{3-10}$ cycloalkyl, $O-C_{3-10}$ cycloalkyl, $C_{5-10}$heterocyclyl, and $C_{6-10}$aryl, said alkyl, cycloalkyl, heterocyclyl and aryl optionally substituted with one to three groups of $R^b$;
$R^b$ is selected from the group consisting of halo, $C_{1-6}$alkyl, $(CH_2)_nOR$, and $(O)_pC_{1-4}$haloalkyl;
n represents 0, 1, 2, 3, or 4;
s represents 0, 1, or 2; and
p represents 0 or 1.

2. The compound according to claim 1 or a pharmaceutically acceptable salt thereof, wherein Y is optionally substituted pyridyl, pyrimidinyl, pyrazinyl, or pyridazinyl represented by structural formulas (a), (b), (c), (d), (e), (f), (g), (h), (i) and (j):

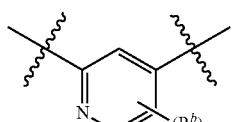
(a)

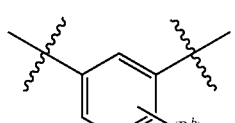
(b)

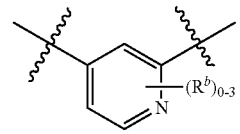
(c)

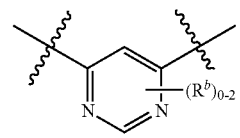
(d)

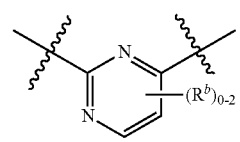
(e)

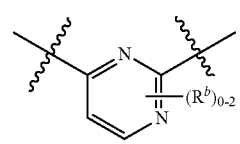
(f)

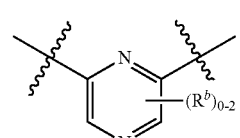
(g)

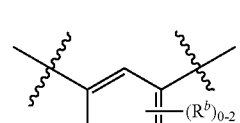
(h)

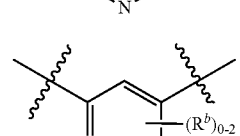
(i)

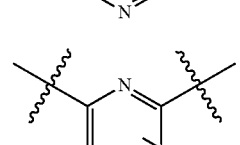
(j)

3. The compound according to claim 2, or a pharmaceutically acceptable salt thereof, wherein Y is optionally substituted pyridyl represented by structural formula (a), (b), (c) or (j).

4. The compound according to claim 2, or a pharmaceutically acceptable salt thereof, wherein Y is optionally substituted pyrimidinyl represented by structural formula (d), (e), or (f).

5. The compound according to claim 2, or a pharmaceutically acceptable salt thereof, wherein Y is optionally substituted pyrazinyl represented by structural formula (g).

6. The compound according to claim 2, or a pharmaceutically acceptable salt thereof, wherein Y is optionally substituted pyridazinyl represented by structural formula (h) or (i).

7. The compound according to claim 1 or a pharmaceutically acceptable salt thereof wherein Y is optionally substituted oxazolyl, oxadiazolyl, thiazolyl, thiadiazolyl, or imidazolyl represented by structural formulas (k), (l), (m), (n), (o), (p), (q), (r), (s), (t), (u), (v), and (w):

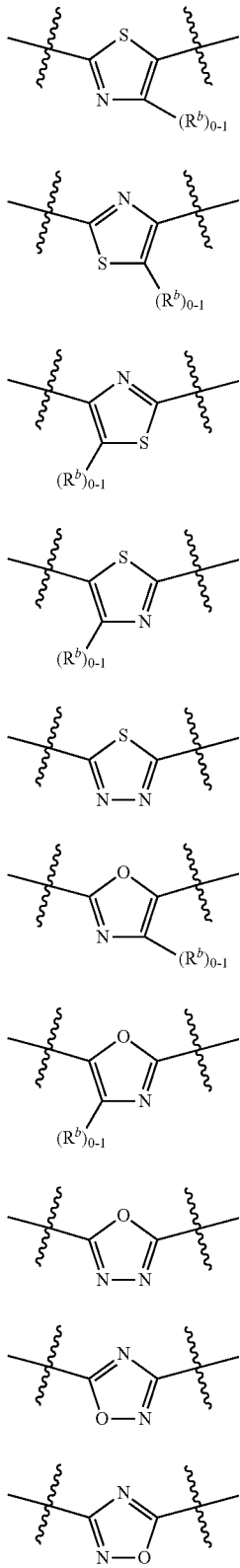

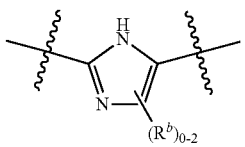

(u)

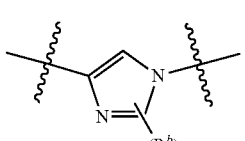

(v)

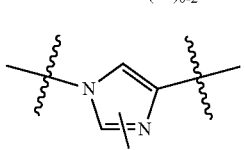

(w)

8. The compound according to claim 7, or a pharmaceutically acceptable salt thereof wherein Y is optionally substituted thiazolyl represented by structural formula (k), (l), (m), or (n).

9. The compound according to claim 7, or a pharmaceutically acceptable salt thereof, wherein Y is thiadiazolyl represented by structural formula (o).

10. The compound according to claim 7, or a pharmaceutically acceptable salt thereof, wherein Y is optionally substituted oxazolyl represented by structural formula (p) or (q).

11. The compound according to claim 7, or a pharmaceutically acceptable salt thereof, wherein Y is oxadiazolyl represented by structural formula (r), (s) or (t).

12. The compound according to claim 7, or a pharmaceutically acceptable salt thereof, wherein Y is optionally substituted imidazolyl represented by structural formula (u), (v) or (w).

13. The compound according to claim 1, or a pharmaceutically acceptable salt thereof wherein R is hydrogen, $R^1$ is $C_{1-6}$ alkyl optionally substituted with 1 to 3 groups of $R^a$, $R^2$ and $R^{2a}$ are independently selected from hydrogen, $(CH_2)_nCH_3$, $CH_3$, $CH(CH3)_2$, $(CH_2)_nOH$, $C(O)OCH_3$, $NHCH_3$, $(CH_2)_n(OCH_3)$, cyclopropyl, cyclobutyl, tetrahydrofuranyl, and $R^a$ is selected from OH, halo, $(CH_2)_nCH_3$, $CH(CH_3)_2$, $C(CH_3)_3$, $(CH_2)_nOCH_3$, $OC(CH_3)_2$, $CH_2F$, $CHF_2$, $CF_3$, $OCHF_2$, $OCF_3$, $SCH_3$, $SCF_3$, $SF_5$, $SOCF_3$, $SO_2CF_3$, $SO_2CH_3$, $CH_2NH_2$, $(CH_2)_nN(CH_3)_2$, $NO_2$, CN, cyclobutyl, cyclopropyl, and phenyl, said groups, optionally substituted with one to three groups of Rb.

14. The compound according to claim 1, or a pharmaceutically acceptable salt thereof wherein one of $R^2$ and $R^{2a}$ is hydrogen and the other is selected from the group consisting of $(CH_2)_nCH_3$, $CH_3$, $CH(CH3)_2$, $(CH_2)_nOH$, $C(O)OCH_3$, $NHCH_3$, $(CH_2)_n(OCH_3)$, cyclopropyl, cyclobutyl, and tetrahydrofuranyl.

15. The compound according to claim 1, or a pharmaceutically acceptable salt thereof wherein the number of $R^b$ present is zero, $R^1$ is optionally substituted methyl optionally substituted with 1 to 3 groups of $R^a$, and one of $R^2$ and $R^{2a}$ is hydrogen and the other is $(CH_2)_nCH_3$.

16. The compound according to claim 1, or a pharmaceutically acceptable salt thereof wherein Y is pyridyl, pyrimidinyl, pyrazinyl, pyridazinyl, oxazolyl, oxadiazolyl, thiazolyl, thiadiazolyl, or imidazolyl, said groups optionally substituted with 1 to 3 groups of $R^a$, R is hydrogen, $R^1$ is methyl optionally substituted with 1 to 3 groups of $R^a$, and one of $R^2$ and $R^{2a}$ is hydrogen and the other is selected from $(CH_2)_nCH_3$, $CH_3$, $CH(CH_3)_2$, $(CH_2)_nOH$, $C(O)OCH_3$, $NHCH_3$, $(CH_2)_n(OCH_3)$, cyclopropyl, cyclobutyl, and tetrahydrofuranyl.

17. A compound which is:
    2-Methyl-6-(5-(1-(4-(trifluoromethyl)phenyl)ethyl)thiazol-2-yl)pyrimidin-4(3H)-one,
    2-Methyl-6-(2-(1-(4-(trifluoromethyl)phenyl)ethyl)thiazol-4-yl)pyrimidin-4(3H)-one,
    2-Methyl-6-(4-(1-(4-(trifluoromethyl)phenyl)ethyl)thiazol-2-yl)pyrimidin-4(3H)-one,
    (S)-6-(5-(1-(2-fluoro-4-(trifluoromethyl)phenyl)ethyl)-1,3,4-thiadiazol-2-yl)-2-methylpyrimidin-4(3H)-one,
    (R)-6-(5-(1-(2-fluoro-4-(trifluoromethyl)phenyl)ethyl)-1,3,4-thiadiazol-2-yl)-2-methylpyrimidin-4(3H)-one,
    (S)-2-methyl-6-(5-(1-(4-(trifluoromethyl)phenyl)ethyl)-1,3,4-thiadiazol-2-yl)pyrimidin-4(3H)-one,
    (R)-2-methyl-6-(5-(1-(4-(trifluoromethyl)phenyl)ethyl)-1,3,4-thiadiazol-2-yl)pyrimidin-4(3H)-one,
    2-Methyl-6-(5-(1-(4-(trifluoromethyl)phenyl)ethyl)oxazol-2-yl)pyrimidin-4(3H)-one,
    (S)-2-methyl-6-(5-(1-(4-(trifluoromethyl)phenyl)ethyl)-1,3,4-oxadiazol-2-yl)pyrimidin-4(3H)-one,
    (R)-2-methyl-6-(5-(1-(4-(trifluoromethyl)phenyl)ethyl)-1,3,4-oxadiazol-2-yl)pyrimidin-4(3H)-one,
    2-Methyl-6-(5-(1-(4-(trifluoromethyl)phenyl)ethyl)-1,2,4-oxadiazol-3-yl)pyrimidin-4(3H)-one,
    2-Methyl-6-(3-(1-(4-(trifluoromethyl)phenyl)ethyl)-1,2,4-oxadiazol-5-yl)pyrimidin-4(3H)one,
    2-Methyl-6-(5-(1-(4-(trifluoromethyl)phenyl)ethyl)-1H-imidazol-2-yl)pyrimidin-4(3H)-one,
    (S)-6-(1-(1-(2-fluoro-4-(trifluoromethyl)phenyl)ethyl)-1H-imidazol-4-yl)-2-methylpyrimidin-4(3H)-one,
    (R)-6-(1-(1-(2-fluoro-4-(trifluoromethyl)phenyl)ethyl)-1H-imidazol-4-yl)-2-methylpyrimidin-4(3H)-one,
    (S)-2-methyl-6-(1-(1-(4-(trifluoromethyl)phenyl)ethyl)-1H-imidazol-4-yl)pyrimidin-4(3H)-one,
    (R)-2-methyl-6-(1-(1-(4-(trifluoromethyl)phenyl)ethyl)-1H-imidazol-4-yl)pyrimidin-4(3H)-one,
    (S)-2-(3,4-dimethoxybenzyl)-6-(1-(1-(2-fluoro-4-(trifluoromethyl)phenyl)ethyl)-1H-imidazol-4-yl)pyrimidin-4(3H)-one,
    (R)-2-(3,4-dimethoxybenzyl)-6-(1-(1-(2-fluoro-4-(trifluoromethyl)phenyl)ethyl)-1H-imidazol-4-yl)pyrimidin-4(3H)-one,
    6-(1-(1-(2-Fluoro-4-(trifluoromethyl)phenyl)propyl)-1H-imidazol-4-yl)-2-methylpyrimidin-4(3H)-one,
    6-(1-(1-(2-Fluoro-4-(trifluoromethyl)phenyl)-2-methylpropyl)-1H-imidazol-4-yl)-2-methylpyrimidin-4(3H)-one,
    2-methyl-6-(4-(1-(4-(trifluoromethyl)phenyl)ethyl)pyridin-2-yl)pyrimidin-4(3H)-one,
    (S)-2-Methyl-6-(5-(1-(4-(trifluoromethyl)phenyl)ethyl)pyridin-3-yl)pyrimidin-4(3H)-one,
    (R)-2-Methyl-6-(5-(1-(4-(trifluoromethyl)phenyl)ethyl)pyridin-3-yl)pyrimidin-4(3H)-one,
    6-(5-(Hydroxy(4-(trifluoromethyl)phenyl)methyl)pyridin-3-yl)-2-methylpyrimidin-4(3H)-one,
    6-(5-(1-Hydroxy-1-(4-(trifluoromethyl)phenyl)ethyl)pyridin-3-yl)-2-methylpyrimidin-4(3H)-one,
    2-Methyl-6-(2-(1-(4-(trifluoromethyl)phenyl)ethyl)pyridin-4-yl)pyrimidin-4(3H)-one,
    6-(2-(1-hydroxy-1-(4-(trifluoromethyl)phenyl)ethyl)pyridin-4-yl)-2-methylpyrimidin-4(3H)-one,
    2-Methyl-6-(6-(1-(4-(trifluoromethyl)phenyl)ethyl)pyrazin-2-yl)pyrimidin-4(3H)-one,
    (S)-6'-(1-(2-fluoro-4-(trifluoromethyl)phenyl)ethyl)-2-methyl-[4,4'-bipyrimidin]-6(1H)-one,
    (R)-6'-(1-(2-fluoro-4-(trifluoromethyl)phenyl)ethyl)-2-methyl-[4,4'-bipyrimidin]-6(1H)-one,
    (S)-2-methyl-6'-(1-(4-(trifluoromethyl)phenyl)ethyl)-[4,4'-bipyrimidin]-6(1H)-one,
    (R)-2-methyl-6'-(1-(4-(trifluoromethyl)phenyl)ethyl)-[4,4'-bipyrimidin]-6(1H)-one,
    (S)-6'-(1-(4-(difluoro-methoxy)-3-fluorophenyl)ethyl)-2-methyl-[4,4'-bipyrimidin]-6(1H)-one,
    (R)-6'-(1-(4-(difluoro-methoxy)-3-fluorophenyl)ethyl)-2-methyl-[4,4'-bipyrimidin]-6(1H)-one,
    (S)-6'-(1-(4-(1,1-difluoroethyl)phenyl)ethyl)-2-methyl-[4,4'-bipyrimidin]-6(1H)-one,
    (R)-6'-(1-(4-(1,1-difluoroethyl)phenyl)ethyl)-2-methyl-[4,4'-bipyrimidin]-6(1H)-one,
    (S)-6'-(1-(4-(difluoro-methyl)-3-fluoro-phenyl)ethyl)-2-methyl-[4,4'-bipyrimidin]-6(1H)-one,
    (R)-6'-(1-(4-(difluoro-methyl)-3-fluoro-phenyl)ethyl)-2-methyl-[4,4'-bipyrimidin]-6(1H)-one,
    (S)-6'-(1-(3-fluoro-4-(trifluoromethoxy)phenyl)ethyl)-2-methyl-[4,4'-bipyrimidin]-6(1H)-one,
    (R)-6'-(1-(3-fluoro-4-(trifluoromethoxy)phenyl)ethyl)-2-methyl-[4,4'-bipyrimidin]-6(1H)-one,
    (S)-6'-(1-(3-fluoro-4-(trifluoromethyl)phenyl)ethyl)-2-methyl-[4,4'-bipyrimidin]-6(1H)-one,
    (R)-6'-(1-(3-fluoro-4-(trifluoromethyl)phenyl)ethyl)-2-methyl-[4,4'-bipyrimidin]-6(1H)-one,
    (S)-2-methyl-6'-(1-(4-(trifluoromethoxy)phenyl)ethyl)-[4,4'-bipyrimidin]-6(1H)-one,
    (R)-2-methyl-6'-(1-(4-(trifluoromethoxy)phenyl)ethyl)-[4,4'-bipyrimidin]-6(1H)-one,
    (S)-6'-(1-(4-(2-hydroxypropan-2-yl)phenyl)ethyl)-2-methyl-[4,4'-bipyrimidin]-6(1H)-one,
    (R)-6'-(1-(4-(2-hydroxypropan-2-yl)phenyl)ethyl)-2-methyl-[4,4'-bipyrimidin]-6(1H)-one,
    2,2'-dimethyl-6'-(1-(4-(trifluoromethyl)phenyl)ethyl)-[4,4'-bipyrimidin]-6(1H)-one,
    or a pharmaceutically acceptable salt thereof.

18. A pharmaceutical composition which comprises a pharmaceutically acceptable carrier and a compound of claim 1, or a pharmaceutically acceptable salt thereof.

19. A method of treating psychotic disorders, delusional disorders and drug induced psychosis; anxiety disorders, movement disorders, mood disorders, Alzheimer's disease, schizophrenia, migraines, Huntington's disease, Parkinson's disease, Parkinson's disease dementia (PDD), and neurodegenerative disorders comprising administering a compound of claim 1 or a pharmaceutically acceptable salt thereof.

* * * * *